US007608452B2

(12) United States Patent
Presnell et al.

(10) Patent No.: US 7,608,452 B2
(45) Date of Patent: Oct. 27, 2009

(54) POLYNUCLEOTIDES ENCODING CYTOKINE RECEPTOR ZCYTOR19

(75) Inventors: Scott R. Presnell, Tacoma, WA (US); Theodore E. Whitmore, Redmond, WA (US); Francis J. Grant, Seattle, WA (US); Emily C. Costerison, San Francisco, CA (US)

(73) Assignee: ZymoGenetics, LLC, Nashville, TN (US)

( * ) Notice: Subject to any disclaimer, the term of this patent is extended or adjusted under 35 U.S.C. 154(b) by 0 days.

(21) Appl. No.: 11/539,064

(22) Filed: Oct. 5, 2006

(65) Prior Publication Data

US 2007/0111942 A1 May 17, 2007

Related U.S. Application Data

(63) Continuation of application No. 11/165,141, filed on Jun. 23, 2005, now abandoned, which is a continuation of application No. 09/995,898, filed on Nov. 28, 2001, now abandoned.

(60) Provisional application No. 60/253,561, filed on Nov. 28, 2000, provisional application No. 60/267,211, filed on Feb. 7, 2001.

(51) Int. Cl.
*C12N 5/10* (2006.01)
*C12N 15/10* (2006.01)
*C12N 15/12* (2006.01)
*C07K 14/715* (2006.01)

(52) U.S. Cl. ..................... 435/325; 536/23.1; 536/23.5; 435/320.1; 435/252.3; 435/254.11

(58) Field of Classification Search ....................... None
See application file for complete search history.

(56) References Cited

U.S. PATENT DOCUMENTS

| | | | |
|---|---|---|---|
| 7,033,787 | B2 | 4/2006 | Renauld et al. |
| 7,060,800 | B2 | 6/2006 | Gorman |
| 2002/0142292 | A1 | 10/2002 | Parham et al. |
| 2003/0158100 | A1 | 8/2003 | Renauld et al. |
| 2003/0180752 | A1 | 9/2003 | Liu et al. |
| 2005/0266485 | A1 | 12/2005 | Presnell et al. |
| 2007/0048799 | A1 | 3/2007 | Presnell et al. |
| 2007/0048804 | A1 | 3/2007 | Presnell et al. |
| 2007/0048846 | A1 | 3/2007 | Presnell et al. |
| 2007/0048847 | A1 | 3/2007 | Presnell et al. |
| 2007/0117165 | A1 | 5/2007 | Presnell et al. |
| 2007/0122879 | A1 | 5/2007 | Presnell et al. |
| 2007/0134727 | A1 | 6/2007 | Presnell et al. |
| 2007/0264685 | A1 | 11/2007 | Presnell et al. |

FOREIGN PATENT DOCUMENTS

| | | |
|---|---|---|
| WO | WO 98/37193 | 8/1998 |
| WO | WO 99/07848 | 2/1999 |
| WO | WO 01/02568 | 1/2001 |
| WO | WO 02/20569 | 3/2002 |
| WO | WO 02/44209 | 6/2002 |
| WO | WO 02/086087 | 10/2002 |
| WO | WO 03/031620 | 4/2003 |
| WO | WO 03/040345 | 5/2003 |
| WO | WO 03/057711 | 7/2003 |
| WO | WO 03/066002 | 8/2003 |
| WO | WO 2004/037995 | 5/2004 |
| WO | WO 2004/074320 | 9/2004 |

OTHER PUBLICATIONS

GenBank Accession AL358412.8, Homo sapiens chromosome 1 clone RP11-509F14, Oct. 29, 2000.*
Nilsson et al. Fusion proteins in biotechnology and structural biology, Current Op. Struct. Biotech. 2:569-575, 1992.*
Phillips, A.J., The challenge of gene therapy and DNA delivery, J. Pharmacy Pharmacol. 53:1169-1174, 2001.*
Dracopoli et al., *Proc. Natl. Acad. Sci. 86*:4614-4618, 1989.
Dumoutier et al., *J. Biochem 370*:391-396, 2003.
Gadina, M. et al., *Curr Opin Infect Dis 16* (3):211-217, 2003.
Genuardi et al., *Am. Hum. Genet. 45*:73-82, 1989.
Incyte Pharmaceuticals, Inc. clone, 1996: INC1274993.
Incyte Pharmaceuticals, Inc. clone, 1996: INC2025095.
Incyte Pharmaceuticals, Inc. Library, 1996: KERANOT02.
Incyte Pharmaceuticals, Inc. Library, 1996: TESTTUT02.
Incyte Pharmaceuticals, Inc. clone, 2000: INC7127190H2.
Incyte Pharmaceuticals, Inc. clone, 2000: INC7128744.
Incyte Pharmaceuticals, Inc. clone, 2000: INC8134754.
Kotenko et al., *Nature Immunology 4*(1):69-71, Jan. 2003.
Renauld, J-C, *Nature Reviews-Immunology 3*: 667-676, 2003.
Ritke et al., *Cytogenet. Cell. Genet. 50*:84-90, 1989.
Sheppard et al., Accession No. AAN28268, Nov. 2002, Whole Sequence.
Sheppard et al., *Nature Immunology 4*(1): 63-68, 2003.
Soos et al., *The Cytokine Handbook*, 4th Edition, pp. 549-566, Angus W. Thomson and Michael T. Lotze, 2003.
TIGR, Tentative Human Consensus, 1997;THC_W16444.
Vilcek, J., *Nature Immunology 4*(1): Jan. 8-9, 2003.
Wei et al., EBI, Hinxton, UK Database, Accession No. BE244935, 2000.

(Continued)

*Primary Examiner*—Lorraine Spector
*Assistant Examiner*—Claire Kaufman
(74) *Attorney, Agent, or Firm*—Robyn Adams

(57) ABSTRACT

Novel polypeptides, polynucleotides encoding the polypeptides, and related compositions and methods are disclosed for zcytor19, a novel class II cytokine receptor. The polypeptides may be used within methods for detecting ligands that stimulate the proliferation and/or development of hematopoietic, lymphoid and myeloid cells in vitro and in vivo. Ligand-binding receptor polypeptides can also be used to block ligand activity in vitro and in vivo. The polynucleotides encoding zcytor19, are located on chromosome 1p36.11, and can be used to identify a region of the genome associated with human disease states. The present invention also includes methods for producing the protein, uses therefor and antibodies thereto.

8 Claims, No Drawings

OTHER PUBLICATIONS

Wei et al., Genbank Database, Pediatric Leukemia cDNA Sequencing Project, 2000: EST5272157.

Wei et al., Genbank Database, Pediatric Leukemia cDNA Sequencing Project, 2000: EST5273479.

Wilson et al., Genbank Database, The WashU-Merck EST Project, 1995: EST522113.

Langer et al., "The class II cytokine receptor (CRF2) family: overview and patterns of receptor-ligand interactions," Cytokine & Growth Factor Rev. 15(1): 33-48, 2004.

* cited by examiner

SEQUENCE LISTING

```
<160> NUMBER OF SEQ ID NOS: 50

<210> SEQ ID NO 1
<211> LENGTH: 1476
<212> TYPE: DNA
<213> ORGANISM: Homo sapiens
<220> FEATURE:
<221> NAME/KEY: CDS
<222> LOCATION: (1)...(1473)

<400> SEQUENCE: 1

atg gcg ggg ccc gag cgc tgg ggc ccc ctg ctc ctg tgc ctg ctg cag        48
Met Ala Gly Pro Glu Arg Trp Gly Pro Leu Leu Leu Cys Leu Leu Gln
 1               5                  10                  15

gcc gct cca ggg agg ccc cgt ctg gcc cct ccc cag aat gtg acg ctg        96
Ala Ala Pro Gly Arg Pro Arg Leu Ala Pro Pro Gln Asn Val Thr Leu
            20                  25                  30

ctc tcc cag aac ttc agc gtg tac ctg aca tgg ctc cca ggg ctt ggc       144
Leu Ser Gln Asn Phe Ser Val Tyr Leu Thr Trp Leu Pro Gly Leu Gly
        35                  40                  45

aac ccc cag gat gtg acc tat ttt gtg gcc tat cag agc tct ccc acc       192
Asn Pro Gln Asp Val Thr Tyr Phe Val Ala Tyr Gln Ser Ser Pro Thr
    50                  55                  60

cgt aga cgg tgg cgc gaa gtg gaa gag tgt gcg gga acc aag gag ctg       240
Arg Arg Arg Trp Arg Glu Val Glu Glu Cys Ala Gly Thr Lys Glu Leu
 65                  70                  75                  80

cta tgt tct atg atg tgc ctg aag aaa cag gac ctg tac aac aag ttc       288
Leu Cys Ser Met Met Cys Leu Lys Lys Gln Asp Leu Tyr Asn Lys Phe
                85                  90                  95

aag gga cgc gtg cgg acg gtt tct ccc agc tcc aag tcc ccc tgg gtg       336
Lys Gly Arg Val Arg Thr Val Ser Pro Ser Ser Lys Ser Pro Trp Val
            100                 105                 110

gag tcc gaa tac ctg gat tac ctt ttt gaa gtg gag ccg gcc cca cct       384
Glu Ser Glu Tyr Leu Asp Tyr Leu Phe Glu Val Glu Pro Ala Pro Pro
        115                 120                 125
```

-continued

```
gtc ctg gtg ctc acc cag acg gag gag atc ctg agt gcc aat gcc acg      432
Val Leu Val Leu Thr Gln Thr Glu Glu Ile Leu Ser Ala Asn Ala Thr
    130                 135                 140

tac cag ctg ccc ccc tgc atg ccc cca ctg ttt ctg aag tat gag gtg      480
Tyr Gln Leu Pro Pro Cys Met Pro Pro Leu Phe Leu Lys Tyr Glu Val
145                 150                 155                 160

gca ttt tgg ggg ggg ggg gcc gga acc aag acc cta ttt cca gtc act      528
Ala Phe Trp Gly Gly Gly Ala Gly Thr Lys Thr Leu Phe Pro Val Thr
                165                 170                 175

ccc cat ggc cag cca gtc cag atc act ctc cag cca gct gcc agc gaa      576
Pro His Gly Gln Pro Val Gln Ile Thr Leu Gln Pro Ala Ala Ser Glu
            180                 185                 190

cac cac tgc ctc agt gcc aga acc atc tac acg ttc agt gtc ccg aaa      624
His His Cys Leu Ser Ala Arg Thr Ile Tyr Thr Phe Ser Val Pro Lys
        195                 200                 205

tac agc aag ttc tct aag ccc acc tgc ttc ttg ctg gag gtc cca gaa      672
Tyr Ser Lys Phe Ser Lys Pro Thr Cys Phe Leu Leu Glu Val Pro Glu
    210                 215                 220

gcc aac tgg gct ttc ctg gtg ctg cca tcg ctt ctg ata ctg ctg tta      720
Ala Asn Trp Ala Phe Leu Val Leu Pro Ser Leu Leu Ile Leu Leu Leu
225                 230                 235                 240

gta att gcc gca ggg ggt gtg atc tgg aag acc ctc atg ggg aac ccc      768
Val Ile Ala Ala Gly Gly Val Ile Trp Lys Thr Leu Met Gly Asn Pro
                245                 250                 255

tgg ttt cag cgg gca aag atg cca cgg gcc ctg gaa ctg acc aga ggg      816
Trp Phe Gln Arg Ala Lys Met Pro Arg Ala Leu Glu Leu Thr Arg Gly
            260                 265                 270

gtc agg ccg acg cct cga gtc agg gcc cca gcc acc caa cag aca aga      864
Val Arg Pro Thr Pro Arg Val Arg Ala Pro Ala Thr Gln Gln Thr Arg
        275                 280                 285

tgg aag aag gac ctt gca gag gac gaa gag gag gag gat gag gag gac      912
Trp Lys Lys Asp Leu Ala Glu Asp Glu Glu Glu Glu Asp Glu Glu Asp
    290                 295                 300

aca gaa gat ggc gtc agc ttc cag ccc tac att gaa cca cct tct ttc      960
Thr Glu Asp Gly Val Ser Phe Gln Pro Tyr Ile Glu Pro Pro Ser Phe
305                 310                 315                 320

ctg ggg caa gag cac cag gct cca ggg cac tcg gag gct ggt ggg gtg     1008
Leu Gly Gln Glu His Gln Ala Pro Gly His Ser Glu Ala Gly Gly Val
                325                 330                 335

gac tca ggg agg ccc agg gct cct ctg gtc cca agc gaa ggc tcc tct     1056
Asp Ser Gly Arg Pro Arg Ala Pro Leu Val Pro Ser Glu Gly Ser Ser
            340                 345                 350

gct tgg gat tct tca gac aga agc tgg gcc agc act gtg gac tcc tcc     1104
Ala Trp Asp Ser Ser Asp Arg Ser Trp Ala Ser Thr Val Asp Ser Ser
        355                 360                 365

tgg gac agg gct ggg tcc tct ggc tat ttg gct gag aag ggg cca ggc     1152
Trp Asp Arg Ala Gly Ser Ser Gly Tyr Leu Ala Glu Lys Gly Pro Gly
    370                 375                 380

caa ggg ccg ggt ggg gat ggg cac caa gaa tct ctc cca cca cct gaa     1200
Gln Gly Pro Gly Gly Asp Gly His Gln Glu Ser Leu Pro Pro Pro Glu
385                 390                 395                 400

ttc tcc aag gac tcg ggt ttc ctg gaa gag ctc cca gaa gat aac ctc     1248
Phe Ser Lys Asp Ser Gly Phe Leu Glu Glu Leu Pro Glu Asp Asn Leu
                405                 410                 415

tcc tcc tgg gcc acc tgg ggc acc tta cca ccg gag ccg aat ctg gtc     1296
Ser Ser Trp Ala Thr Trp Gly Thr Leu Pro Pro Glu Pro Asn Leu Val
            420                 425                 430

cct ggg gga ccc cca gtt tct ctt cag aca ctg acc ttc tgc tgg gaa     1344
Pro Gly Gly Pro Pro Val Ser Leu Gln Thr Leu Thr Phe Cys Trp Glu
        435                 440                 445
```

-continued

```
agc agc cct gag gag gaa gag gag gcg agg gaa tca gaa att gag gac      1392
Ser Ser Pro Glu Glu Glu Glu Glu Ala Arg Glu Ser Glu Ile Glu Asp
    450                 455                 460

agc gat gcg ggc agc tgg ggg gct gag agc acc cag agg acc gag gac      1440
Ser Asp Ala Gly Ser Trp Gly Ala Glu Ser Thr Gln Arg Thr Glu Asp
465                 470                 475                 480

agg ggc cgg aca ttg ggg cat tac atg gcc agg tga                      1476
Arg Gly Arg Thr Leu Gly His Tyr Met Ala Arg
                485                 490


<210> SEQ ID NO 2
<211> LENGTH: 491
<212> TYPE: PRT
<213> ORGANISM: Homo sapiens

<400> SEQUENCE: 2

Met Ala Gly Pro Glu Arg Trp Gly Pro Leu Leu Leu Cys Leu Leu Gln
 1               5                  10                  15

Ala Ala Pro Gly Arg Pro Arg Leu Ala Pro Pro Gln Asn Val Thr Leu
            20                  25                  30

Leu Ser Gln Asn Phe Ser Val Tyr Leu Thr Trp Leu Pro Gly Leu Gly
        35                  40                  45

Asn Pro Gln Asp Val Thr Tyr Phe Val Ala Tyr Gln Ser Ser Pro Thr
    50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
        115                 120                 125

Val Leu Val Leu Thr Gln Thr Glu Glu Ile Leu Ser Ala Asn Ala Thr
    130                 135                 140

Tyr Gln Leu Pro Pro Cys Met Pro Pro Leu Phe Leu Lys Tyr Glu Val
145                 150                 155                 160

Ala Phe Trp Gly Gly Gly Ala Gly Thr Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
        195                 200                 205

Tyr Ser Lys Phe Ser Lys Pro Thr Cys Phe Leu Leu Glu Val Pro Glu
    210                 215                 220

Ala Asn Trp Ala Phe Leu Val Leu Pro Ser Leu Leu Ile Leu Leu Leu
225                 230                 235                 240

Val Ile Ala Ala Gly Gly Val Ile Trp Lys Thr Leu Met Gly Asn Pro
                245                 250                 255

Trp Phe Gln Arg Ala Lys Met Pro Arg Ala Leu Glu Leu Thr Arg Gly
            260                 265                 270

Val Arg Pro Thr Pro Arg Val Arg Ala Pro Ala Thr Gln Gln Thr Arg
        275                 280                 285

Trp Lys Lys Asp Leu Ala Glu Asp Glu Glu Glu Glu Asp Glu Glu Asp
    290                 295                 300

Thr Glu Asp Gly Val Ser Phe Gln Pro Tyr Ile Glu Pro Pro Ser Phe
```

-continued

```
305                 310                 315                 320

Leu Gly Gln Glu His Gln Ala Pro Gly His Ser Glu Ala Gly Gly Val
                325                 330                 335

Asp Ser Gly Arg Pro Arg Ala Pro Leu Val Pro Ser Glu Gly Ser Ser
            340                 345                 350

Ala Trp Asp Ser Ser Asp Arg Ser Trp Ala Ser Thr Val Asp Ser Ser
        355                 360                 365

Trp Asp Arg Ala Gly Ser Ser Gly Tyr Leu Ala Glu Lys Gly Pro Gly
    370                 375                 380

Gln Gly Pro Gly Gly Asp Gly His Gln Glu Ser Leu Pro Pro Pro Glu
385                 390                 395                 400

Phe Ser Lys Asp Ser Gly Phe Leu Glu Glu Leu Pro Glu Asp Asn Leu
                405                 410                 415

Ser Ser Trp Ala Thr Trp Gly Thr Leu Pro Pro Glu Pro Asn Leu Val
            420                 425                 430

Pro Gly Gly Pro Pro Val Ser Leu Gln Thr Leu Thr Phe Cys Trp Glu
        435                 440                 445

Ser Ser Pro Glu Glu Glu Glu Glu Ala Arg Glu Ser Glu Ile Glu Asp
    450                 455                 460

Ser Asp Ala Gly Ser Trp Gly Ala Glu Ser Thr Gln Arg Thr Glu Asp
465                 470                 475                 480

Arg Gly Arg Thr Leu Gly His Tyr Met Ala Arg
                485                 490


<210> SEQ ID NO 3
<211> LENGTH: 1473
<212> TYPE: DNA
<213> ORGANISM: Artificial Sequence
<220> FEATURE:
<223> OTHER INFORMATION: Degenerate polynucleotide seuquence of
      SEQ ID NO:2
<220> FEATURE:
<221> NAME/KEY: misc_feature
<222> LOCATION: (1)...(1473)
<223> OTHER INFORMATION: n = A,T,C or G

<400> SEQUENCE: 3

atggcnggnc cngarmgntg gggnccnytn ytnytntgyy tnytncargc ngcnccnggn     60

mgnccnmgny tngcnccncc ncaraaygtn acnytnytnw sncaraaytt ywsngtntay    120

ytnacntggy tnccnggnyt nggnaayccn cargaygtna cntayttygt ngcntaycar    180

wsnwsnccna cnmgnmgnmg ntggmgngar gtngargart gygcnggnac naargarytn    240

ytntgywsna tgatgtgyyt naaraarcar gayytntaya ayaarttyaa rggnmgngtn    300

mgnacngtnw snccnwsnws naarwsnccn tgggtngarw sngartayyt ngaytayytn    360

ttygargtng arccngcncc nccngtnytn gtnytnacnc aracngarga rathytnwsn    420

gcnaaygcna cntaycaryt nccnccntgy atgccnccny tnttyytnaa rtaygargtn    480

gcnttytggg gnggnggngc nggnacnaar acnytnttyc cngtnacncc ncayggncar    540

ccngtncara thacnytnca rccngcngcn wsngarcayc aytgyytnws ngcnmgnacn    600

athtayacnt tywsngtncc naartaywsn aarttywsna arccnacntg yttyytnytn    660

gargtnccng argcnaaytg ggcnttyytn gtnytnccnw snytnytnat hytnytnytn    720

gtnathgcng cnggnggngt nathtggaar acnytnatgg gnaayccntg gttycarmgn    780

gcnaaratgc cnmgngcnyt ngarytnacn mgnggngtnm gnccnacncc nmgngtnmgn    840

gcnccngcna cncarcarac nmgntggaar aargayytng cngargayga rgargargar    900
```

-continued

```
gaygargarg ayacngarga yggngtnwsn ttycarccnt ayathgarcc nccnwsntty    960

ytnggncarg arcaycargc nccnggncay wsngargcng gnggngtnga ywsnggnmgn   1020

ccnmgngcnc cnytngtncc nwsngarggn wsnwsngcnt gggaywsnws ngaymgnwsn   1080

tgggcnwsna cngtngayws nwsntgggay mgngcnggnw snwsnggnta yytngcngar   1140

aarggnccng gncarggncc nggnggngay ggncaycarg arwsnytncc nccnccngar   1200

ttywsnaarg aywsnggntt yytngargar ytnccngarg ayaayytnws nwsntgggcn   1260

acntggggna cnytnccncc ngarccnaay ytngtnccng gnggnccncc ngtnwsnytn   1320

caracnytna cnttytgytg ggarwsnwsn ccngargarg argargargc nmgngarwsn   1380

garathgarg aywsngaygc nggnwsntgg ggngcngarw snacncarmg nacngargay   1440

mgnggnmgna cnytnggnca ytayatggcn mgn                                1473
```

<210> SEQ ID NO 4
<211> LENGTH: 203
<212> TYPE: PRT
<213> ORGANISM: Homo sapiens

<400> SEQUENCE: 4

```
Arg Pro Arg Leu Ala Pro Pro Gln Asn Val Thr Leu Leu Ser Gln Asn
 1               5                  10                  15

Phe Ser Val Tyr Leu Thr Trp Leu Pro Gly Leu Gly Asn Pro Gln Asp
            20                  25                  30

Val Thr Tyr Phe Val Ala Tyr Gln Ser Ser Pro Thr Arg Arg Arg Trp
        35                  40                  45

Arg Glu Val Glu Glu Cys Ala Gly Thr Lys Glu Leu Leu Cys Ser Met
    50                  55                  60

Met Cys Leu Lys Lys Gln Asp Leu Tyr Asn Lys Phe Lys Gly Arg Val
65                  70                  75                  80

Arg Thr Val Ser Pro Ser Ser Lys Ser Pro Trp Val Glu Ser Glu Tyr
                85                  90                  95

Leu Asp Tyr Leu Phe Glu Val Glu Pro Ala Pro Pro Val Leu Val Leu
            100                 105                 110

Thr Gln Thr Glu Glu Ile Leu Ser Ala Asn Ala Thr Tyr Gln Leu Pro
        115                 120                 125

Pro Cys Met Pro Pro Leu Phe Leu Lys Tyr Glu Val Ala Phe Trp Gly
    130                 135                 140

Gly Gly Ala Gly Thr Lys Thr Leu Phe Pro Val Thr Pro His Gly Gln
145                 150                 155                 160

Pro Val Gln Ile Thr Leu Gln Pro Ala Ala Ser Glu His His Cys Leu
                165                 170                 175

Ser Ala Arg Thr Ile Tyr Thr Phe Ser Val Pro Lys Tyr Ser Lys Phe
            180                 185                 190

Ser Lys Pro Thr Cys Phe Leu Leu Glu Val Pro
        195                 200
```

<210> SEQ ID NO 5
<211> LENGTH: 5
<212> TYPE: PRT
<213> ORGANISM: Artificial Sequence
<220> FEATURE:
<223> OTHER INFORMATION: WSXWS motif
<220> FEATURE:
<221> NAME/KEY: VARIANT
<222> LOCATION: (1)...(5)
<223> OTHER INFORMATION: Xaa = Any Amino Acid

<400> SEQUENCE: 5

Trp Ser Xaa Trp Ser
1 5

<210> SEQ ID NO 6
<211> LENGTH: 23
<212> TYPE: DNA
<213> ORGANISM: Artificial Sequence
<220> FEATURE:
<223> OTHER INFORMATION: Oligonucleotide primer ZC21195

<400> SEQUENCE: 6
gaggagacca taaccccga cag 23

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide primer ZC21196

<400> SEQUENCE: 7
catagctccc accacacgat ttt 23

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 8
caccagacat aatagctgac agact 25

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide primer ZC17574

<400> SEQUENCE: 9
ggtrttgctc agcatgcaca c 21

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide primer ZC17600

<400> SEQUENCE: 10
catgtaggcc atgaggtcca ccac 24

<210> SEQ ID NO 11
<211> LENGTH: 6
<212> TYPE: PRT
<213> ORGANISM: Artificial Sequence
<220> FEATURE:
<223> OTHER INFORMATION: Glu-Glu peptide tag

<400> SEQUENCE: 11

Glu Tyr Met Pro Met Glu
1 5

<210> SEQ ID NO 12
<211> LENGTH: 8
<212> TYPE: PRT
<213> ORGANISM: Artificial Sequence
<220> FEATURE:
<223> OTHER INFORMATION: FLAG peptide tag

<400> SEQUENCE: 12

```
Asp Tyr Lys Asp Asp Asp Asp Lys
 1               5
```

<210> SEQ ID NO 13
<211> LENGTH: 699
<212> TYPE: DNA
<213> ORGANISM: Homo sapiens

<400> SEQUENCE: 13

```
gagcccagat cttcagacaa aactcacaca tgcccaccgt gcccagcacc tgaagccgag     60

ggggcaccgt cagtcttcct cttcccccca aaacccaagg acaccctcat gatctcccgg    120

acccctgagg tcacatgcgt ggtggtggac gtgagccacg aagaccctga ggtcaagttc    180

aactggtacg tggacggcgt ggaggtgcat aatgccaaga caaagccgcg ggaggagcag    240

tacaacagca cgtaccgtgt ggtcagcgtc ctcaccgtcc tgcaccagga ctggctgaat    300

ggcaaggagt acaagtgcaa ggtctccaac aaagccctcc catcctccat cgagaaaacc    360

atctccaaag ccaaagggca gccccgagaa ccacaggtgt acaccctgcc cccatcccgg    420

gatgagctga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctacagca agctcaccgt ggacaagagc    600

aggtggcagc aggggaacgt cttctcatgc tccgtgatgc atgaggctct gcacaaccac    660

tacacgcaga agagcctctc cctgtctccg ggtaaataa                           699
```

<210> SEQ ID NO 14
<211> LENGTH: 990
<212> TYPE: DNA
<213> ORGANISM: Homo sapiens
<220> FEATURE:
<221> NAME/KEY: CDS
<222> LOCATION: (1)...(990)

<400> SEQUENCE: 14

```
gct agc acc aag ggc cca tcg gtc ttc ccc ctg gca ccc tcc tcc aag       48
Ala Ser Thr Lys Gly Pro Ser Val Phe Pro Leu Ala Pro Ser Ser Lys
 1               5                  10                  15

agc acc tct ggg ggc aca gcg gcc ctg ggc tgc ctg gtc aag gac tac       96
Ser Thr Ser Gly Gly Thr Ala Ala Leu Gly Cys Leu Val Lys Asp Tyr
            20                  25                  30

ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45

ggc gtg cac acc ttc ccg gct gtc cta cag tcc tca gga ctc tac tcc      192
Gly Val His Thr Phe Pro Ala Val Leu Gln Ser Ser Gly Leu Tyr Ser
     50                  55                  60

ctc agc agc gtg gtg acc gtg ccc tcc agc agc ttg ggc acc cag acc      240
Leu Ser Ser Val Val Thr Val Pro Ser Ser Ser Leu Gly Thr Gln Thr
 65                  70                  75                  80

tac atc tgc aac gtg aat cac aag ccc agc aac acc aag gtg gac aag      288
Tyr Ile Cys Asn Val Asn His Lys Pro Ser Asn Thr Lys Val Asp Lys
                 85                  90                  95
```

```
aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110

cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125

aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140

gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160

tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175

gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190

cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205

aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220

cag ccc cga gaa cca cag gtg tac acc ctg ccc cca tcc cgg gat gag      720
Gln Pro Arg Glu Pro Gln Val Tyr Thr Leu Pro Pro Ser Arg Asp Glu
225                 230                 235                 240

ctg acc aag aac cag gtc agc ctg acc tgc ctg gtc aaa ggc ttc tat      768
Leu Thr Lys Asn Gln Val Ser Leu Thr Cys Leu Val Lys Gly Phe Tyr
                245                 250                 255

ccc agc gac atc gcc gtg gag tgg gag agc aat ggg cag ccg gag aac      816
Pro Ser Asp Ile Ala Val Glu Trp Glu Ser Asn Gly Gln Pro Glu Asn
            260                 265                 270

aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
        275                 280                 285

ctc tac agc aag ctc acc gtg gac aag agc agg tgg cag cag ggg aac      912
Leu Tyr Ser Lys Leu Thr Val Asp Lys Ser Arg Trp Gln Gln Gly Asn
    290                 295                 300

gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320

cag aag agc ctc tcc ctg tct ccg ggt aaa                              990
Gln Lys Ser Leu Ser Leu Ser Pro Gly Lys
                325                 330
```

<210> SEQ ID NO 15
<211> LENGTH: 330
<212> TYPE: PRT
<213> ORGANISM: Homo sapiens

<400> SEQUENCE: 15

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 16
<211> LENGTH: 321
<212> TYPE: DNA
<213> ORGANISM: Homo sapiens
<220> FEATURE:
<221> NAME/KEY: CDS
<222> LOCATION: (1)...(321)

<400> SEQUENCE: 16

act gtg gct gca cca tct gtc ttc atc ttc ccg cca tct gat gag cag       48
Thr Val Ala Ala Pro Ser Val Phe Ile Phe Pro Pro Ser Asp Glu Gln
 1               5                  10                  15

ttg aaa tct ggt acc gcc tct gtt gtg tgc ctg ctg aat aac ttc tat       96
Leu Lys Ser Gly Thr Ala Ser Val Val Cys Leu Leu Asn Asn Phe Tyr
            20                  25                  30

ccc aga gag gcc aaa gta cag tgg aag gtg gat aac gcc ctc caa tcg      144
Pro Arg Glu Ala Lys Val Gln Trp Lys Val Asp Asn Ala Leu Gln Ser
        35                  40                  45

ggt aac tcc cag gag agt gtc aca gag cag gac agc aag gac agc acc      192
Gly Asn Ser Gln Glu Ser Val Thr Glu Gln Asp Ser Lys Asp Ser Thr
    50                  55                  60
```

-continued

```
tac agc ctc agc agc acc ctg acg ctg agc aaa gca gac tac gag aaa      240
Tyr Ser Leu Ser Ser Thr Leu Thr Leu Ser Lys Ala Asp Tyr Glu Lys
 65                  70                  75                  80

cac aaa gtc tac gcc tgc gaa gtc acc cat cag ggc ctg agc tcg ccc      288
His Lys Val Tyr Ala Cys Glu Val Thr His Gln Gly Leu Ser Ser Pro
                 85                  90                  95

gtc aca aag agc ttc aac agg gga gag tgt tag                          321
Val Thr Lys Ser Phe Asn Arg Gly Glu Cys  *
            100                 105
```

<210> SEQ ID NO 17
<211> LENGTH: 106
<212> TYPE: PRT
<213> ORGANISM: Homo sapiens

<400> SEQUENCE: 17

```
Thr Val Ala Ala Pro Ser Val Phe Ile Phe Pro Pro Ser Asp Glu Gln
 1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 18
<211> LENGTH: 1563
<212> TYPE: DNA
<213> ORGANISM: Homo sapiens
<220> FEATURE:
<221> NAME/KEY: CDS
<222> LOCATION: (1)...(1563)

<400> SEQUENCE: 18

```
atg gcg ggg ccc gag cgc tgg ggc ccc ctg ctc ctg tgc ctg ctg cag       48
Met Ala Gly Pro Glu Arg Trp Gly Pro Leu Leu Leu Cys Leu Leu Gln
 1               5                   10                  15

gcc gct cca ggg agg ccc cgt ctg gcc cct ccc cag aat gtg acg ctg       96
Ala Ala Pro Gly Arg Pro Arg Leu Ala Pro Pro Gln Asn Val Thr Leu
            20                  25                  30

ctc tcc cag aac ttc agc gtg tac ctg aca tgg ctc cca ggg ctt ggc      144
Leu Ser Gln Asn Phe Ser Val Tyr Leu Thr Trp Leu Pro Gly Leu Gly
        35                  40                  45

aac ccc cag gat gtg acc tat ttt gtg gcc tat cag agc tct ccc acc      192
Asn Pro Gln Asp Val Thr Tyr Phe Val Ala Tyr Gln Ser Ser Pro Thr
     50                  55                  60

cgt aga cgg tgg cgc gaa gtg gaa gag tgt gcg gga acc aag gag ctg      240
Arg Arg Arg Trp Arg Glu Val Glu Glu Cys Ala Gly Thr Lys Glu Leu
 65                  70                  75                  80

cta tgt tct atg atg tgc ctg aag aaa cag gac ctg tac aac aag ttc      288
Leu Cys Ser Met Met Cys Leu Lys Lys Gln Asp Leu Tyr Asn Lys Phe
                 85                  90                  95

aag gga cgc gtg cgg acg gtt tct ccc agc tcc aag tcc ccc tgg gtg      336
Lys Gly Arg Val Arg Thr Val Ser Pro Ser Ser Lys Ser Pro Trp Val
```

-continued

```
            100                 105                 110

gag tcc gaa tac ctg gat tac ctt ttt gaa gtg gag ccg gcc cca cct     384
Glu Ser Glu Tyr Leu Asp Tyr Leu Phe Glu Val Glu Pro Ala Pro Pro
        115                 120                 125

gtc ctg gtg ctc acc cag acg gag gag atc ctg agt gcc aat gcc acg     432
Val Leu Val Leu Thr Gln Thr Glu Glu Ile Leu Ser Ala Asn Ala Thr
    130                 135                 140

tac cag ctg ccc ccc tgc atg ccc cca ctg gat ctg aag tat gag gtg     480
Tyr Gln Leu Pro Pro Cys Met Pro Pro Leu Asp Leu Lys Tyr Glu Val
145                 150                 155                 160

gca ttc tgg aag gag ggg gcc gga aac aag acc cta ttt cca gtc act     528
Ala Phe Trp Lys Glu Gly Ala Gly Asn Lys Thr Leu Phe Pro Val Thr
                165                 170                 175

ccc cat ggc cag cca gtc cag atc act ctc cag cca gct gcc agc gaa     576
Pro His Gly Gln Pro Val Gln Ile Thr Leu Gln Pro Ala Ala Ser Glu
            180                 185                 190

cac cac tgc ctc agt gcc aga acc atc tac acg ttc agt gtc ccg aaa     624
His His Cys Leu Ser Ala Arg Thr Ile Tyr Thr Phe Ser Val Pro Lys
        195                 200                 205

tac agc aag ttc tct aag ccc acc tgc ttc ttg ctg gag gtc cca gaa     672
Tyr Ser Lys Phe Ser Lys Pro Thr Cys Phe Leu Leu Glu Val Pro Glu
    210                 215                 220

gcc aac tgg gct ttc ctg gtg ctg cca tcg ctt ctg ata ctg ctg tta     720
Ala Asn Trp Ala Phe Leu Val Leu Pro Ser Leu Leu Ile Leu Leu Leu
225                 230                 235                 240

gta att gcc gca ggg ggt gtg atc tgg aag acc ctc atg ggg aac ccc     768
Val Ile Ala Ala Gly Gly Val Ile Trp Lys Thr Leu Met Gly Asn Pro
                245                 250                 255

tgg ttt cag cgg gca aag atg cca cgg gcc ctg gac ttt tct gga cac     816
Trp Phe Gln Arg Ala Lys Met Pro Arg Ala Leu Asp Phe Ser Gly His
            260                 265                 270

aca cac cct gtg gca acc ttt cag ccc agc aga cca gag tcc gtg aat     864
Thr His Pro Val Ala Thr Phe Gln Pro Ser Arg Pro Glu Ser Val Asn
        275                 280                 285

gac ttg ttc ctc tgt ccc caa aag gaa ctg acc aga ggg gtc agg ccg     912
Asp Leu Phe Leu Cys Pro Gln Lys Glu Leu Thr Arg Gly Val Arg Pro
    290                 295                 300

acg cct cga gtc agg gcc cca gcc acc caa cag aca aga tgg aag aag     960
Thr Pro Arg Val Arg Ala Pro Ala Thr Gln Gln Thr Arg Trp Lys Lys
305                 310                 315                 320

gac ctt gca gag gac gaa gag gag gag gat gag gag gac aca gaa gat    1008
Asp Leu Ala Glu Asp Glu Glu Glu Glu Asp Glu Glu Asp Thr Glu Asp
                325                 330                 335

ggc gtc agc ttc cag ccc tac att gaa cca cct tct ttc ctg ggg caa    1056
Gly Val Ser Phe Gln Pro Tyr Ile Glu Pro Pro Ser Phe Leu Gly Gln
            340                 345                 350

gag cac cag gct cca ggg cac tcg gag gct ggt ggg gtg gac tca ggg    1104
Glu His Gln Ala Pro Gly His Ser Glu Ala Gly Gly Val Asp Ser Gly
        355                 360                 365

agg ccc agg gct cct ctg gtc cca agc gaa ggc tcc tct gct tgg gat    1152
Arg Pro Arg Ala Pro Leu Val Pro Ser Glu Gly Ser Ser Ala Trp Asp
    370                 375                 380

tct tca gac aga agc tgg gcc agc act gtg gac tcc tcc tgg gac agg    1200
Ser Ser Asp Arg Ser Trp Ala Ser Thr Val Asp Ser Ser Trp Asp Arg
385                 390                 395                 400

gct ggg tcc tct ggc tat ttg gct gag aag ggg cca ggc caa ggg ccg    1248
Ala Gly Ser Ser Gly Tyr Leu Ala Glu Lys Gly Pro Gly Gln Gly Pro
                405                 410                 415

ggt ggg gat ggg cac caa gaa tct ctc cca cca cct gaa ttc tcc aag    1296
```

-continued

```
Gly Gly Asp Gly His Gln Glu Ser Leu Pro Pro Pro Glu Phe Ser Lys
            420                 425                 430

gac tcg ggt ttc ctg gaa gag ctc cca gaa gat aac ctc tcc tcc tgg      1344
Asp Ser Gly Phe Leu Glu Glu Leu Pro Glu Asp Asn Leu Ser Ser Trp
        435                 440                 445

gcc acc tgg ggc acc tta cca ccg gag ccg aat ctg gtc cct ggg gga      1392
Ala Thr Trp Gly Thr Leu Pro Pro Glu Pro Asn Leu Val Pro Gly Gly
    450                 455                 460

ccc cca gtt tct ctt cag aca ctg acc ttc tgc tgg gaa agc agc cct      1440
Pro Pro Val Ser Leu Gln Thr Leu Thr Phe Cys Trp Glu Ser Ser Pro
465                 470                 475                 480

gag gag gaa gag gag gcg agg gaa tca gaa att gag gac agc gat gcg      1488
Glu Glu Glu Glu Glu Ala Arg Glu Ser Glu Ile Glu Asp Ser Asp Ala
                485                 490                 495

ggc agc tgg ggg gct gag agc acc cag agg acc gag gac agg ggc cgg      1536
Gly Ser Trp Gly Ala Glu Ser Thr Gln Arg Thr Glu Asp Arg Gly Arg
            500                 505                 510

aca ttg ggg cat tac atg gcc agg tga                                  1563
Thr Leu Gly His Tyr Met Ala Arg  *
        515                 520


<210> SEQ ID NO 19
<211> LENGTH: 520
<212> TYPE: PRT
<213> ORGANISM: Homo sapiens

<400> SEQUENCE: 19

Met Ala Gly Pro Glu Arg Trp Gly Pro Leu Leu Leu Cys Leu Leu Gln
 1               5                  10                  15

Ala Ala Pro Gly Arg Pro Arg Leu Ala Pro Pro Gln Asn Val Thr Leu
            20                  25                  30

Leu Ser Gln Asn Phe Ser Val Tyr Leu Thr Trp Leu Pro Gly Leu Gly
        35                  40                  45

Asn Pro Gln Asp Val Thr Tyr Phe Val Ala Tyr Gln Ser Ser Pro Thr
    50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
        115                 120                 125

Val Leu Val Leu Thr Gln Thr Glu Glu Ile Leu Ser Ala Asn Ala Thr
    130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
            180                 185                 190

His His Cys Leu Ser Ala Arg Thr Ile Tyr Thr Phe Ser Val Pro Lys
        195                 200                 205

Tyr Ser Lys Phe Ser Lys Pro Thr Cys Phe Leu Leu Glu Val Pro Glu
    210                 215                 220

Ala Asn Trp Ala Phe Leu Val Leu Pro Ser Leu Leu Ile Leu Leu Leu
225                 230                 235                 240
```

```
Val Ile Ala Ala Gly Gly Val Ile Trp Lys Thr Leu Met Gly Asn Pro
                245                 250                 255

Trp Phe Gln Arg Ala Lys Met Pro Arg Ala Leu Asp Phe Ser Gly His
            260                 265                 270

Thr His Pro Val Ala Thr Phe Gln Pro Ser Arg Pro Glu Ser Val Asn
        275                 280                 285

Asp Leu Phe Leu Cys Pro Gln Lys Glu Leu Thr Arg Gly Val Arg Pro
    290                 295                 300

Thr Pro Arg Val Arg Ala Pro Ala Thr Gln Gln Thr Arg Trp Lys Lys
305                 310                 315                 320

Asp Leu Ala Glu Asp Glu Glu Glu Glu Asp Glu Glu Asp Thr Glu Asp
                325                 330                 335

Gly Val Ser Phe Gln Pro Tyr Ile Glu Pro Pro Ser Phe Leu Gly Gln
            340                 345                 350

Glu His Gln Ala Pro Gly His Ser Glu Ala Gly Gly Val Asp Ser Gly
        355                 360                 365

Arg Pro Arg Ala Pro Leu Val Pro Ser Glu Gly Ser Ser Ala Trp Asp
    370                 375                 380

Ser Ser Asp Arg Ser Trp Ala Ser Thr Val Asp Ser Ser Trp Asp Arg
385                 390                 395                 400

Ala Gly Ser Ser Gly Tyr Leu Ala Glu Lys Gly Pro Gly Gln Gly Pro
                405                 410                 415

Gly Gly Asp Gly His Gln Glu Ser Leu Pro Pro Pro Glu Phe Ser Lys
            420                 425                 430

Asp Ser Gly Phe Leu Glu Glu Leu Pro Glu Asp Asn Leu Ser Ser Trp
        435                 440                 445

Ala Thr Trp Gly Thr Leu Pro Pro Glu Pro Asn Leu Val Pro Gly Gly
    450                 455                 460

Pro Pro Val Ser Leu Gln Thr Leu Thr Phe Cys Trp Glu Ser Ser Pro
465                 470                 475                 480

Glu Glu Glu Glu Glu Ala Arg Glu Ser Glu Ile Glu Asp Ser Asp Ala
                485                 490                 495

Gly Ser Trp Gly Ala Glu Ser Thr Gln Arg Thr Glu Asp Arg Gly Arg
            500                 505                 510

Thr Leu Gly His Tyr Met Ala Arg
        515                 520


<210> SEQ ID NO 20
<211> LENGTH: 674
<212> TYPE: DNA
<213> ORGANISM: Homo sapiens
<220> FEATURE:
<221> NAME/KEY: CDS
<222> LOCATION: (1)...(633)

<400> SEQUENCE: 20

atg gcg ggg ccc gag cgc tgg ggc ccc ctg ctc ctg tgc ctg ctg cag       48
Met Ala Gly Pro Glu Arg Trp Gly Pro Leu Leu Leu Cys Leu Leu Gln
 1               5                  10                  15

gcc gct cca ggg agg ccc cgt ctg gcc cct ccc cag aat gtg acg ctg       96
Ala Ala Pro Gly Arg Pro Arg Leu Ala Pro Pro Gln Asn Val Thr Leu
             20                  25                  30

ctc tcc cag aac ttc agc gtg tac ctg aca tgg ctc cca ggg ctt ggc      144
Leu Ser Gln Asn Phe Ser Val Tyr Leu Thr Trp Leu Pro Gly Leu Gly
         35                  40                  45

aac ccc cag gat gtg acc tat ttt gtg gcc tat cag agc tct ccc acc      192
```

-continued

```
Asn Pro Gln Asp Val Thr Tyr Phe Val Ala Tyr Gln Ser Ser Pro Thr
     50                  55                  60

cgt aga cgg tgg cgc gaa gtg gaa gag tgt gcg gga acc aag gag ctg      240
Arg Arg Arg Trp Arg Glu Val Glu Glu Cys Ala Gly Thr Lys Glu Leu
 65                  70                  75                  80

cta tgt tct atg atg tgc ctg aag aaa cag gac ctg tac aac aag ttc      288
Leu Cys Ser Met Met Cys Leu Lys Lys Gln Asp Leu Tyr Asn Lys Phe
                 85                  90                  95

aag gga cgc gtg cgg acg gtt tct ccc agc tcc aag tcc ccc tgg gtg      336
Lys Gly Arg Val Arg Thr Val Ser Pro Ser Ser Lys Ser Pro Trp Val
            100                 105                 110

gag tcc gaa tac ctg gat tac ctt ttt gaa gtg gag ccg gcc cca cct      384
Glu Ser Glu Tyr Leu Asp Tyr Leu Phe Glu Val Glu Pro Ala Pro Pro
        115                 120                 125

gtc ctg gtg ctc acc cag acg gag gag atc ctg agt gcc aat gcc acg      432
Val Leu Val Leu Thr Gln Thr Glu Glu Ile Leu Ser Ala Asn Ala Thr
    130                 135                 140

tac cag ctg ccc ccc tgc atg ccc cca ctg gat ctg aag tat gag gtg      480
Tyr Gln Leu Pro Pro Cys Met Pro Pro Leu Asp Leu Lys Tyr Glu Val
145                 150                 155                 160

gca ttc tgg aag gag ggg gcc gga aac aag gtg gga agc tcc ttt cct      528
Ala Phe Trp Lys Glu Gly Ala Gly Asn Lys Val Gly Ser Ser Phe Pro
                165                 170                 175

gcc ccc agg cta ggc ccg ctc ctc cac ccc ttc tta ctc agg ttc ttc      576
Ala Pro Arg Leu Gly Pro Leu Leu His Pro Phe Leu Leu Arg Phe Phe
            180                 185                 190

tca ccc tcc cag cct gct cct gca ccc ctc ctc cag gaa gtc ttc cct      624
Ser Pro Ser Gln Pro Ala Pro Ala Pro Leu Leu Gln Glu Val Phe Pro
        195                 200                 205

gta cac tcc tgacttctgg cagtcagccc taataaaatc tgatcaaagt              673
Val His Ser
    210

a                                                                    674


<210> SEQ ID NO 21
<211> LENGTH: 211
<212> TYPE: PRT
<213> ORGANISM: Homo sapiens

<400> SEQUENCE: 21

Met Ala Gly Pro Glu Arg Trp Gly Pro Leu Leu Leu Cys Leu Leu Gln
 1               5                  10                  15

Ala Ala Pro Gly Arg Pro Arg Leu Ala Pro Pro Gln Asn Val Thr Leu
            20                  25                  30

Leu Ser Gln Asn Phe Ser Val Tyr Leu Thr Trp Leu Pro Gly Leu Gly
        35                  40                  45

Asn Pro Gln Asp Val Thr Tyr Phe Val Ala Tyr Gln Ser Ser Pro Thr
    50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95

Lys Gly Arg Val Arg Thr Val Ser Pro Ser Ser Lys Ser Pro Trp Val
            100                 105                 110

Glu Ser Glu Tyr Leu Asp Tyr Leu Phe Glu Val Glu Pro Ala Pro Pro
        115                 120                 125

Val Leu Val Leu Thr Gln Thr Glu Glu Ile Leu Ser Ala Asn Ala Thr
    130                 135                 140
```

-continued

```
Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Val Gly Ser Ser Phe Pro
                165                 170                 175

Ala Pro Arg Leu Gly Pro Leu Leu His Pro Phe Leu Leu Arg Phe Phe
            180                 185                 190

Ser Pro Ser Gln Pro Ala Pro Ala Pro Leu Leu Gln Glu Val Phe Pro
        195                 200                 205

Val His Ser
    210


<210> SEQ ID NO 22
<211> LENGTH: 1422
<212> TYPE: DNA
<213> ORGANISM: Artificial Sequence
<220> FEATURE:
<223> OTHER INFORMATION: Zcytor17-Fc4 fusion protein
<220> FEATURE:
<221> NAME/KEY: CDS
<222> LOCATION: (1)...(1422)

<400> SEQUENCE: 22

atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
 1               5                  10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga tcc agg ccc cgt ctg gcc cct ccc cag aat gtg acg ctg      144
Phe Arg Arg Ser Arg Pro Arg Leu Ala Pro Pro Gln Asn Val Thr Leu
        35                  40                  45

ctc tcc cag aac ttc agc gtg tac ctg aca tgg ctc cca ggg ctt ggc      192
Leu Ser Gln Asn Phe Ser Val Tyr Leu Thr Trp Leu Pro Gly Leu Gly
    50                  55                  60

aac ccc cag gat gtg acc tat ttt gtg gcc tat cag agc tct ccc acc      240
Asn Pro Gln Asp Val Thr Tyr Phe Val Ala Tyr Gln Ser Ser Pro Thr
 65                  70                  75                  80

cgt aga cgg tgg cgc gaa gtg gaa gag tgt gcg gga acc aag gag ctg      288
Arg Arg Arg Trp Arg Glu Val Glu Glu Cys Ala Gly Thr Lys Glu Leu
                85                  90                  95

cta tgt tct atg atg tgc ctg aag aaa cag gac ctg tac aac aag ttc      336
Leu Cys Ser Met Met Cys Leu Lys Lys Gln Asp Leu Tyr Asn Lys Phe
            100                 105                 110

aag gga cgc gtg cgg acg gtt tct ccc agc tcc aag tcc ccc tgg gtg      384
Lys Gly Arg Val Arg Thr Val Ser Pro Ser Ser Lys Ser Pro Trp Val
        115                 120                 125

gag tcc gaa tac ctg gat tac ctt ttt gaa gtg gag ccg gcc cca cct      432
Glu Ser Glu Tyr Leu Asp Tyr Leu Phe Glu Val Glu Pro Ala Pro Pro
    130                 135                 140

gtc ctg gtg ctc acc cag acg gag gag atc ctg agt gcc aat gcc acg      480
Val Leu Val Leu Thr Gln Thr Glu Glu Ile Leu Ser Ala Asn Ala Thr
145                 150                 155                 160

tac cag ctg ccc ccc tgc atg ccc cca ctg gat ctg aag tat gag gtg      528
Tyr Gln Leu Pro Pro Cys Met Pro Pro Leu Asp Leu Lys Tyr Glu Val
                165                 170                 175

gca ttc tgg aag gag ggg gcc gga aac aag acc cta ttt cca gtc act      576
Ala Phe Trp Lys Glu Gly Ala Gly Asn Lys Thr Leu Phe Pro Val Thr
            180                 185                 190

ccc cat ggc cag cca gtc cag atc act ctc cag cca gct gcc agc gaa      624
Pro His Gly Gln Pro Val Gln Ile Thr Leu Gln Pro Ala Ala Ser Glu
```

-continued

```
        195                 200                 205

cac cac tgc ctc agt gcc aga acc atc tac acg ttc agt gtc ccg aaa      672
His His Cys Leu Ser Ala Arg Thr Ile Tyr Thr Phe Ser Val Pro Lys
    210                 215                 220

tac agc aag ttc tct aag ccc acc tgc ttc ttg ctg gag gtc cca gaa      720
Tyr Ser Lys Phe Ser Lys Pro Thr Cys Phe Leu Leu Glu Val Pro Glu
225                 230                 235                 240

gcc aac tgg aga tct tca gac aaa act cac aca tgc cca ccg tgc cca      768
Ala Asn Trp Arg Ser Ser Asp Lys Thr His Thr Cys Pro Pro Cys Pro
                245                 250                 255

gca cct gaa gcc gag ggg gca ccg tca gtc ttc ctc ttc ccc cca aaa      816
Ala Pro Glu Ala Glu Gly Ala Pro Ser Val Phe Leu Phe Pro Pro Lys
            260                 265                 270

ccc aag gac acc ctc atg atc tcc cgg acc cct gag gtc aca tgc gtg      864
Pro Lys Asp Thr Leu Met Ile Ser Arg Thr Pro Glu Val Thr Cys Val
        275                 280                 285

gtg gtg gac gtg agc cac gaa gac cct gag gtc aag ttc aac tgg tac      912
Val Val Asp Val Ser His Glu Asp Pro Glu Val Lys Phe Asn Trp Tyr
    290                 295                 300

gtg gac ggc gtg gag gtg cat aat gcc aag aca aag ccg cgg gag gag      960
Val Asp Gly Val Glu Val His Asn Ala Lys Thr Lys Pro Arg Glu Glu
305                 310                 315                 320

cag tac aac agc acg tac cgt gtg gtc agc gtc ctc acc gtc ctg cac     1008
Gln Tyr Asn Ser Thr Tyr Arg Val Val Ser Val Leu Thr Val Leu His
                325                 330                 335

cag gac tgg ctg aat ggc aag gag tac aag tgc aag gtc tcc aac aaa     1056
Gln Asp Trp Leu Asn Gly Lys Glu Tyr Lys Cys Lys Val Ser Asn Lys
            340                 345                 350

gcc ctc cca tcc tcc atc gag aaa acc atc tcc aaa gcc aaa ggg cag     1104
Ala Leu Pro Ser Ser Ile Glu Lys Thr Ile Ser Lys Ala Lys Gly Gln
        355                 360                 365

ccc cga gaa cca cag gtg tac acc ctg ccc cca tcc cgg gat gag ctg     1152
Pro Arg Glu Pro Gln Val Tyr Thr Leu Pro Pro Ser Arg Asp Glu Leu
    370                 375                 380

acc aag aac cag gtc agc ctg acc tgc ctg gtc aaa ggc ttc tat ccc     1200
Thr Lys Asn Gln Val Ser Leu Thr Cys Leu Val Lys Gly Phe Tyr Pro
385                 390                 395                 400

agc gac atc gcc gtg gag tgg gag agc aat ggg cag ccg gag aac aac     1248
Ser Asp Ile Ala Val Glu Trp Glu Ser Asn Gly Gln Pro Glu Asn Asn
                405                 410                 415

tac aag acc acg cct ccc gtg ctg gac tcc gac ggc tcc ttc ttc ctc     1296
Tyr Lys Thr Thr Pro Pro Val Leu Asp Ser Asp Gly Ser Phe Phe Leu
            420                 425                 430

tac agc aag ctc acc gtg gac aag agc agg tgg cag cag ggg aac gtc     1344
Tyr Ser Lys Leu Thr Val Asp Lys Ser Arg Trp Gln Gln Gly Asn Val
        435                 440                 445

ttc tca tgc tcc gtg atg cat gag gct ctg cac aac cac tac acg cag     1392
Phe Ser Cys Ser Val Met His Glu Ala Leu His Asn His Tyr Thr Gln
    450                 455                 460

aag agc ctc tcc ctg tct ccg ggt aaa taa                             1422
Lys Ser Leu Ser Leu Ser Pro Gly Lys  *
465                 470
```

<210> SEQ ID NO 23
<211> LENGTH: 473
<212> TYPE: PRT
<213> ORGANISM: Artificial Sequence
<220> FEATURE:
<223> OTHER INFORMATION: Zcytor17-Fc4 fusion protein

<400> SEQUENCE: 23

-continued

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
            20                  25                  30

Phe Arg Arg Ser Arg Pro Arg Leu Ala Pro Pro Gln Asn Val Thr Leu
        35                  40                  45

Leu Ser Gln Asn Phe Ser Val Tyr Leu Thr Trp Leu Pro Gly Leu Gly
    50                  55                  60

Asn Pro Gln Asp Val Thr Tyr Phe Val Ala Tyr Gln Ser Ser Pro Thr
65                  70                  75                  80

Arg Arg Arg Trp Arg Glu Val Glu Glu Cys Ala Gly Thr Lys Glu Leu
                85                  90                  95

Leu Cys Ser Met Met Cys Leu Lys Lys Gln Asp Leu Tyr Asn Lys Phe
            100                 105                 110

Lys Gly Arg Val Arg Thr Val Ser Pro Ser Ser Lys Ser Pro Trp Val
        115                 120                 125

Glu Ser Glu Tyr Leu Asp Tyr Leu Phe Glu Val Glu Pro Ala Pro Pro
    130                 135                 140

Val Leu Val Leu Thr Gln Thr Glu Glu Ile Leu Ser Ala Asn Ala Thr
145                 150                 155                 160

Tyr Gln Leu Pro Pro Cys Met Pro Pro Leu Asp Leu Lys Tyr Glu Val
                165                 170                 175

Ala Phe Trp Lys Glu Gly Ala Gly Asn Lys Thr Leu Phe Pro Val Thr
            180                 185                 190

Pro His Gly Gln Pro Val Gln Ile Thr Leu Gln Pro Ala Ala Ser Glu
        195                 200                 205

His His Cys Leu Ser Ala Arg Thr Ile Tyr Thr Phe Ser Val Pro Lys
    210                 215                 220

Tyr Ser Lys Phe Ser Lys Pro Thr Cys Phe Leu Leu Glu Val Pro Glu
225                 230                 235                 240

Ala Asn Trp Arg Ser Ser Asp Lys Thr His Thr Cys Pro Pro Cys Pro
                245                 250                 255

Ala Pro Glu Ala Glu Gly Ala Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ser Ser Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415
```

-continued

```
Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 24
<211> LENGTH: 28
<212> TYPE: DNA
<213> ORGANISM: Artificial Sequence
<220> FEATURE:
<223> OTHER INFORMATION: Oligonucleotide primer ZC37967

<400> SEQUENCE: 24
gcggatccag gccccgtctg gcccctcc 28

<210> SEQ ID NO 25
<211> LENGTH: 30
<212> TYPE: DNA
<213> ORGANISM: Artificial Sequence
<220> FEATURE:
<223> OTHER INFORMATION: Oligonucleotide primer ZC37972

<400> SEQUENCE: 25
gcagatctcc agttggcttc tgggacctcc 30

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide primer ZC37685

<400> SEQUENCE: 26
ccagccctac attgaaccac ctt 23

<210> SEQ ID NO 27
<211> LENGTH: 22
<212> TYPE: DNA
<213> ORGANISM: Artificial Sequence
<220> FEATURE:
<223> OTHER INFORMATION: Oligonucleotide primer ZC37681

<400> SEQUENCE: 27
cctcgcctcc tcttcctcct ca 22

<210> SEQ ID NO 28
<211> LENGTH: 1560
<212> TYPE: DNA
<213> ORGANISM: Artificial Sequence
<220> FEATURE:
<223> OTHER INFORMATION: Degenerate Polynucleotide seuquence of SEQ ID NO:19
<220> FEATURE:
<221> NAME/KEY: misc_feature
<222> LOCATION: (1)...(1560)
<223> OTHER INFORMATION: n = A,T,C or G

<400> SEQUENCE: 28
atggcnggnc cngarmgntg gggnccnytn ytnytntgyy tnytncargc ngcnccnggn 60
mgnccnmgny tngcnccncc ncaraaygtn acnytnytnw sncaraaytt ywsngtntay 120

-continued

```
ytnacntggy tnccnggnyt nggnaayccn cargaygtna cntayttygt ngcntaycar    180

wsnwsnccna cnmgnmgnmg ntggmgngar gtngargart gygcnggnac naargarytn    240

ytntgywsna tgatgtgyyt naaraarcar gayytntaya ayaarttyaa rggnmgngtn    300

mgnacngtnw snccnwsnws naarwsnccn tgggtngarw sngartayyt ngaytayytn    360

ttygargtng arccngcncc nccngtnytn gtnytnacnc aracngarga rathytnwsn    420

gcnaaygcna cntaycaryt nccnccntgy atgccnccny tngayytnaa rtaygargtn    480

gcnttytgga argarggngc nggnaayaar acnytnttyc cngtnacncc ncayggncar    540

ccngtncara thacnytnca rccngcngcn wsngarcayc aytgyytnws ngcnmgnacn    600

athtayacnt tywsngtncc naartaywsn aarttywsna arccnacntg yttyytnytn    660

gargtnccng argcnaaytg ggcnttyytn gtnytnccnw snytnytnat hytnytnytn    720

gtnathgcng cnggnggngt nathtggaar acnytnatgg gnaayccntg gttycarmgn    780

gcnaaratgc cnmgngcnyt ngayttywsn ggncayacnc ayccngtngc nacnttycar    840

ccnwsnmgnc cngarwsngt naaygayytn ttyytntgyc cncaraarga rytnacnmgn    900

ggngtnmgnc cnacnccnmg ngtnmgngcn ccngcnacnc arcaracnmg ntggaaraar    960

gayytngcng argaygarga rgargargay gargargaya cngargaygg ngtnwsntty   1020

carccntaya thgarccncc nwsnttyytn ggncargarc aycargcncc nggncaywsn   1080

gargcnggng gngtngayws nggnmgnccn mgngcnccny tngtnccnws ngarggnwsn   1140

wsngcntggg aywsnwsnga ymgnwsntgg gcnwsnacng tngaywsnws ntgggaymgn   1200

gcnggnwsnw snggntayyt ngcngaraar ggnccnggnc arggnccngg nggngayggn   1260

caycargarw snytnccncc nccngartty wsnaargayw snggnttyyt ngargarytn   1320

ccngargaya ayytnwsnws ntgggcnacn tggggnacny tnccnccnga rccnaayytn   1380

gtnccnggng gnccnccngt nwsnytncar acnytnacnt tytgytggga rwsnwsnccn   1440

gargargarg argargcnmg ngarwsngar athgargayw sngaygcngg nwsntggggn   1500

gcngarwsna cncarmgnac ngargaymgn ggnmgnacny tnggncayta yatggcnmgn   1560
```

```
<210> SEQ ID NO 29
<211> LENGTH: 633
<212> TYPE: DNA
<213> ORGANISM: Artificial Sequence
<220> FEATURE:
<223> OTHER INFORMATION: Degenerate polynucleotide sequence of
      SEQ ID NO:21
<220> FEATURE:
<221> NAME/KEY: misc_feature
<222> LOCATION: (1)...(633)
<223> OTHER INFORMATION: n = A,T,C or G

<400> SEQUENCE: 29

atggcnggnc cngarmgntg gggnccnytn ytnytntgyy tnytncargc ngcnccnggn     60

mgnccnmgny tngcnccncc ncaraaygtn acnytnytnw sncaraaytt ywsngtntay    120

ytnacntggy tnccnggnyt nggnaayccn cargaygtna cntayttygt ngcntaycar    180

wsnwsnccna cnmgnmgnmg ntggmgngar gtngargart gygcnggnac naargarytn    240

ytntgywsna tgatgtgyyt naaraarcar gayytntaya ayaarttyaa rggnmgngtn    300

mgnacngtnw snccnwsnws naarwsnccn tgggtngarw sngartayyt ngaytayytn    360

ttygargtng arccngcncc nccngtnytn gtnytnacnc aracngarga rathytnwsn    420

gcnaaygcna cntaycaryt nccnccntgy atgccnccny tngayytnaa rtaygargtn    480
```

-continued

```
gcnttytgga argarggngc nggnaayaar gtnggnwsnw snttyccngc nccnmgnytn    540

ggnccnytny tncayccntt yytnytnmgn ttyttywsnc cnwsncarcc ngcnccngcn    600

ccnytnytnc argargtntt yccngtncay wsn                                 633


<210> SEQ ID NO 30
<211> LENGTH: 64
<212> TYPE: DNA
<213> ORGANISM: Artificial Sequence
<220> FEATURE:
<223> OTHER INFORMATION: Oligonucleotide Primer ZC39204

<400> SEQUENCE: 30

tcaccacgcg aattcggtac cgctggttcc gcgtggatcc aggccccgtc tggcccctcc     60

ccag                                                                  64


<210> SEQ ID NO 31
<211> LENGTH: 64
<212> TYPE: DNA
<213> ORGANISM: Artificial Sequence
<220> FEATURE:
<223> OTHER INFORMATION: Oligonucleotide Primer ZC39205

<400> SEQUENCE: 31

tctgtatcag gctgaaaatc ttatctcatc cgccaaaaca ccagttggct tctgggacct     60

ccag                                                                  64


<210> SEQ ID NO 32
<211> LENGTH: 1922
<212> TYPE: DNA
<213> ORGANISM: Artificial Sequence
<220> FEATURE:
<223> OTHER INFORMATION: MBP-human zcytoR19 fusion protein
      polynucleotide sequence
<220> FEATURE:
<221> NAME/KEY: CDS
<222> LOCATION: (123)...(1922)

<400> SEQUENCE: 32

ttgacaatta atcatcggct cgtataatgt gtggaattgt gagcggataa caatttcaca     60

caggaaacag ccagtccgtt taggtgtttt cacgagcact tcaccaacaa ggaccataga    120

tt atg aaa act gaa gaa ggt aaa ctg gta atc tgg att aac ggc gat      167
   Met Lys Thr Glu Glu Gly Lys Leu Val Ile Trp Ile Asn Gly Asp
    1               5                  10                  15

aaa ggc tat aac ggt ctc gct gaa gtc ggt aag aaa ttc gag aaa gat      215
Lys Gly Tyr Asn Gly Leu Ala Glu Val Gly Lys Lys Phe Glu Lys Asp
                20                  25                  30

acc gga att aaa gtc acc gtt gag cat ccg gat aaa ctg gaa gag aaa      263
Thr Gly Ile Lys Val Thr Val Glu His Pro Asp Lys Leu Glu Glu Lys
            35                  40                  45

ttc cca cag gtt gcg gca act ggc gat ggc cct gac att atc ttc tgg      311
Phe Pro Gln Val Ala Ala Thr Gly Asp Gly Pro Asp Ile Ile Phe Trp
        50                  55                  60

gca cac gac cgc ttt ggt ggc tac gct caa tct ggc ctg ttg gct gaa      359
Ala His Asp Arg Phe Gly Gly Tyr Ala Gln Ser Gly Leu Leu Ala Glu
    65                  70                  75

atc acc ccg gac aaa gcg ttc cag gac aag ctg tat ccg ttt acc tgg      407
Ile Thr Pro Asp Lys Ala Phe Gln Asp Lys Leu Tyr Pro Phe Thr Trp
 80                  85                  90                  95

gat gcc gta cgt tac aac ggc aag ctg att gct tac ccg atc gct gtt      455
Asp Ala Val Arg Tyr Asn Gly Lys Leu Ile Ala Tyr Pro Ile Ala Val
                100                 105                 110
```

-continued

```
gaa gcg tta tcg ctg att tat aac aaa gat ctg ctg ccg aac ccg cca      503
Glu Ala Leu Ser Leu Ile Tyr Asn Lys Asp Leu Leu Pro Asn Pro Pro
            115                 120                 125

aaa acc tgg gaa gag atc ccg gcg ctg gat aaa gaa ctg aaa gcg aaa      551
Lys Thr Trp Glu Glu Ile Pro Ala Leu Asp Lys Glu Leu Lys Ala Lys
        130                 135                 140

ggt aag agc gcg ctg atg ttc aac ctg caa gaa ccg tac ttc acc tgg      599
Gly Lys Ser Ala Leu Met Phe Asn Leu Gln Glu Pro Tyr Phe Thr Trp
    145                 150                 155

ccg ctg att gct gct gac ggg ggt tat gcg ttc aag tat gaa aac ggc      647
Pro Leu Ile Ala Ala Asp Gly Gly Tyr Ala Phe Lys Tyr Glu Asn Gly
160                 165                 170                 175

aag tac gac att aaa gac gtg ggc gtg gat aac gct ggc gcg aaa gcg      695
Lys Tyr Asp Ile Lys Asp Val Gly Val Asp Asn Ala Gly Ala Lys Ala
                180                 185                 190

ggt ctg acc ttc ctg gtt gac ctg att aaa aac aaa cac atg aat gca      743
Gly Leu Thr Phe Leu Val Asp Leu Ile Lys Asn Lys His Met Asn Ala
            195                 200                 205

gac acc gat tac tcc atc gca gaa gct gcc ttt aat aaa ggc gaa aca      791
Asp Thr Asp Tyr Ser Ile Ala Glu Ala Ala Phe Asn Lys Gly Glu Thr
        210                 215                 220

gcg atg acc atc aac ggc ccg tgg gca tgg tcc aac atc gac acc agc      839
Ala Met Thr Ile Asn Gly Pro Trp Ala Trp Ser Asn Ile Asp Thr Ser
    225                 230                 235

aaa gtg aat tat ggt gta acg gta ctg ccg acc ttc aag ggt caa cca      887
Lys Val Asn Tyr Gly Val Thr Val Leu Pro Thr Phe Lys Gly Gln Pro
240                 245                 250                 255

tcc aaa ccg ttc gtt ggc gtg ctg agc gca ggt att aac gcc gcc agt      935
Ser Lys Pro Phe Val Gly Val Leu Ser Ala Gly Ile Asn Ala Ala Ser
                260                 265                 270

ccg aac aaa gag ctg gca aaa gag ttc ctc gaa aac tat ctg ctg act      983
Pro Asn Lys Glu Leu Ala Lys Glu Phe Leu Glu Asn Tyr Leu Leu Thr
            275                 280                 285

gat gaa ggt ctg gaa gcg gtt aat aaa gac aaa ccg ctg ggt gcc gta     1031
Asp Glu Gly Leu Glu Ala Val Asn Lys Asp Lys Pro Leu Gly Ala Val
        290                 295                 300

gcg ctg aag tct tac gag gaa gag ttg gcg aaa gat cca cgt att gcc     1079
Ala Leu Lys Ser Tyr Glu Glu Glu Leu Ala Lys Asp Pro Arg Ile Ala
    305                 310                 315

gcc acc atg gaa aac gcc cag aaa ggt gaa atc atg ccg aac atc ccg     1127
Ala Thr Met Glu Asn Ala Gln Lys Gly Glu Ile Met Pro Asn Ile Pro
320                 325                 330                 335

cag atg tcc gct ttc tgg tat gcc gtg cgt act gcg gtg atc aac gcc     1175
Gln Met Ser Ala Phe Trp Tyr Ala Val Arg Thr Ala Val Ile Asn Ala
                340                 345                 350

gcc agc ggt cgt cag act gtc gat gaa gcc ctg aaa gac gcg cag act     1223
Ala Ser Gly Arg Gln Thr Val Asp Glu Ala Leu Lys Asp Ala Gln Thr
            355                 360                 365

aat tcg agc tcc cac cat cac cat cac cac gcg aat tcg gta ccg ctg     1271
Asn Ser Ser Ser His His His His His His Ala Asn Ser Val Pro Leu
        370                 375                 380

gtt ccg cgt gga tcc agg ccc cgt ctg gcc cct ccc cag aat gtg acg     1319
Val Pro Arg Gly Ser Arg Pro Arg Leu Ala Pro Pro Gln Asn Val Thr
    385                 390                 395

ctg ctc tcc cag aac ttc agc gtg tac ctg aca tgg ctc cca ggg ctt     1367
Leu Leu Ser Gln Asn Phe Ser Val Tyr Leu Thr Trp Leu Pro Gly Leu
400                 405                 410                 415

ggc aac ccc cag gat gtg acc tat ttt gtg gcc tat cag agc tct ccc     1415
Gly Asn Pro Gln Asp Val Thr Tyr Phe Val Ala Tyr Gln Ser Ser Pro
```

-continued

```
            420                 425                 430

acc cgt aga cgg tgg cgc gaa gtg gaa gag tgt gcg gga acc aag gag     1463
Thr Arg Arg Arg Trp Arg Glu Val Glu Glu Cys Ala Gly Thr Lys Glu
            435                 440                 445

ctg cta tgt tct atg atg tgc ctg aag aaa cag gac ctg tac aac aag     1511
Leu Leu Cys Ser Met Met Cys Leu Lys Lys Gln Asp Leu Tyr Asn Lys
        450                 455                 460

ttc aag gga cgc gtg cgg acg gtt tct ccc agc tcc aag tcc ccc tgg     1559
Phe Lys Gly Arg Val Arg Thr Val Ser Pro Ser Ser Lys Ser Pro Trp
    465                 470                 475

gtg gag tcc gaa tac ctg gat tac ctt ttt gaa gtg gag ccg gcc cca     1607
Val Glu Ser Glu Tyr Leu Asp Tyr Leu Phe Glu Val Glu Pro Ala Pro
480                 485                 490                 495

cct gtc ctg gtg ctc acc cag acg gag gag atc ctg agt gcc aat gcc     1655
Pro Val Leu Val Leu Thr Gln Thr Glu Glu Ile Leu Ser Ala Asn Ala
                500                 505                 510

acg tac cag ctg ccc ccc tgc atg ccc cca ctg gat ctg aag tat gag     1703
Thr Tyr Gln Leu Pro Pro Cys Met Pro Pro Leu Asp Leu Lys Tyr Glu
            515                 520                 525

gtg gca ttc tgg aag gag ggg gcc gga aac aag acc cta ttt cca gtc     1751
Val Ala Phe Trp Lys Glu Gly Ala Gly Asn Lys Thr Leu Phe Pro Val
        530                 535                 540

act ccc cat ggc cag cca gtc cag atc act ctc cag cca gct gcc agc     1799
Thr Pro His Gly Gln Pro Val Gln Ile Thr Leu Gln Pro Ala Ala Ser
    545                 550                 555

gaa cac cac tgc ctc agt gcc aga acc atc tac acg ttc agt gtc ccg     1847
Glu His His Cys Leu Ser Ala Arg Thr Ile Tyr Thr Phe Ser Val Pro
560                 565                 570                 575

aaa tac agc aag ttc tct aag ccc acc tgc ttc ttg ctg gag gtc cca     1895
Lys Tyr Ser Lys Phe Ser Lys Pro Thr Cys Phe Leu Leu Glu Val Pro
                580                 585                 590

gaa gcc aac tgg tgt ttt ggc gga tga                                 1922
Glu Ala Asn Trp Cys Phe Gly Gly  *
            595
```

<210> SEQ ID NO 33
<211> LENGTH: 599
<212> TYPE: PRT
<213> ORGANISM: Artificial Sequence
<220> FEATURE:
<223> OTHER INFORMATION: MBP-human zcytoR19 fusion protein polypeptide sequence

<400> SEQUENCE: 33

```
Met Lys Thr Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
```

-continued

```
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser His His His His His His Ala Asn Ser Val Pro Leu Val
    370                 375                 380

Pro Arg Gly Ser Arg Pro Arg Leu Ala Pro Pro Gln Asn Val Thr Leu
385                 390                 395                 400

Leu Ser Gln Asn Phe Ser Val Tyr Leu Thr Trp Leu Pro Gly Leu Gly
                405                 410                 415

Asn Pro Gln Asp Val Thr Tyr Phe Val Ala Tyr Gln Ser Ser Pro Thr
            420                 425                 430

Arg Arg Arg Trp Arg Glu Val Glu Glu Cys Ala Gly Thr Lys Glu Leu
        435                 440                 445

Leu Cys Ser Met Met Cys Leu Lys Lys Gln Asp Leu Tyr Asn Lys Phe
    450                 455                 460

Lys Gly Arg Val Arg Thr Val Ser Pro Ser Ser Lys Ser Pro Trp Val
465                 470                 475                 480

Glu Ser Glu Tyr Leu Asp Tyr Leu Phe Glu Val Glu Pro Ala Pro Pro
                485                 490                 495

Val Leu Val Leu Thr Gln Thr Glu Glu Ile Leu Ser Ala Asn Ala Thr
            500                 505                 510

Tyr Gln Leu Pro Pro Cys Met Pro Pro Leu Asp Leu Lys Tyr Glu Val
        515                 520                 525

Ala Phe Trp Lys Glu Gly Ala Gly Asn Lys Thr Leu Phe Pro Val Thr
    530                 535                 540
```

```
Pro His Gly Gln Pro Val Gln Ile Thr Leu Gln Pro Ala Ala Ser Glu
545                 550                 555                 560

His His Cys Leu Ser Ala Arg Thr Ile Tyr Thr Phe Ser Val Pro Lys
                565                 570                 575

Tyr Ser Lys Phe Ser Lys Pro Thr Cys Phe Leu Leu Glu Val Pro Glu
            580                 585                 590

Ala Asn Trp Cys Phe Gly Gly
        595


<210> SEQ ID NO 34
<211> LENGTH: 20
<212> TYPE: PRT
<213> ORGANISM: Homo sapiens
<220> FEATURE:
<221> NAME/KEY: VARIANT
<222> LOCATION: (1)...(20)
<223> OTHER INFORMATION: Xaa = Any Amino Acid

<400> SEQUENCE: 34

Ser Arg Pro Arg Leu Ala Pro Pro Gln Xaa Val Thr Leu Leu Ser Gln
 1               5                  10                  15

Asn Phe Ser Val
            20


<210> SEQ ID NO 35
<211> LENGTH: 24
<212> TYPE: DNA
<213> ORGANISM: Artificial Sequence
<220> FEATURE:
<223> OTHER INFORMATION: Oligonucleotide primer ZC40285

<400> SEQUENCE: 35

gccccagcca cccaacagac aaga                                            24


<210> SEQ ID NO 36
<211> LENGTH: 24
<212> TYPE: DNA
<213> ORGANISM: Artificial Sequence
<220> FEATURE:
<223> OTHER INFORMATION: Oligonucleotide primer ZC40286

<400> SEQUENCE: 36

ccaggtggcc caggaggaga ggtt                                            24


<210> SEQ ID NO 37
<211> LENGTH: 24
<212> TYPE: DNA
<213> ORGANISM: Artificial Sequence
<220> FEATURE:
<223> OTHER INFORMATION: Oligonucleotide primer ZC39128

<400> SEQUENCE: 37

ggcatggaag ataatgaaag gaaa                                            24


<210> SEQ ID NO 38
<211> LENGTH: 24
<212> TYPE: DNA
<213> ORGANISM: Artificial Sequence
<220> FEATURE:
<223> OTHER INFORMATION: Oligonucleotide primer ZC39129

<400> SEQUENCE: 38

gccgtcactc ccaactgggg atgt                                            24
```

<210> SEQ ID NO 39
<211> LENGTH: 25
<212> TYPE: DNA
<213> ORGANISM: Artificial Sequence
<220> FEATURE:
<223> OTHER INFORMATION: Oligonucleotide primer ZC40784

<400> SEQUENCE: 39
ggatagtgtt ttgagtttct gtgga 25

<210> SEQ ID NO 40
<211> LENGTH: 25
<212> TYPE: DNA
<213> ORGANISM: Artificial Sequence
<220> FEATURE:
<223> OTHER INFORMATION: Oligonucleotide primer ZC40785

<400> SEQUENCE: 40
accaggagtt caaggttaac cttgg 25

<210> SEQ ID NO 41
<211> LENGTH: 24
<212> TYPE: DNA
<213> ORGANISM: Artificial Sequence
<220> FEATURE:
<223> OTHER INFORMATION: Oligonucleotide primer ZC40786

<400> SEQUENCE: 41
gggaattcct gcagaaactc agta 24

<210> SEQ ID NO 42
<211> LENGTH: 24
<212> TYPE: DNA
<213> ORGANISM: Artificial Sequence
<220> FEATURE:
<223> OTHER INFORMATION: Oligonucleotide primer ZC40787

<400> SEQUENCE: 42
cccttcctgc tcctttgact gcgt 24

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide primer ZC39408

<400> SEQUENCE: 43
gcccagctgc atcttcctag aggc 24

<210> SEQ ID NO 44
<211> LENGTH: 25
<212> TYPE: DNA
<213> ORGANISM: Artificial Sequence
<220> FEATURE:
<223> OTHER INFORMATION: Oligonucleotide primer ZC39409

<400> SEQUENCE: 44
gggcattgcc aggacagctc ttttg 25

<210> SEQ ID NO 45
<211> LENGTH: 121
<212> TYPE: DNA
<213> ORGANISM: Artificial Sequence
<220> FEATURE:
<223> OTHER INFORMATION: forward zcytor19 knockout oligonucleotide -continued

<400> SEQUENCE: 45

```
cacctgccgc ccaggggcct tgcggcgggc ggcggggacc ccagggaccg aaggccatag     60

cggccggccc ctaggatccg aattctagaa gctttgtgtc tcaaaatctc tgatgttaca     20

t                                                                     21
```

<210> SEQ ID NO 46
<211> LENGTH: 125
<212> TYPE: DNA
<213> ORGANISM: Artificial Sequence
<220> FEATURE:
<223> OTHER INFORMATION: reverse zcytor19 knockout oligonucleotide

<400> SEQUENCE: 46

```
ggctggtccc ctgcaagagt agcaagcgct tcttcagcat ccggacttac ggcctcgctg     60

gccggcgcgc ctaggaattc tctagaggat ccaagctttt agaaaaactc atcgagcatc     20

aaatg                                                                 25
```

<210> SEQ ID NO 47
<211> LENGTH: 22
<212> TYPE: DNA
<213> ORGANISM: Artificial Sequence
<220> FEATURE:
<223> OTHER INFORMATION: Oligonucleotide primer ZC38481

<400> SEQUENCE: 47

```
cctccttcca gaatgccacc tc                                              22
```

<210> SEQ ID NO 48
<211> LENGTH: 25
<212> TYPE: DNA
<213> ORGANISM: Artificial Sequence
<220> FEATURE:
<223> OTHER INFORMATION: Oligonucleotide primer ZC38626

<400> SEQUENCE: 48

```
ctgctatgtt ctatgatgtg cctga                                           25
```

<210> SEQ ID NO 49
<211> LENGTH: 22
<212> TYPE: DNA
<213> ORGANISM: Artificial Sequence
<220> FEATURE:
<223> OTHER INFORMATION: Oligonucleotide primer ZC38706

<400> SEQUENCE: 49

```
ggaagataat gaaaggaaac cc                                              22
```

<210> SEQ ID NO 50
<211> LENGTH: 21
<212> TYPE: DNA
<213> ORGANISM: Artificial Sequence
<220> FEATURE:
<223> OTHER INFORMATION: Oligonucleotide primer ZC38711

<400> SEQUENCE: 50

```
tatgaggagt cccctgtgct g                                               21
```

POLYNUCLEOTIDES ENCODING CYTOKINE RECEPTOR ZCYTOR19

REFERENCE TO RELATED APPLICATIONS

This application is a continuation of U.S. application Ser. No. 11/165,141 filed Jun. 23, 2005, now abandoned which is a continuation of U.S. application Ser. No. 09/995,898, filed Nov. 28, 2001, now abandoned, both of which are herein incorporated by reference. U.S. application Ser. No. 09/995, 898 claims the benefit of U.S. Provisional Application 60/253,561, filed on Nov. 28, 2000, and Provisional Application U.S. 60/267,211, filed on Feb. 7, 2001.

BACKGROUND OF THE INVENTION

Hormones and polypeptide growth factors control proliferation and differentiation of cells of multicellular organisms. These diffusible molecules allow cells to communicate with each other and act in concert to form cells and organs, and to repair damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the transcription factors. Of particular interest are receptors for cytokines, molecules that promote the proliferation and/or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

The demonstrated in vivo activities of these cytokines illustrate the enormous clinical potential of, and need for, other cytokines, cytokine agonists, and cytokine antagonists. The present invention addresses these needs by providing new a hematopoietic cytokine receptor, as well as related compositions and methods.

The present invention provides such polypeptides for these and other uses that should be apparent to those skilled in the art from the teachings herein.

DESCRIPTION OF THE INVENTION

These and other aspects of the invention will become evident upon reference to the following detailed description of the invention.

Within one aspect, the present invention provides an isolated polynucleotide that encodes a polypeptide comprising an amino acid sequence selected from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:2 from amino acid number 250 (Lys) to amino acid number 491 (Arg); (e) the amino acid sequence as shown in SEQ ID NO:19 from amino acid number 250 (Lys) to 520 (Arg); (f) the amino acid sequence as shown in SEQ ID NO:2 from amino acid number 21 (Arg) to amino acid number 491 (Arg); (g) the amino acid sequence as shown in SEQ ID NO:19 from amino acid number 21 (Arg) to amino acid number 520 (Arg); (h) the amino acid sequence as shown in SEQ ID NO:2 from amino acid number 1 (Met) to amino acid number 491 (Arg); (i) the amino acid sequence as shown in SEQ ID NO:19 from amino acid number 1 (Met) to amino acid number 520 (Arg); (j) the amino acid sequence as shown in SEQ ID NO:21 from amino acid number 21 (Arg) to amino acid number 163 (Trp); (k) the amino acid sequence as shown in SEQ ID NO:21 from amino acid number 21 (Arg) to amino acid number 211 (Ser); and (l) the amino acid sequence as shown in SEQ ID NO:21 from amino acid number 1 (Met) to amino acid number 211 (Ser). In one embodiment, the isolated polynucleotide described above comprises a polynucleotide sequence selected from the group consisting of: (a) a polynucleotide comprising a nucleotide sequence as shown in SEQ ID NO:1 from nucleotide 61 to nucleotide 669; (b) a polynucleotide comprising a nucleotide sequence as shown in SEQ ID NO:1 from nucleotide 61 to 678; (c) a polynucleotide comprising a nucleotide sequence as shown in SEQ ID NO:1 from nucleotide 61 to nucleotide 747; (d) a polynucleotide comprising a nucleotide sequence as shown in SEQ ID NO:1 from nucleotide 748 to nucleotide 1473; (e) a polynucleotide comprising a nucleotide sequence as shown in SEQ ID NO:18 from nucleotide 748 to nucleotide 1560; (f) a polynucleotide comprising a nucleotide sequence as shown in SEQ ID NO:1 from nucleotide 61 to nucleotide 1473; (g) a polynucleotide comprising a nucleotide sequence as shown in SEQ ID NO:18 from nucleotide 61 to nucleotide 1560; (h) a polynucleotide comprising a nucleotide sequence as shown in SEQ ID NO:1 from nucleotide 1 to nucleotide 1473; (i) a polynucleotide comprising a nucleotide sequence as shown in SEQ ID NO:18 from nucleotide 1 to nucleotide 1560; (j) a polynucleotide comprising a nucleotide sequence as shown in SEQ ID NO:20 from nucleotide 61 to nucleotide 489; (k) a polynucleotide comprising a nucleotide sequence as shown in SEQ ID NO:20 from nucleotide 61 to nucleotide 633; and (l) a polynucleotide comprising a nucleotide sequence as shown in SEQ ID NO:20 from nucleotide 1 to nucleotide 633. In another embodiment, the isolated polynucleotide is as described above, wherein the polynucleotide encodes a polypeptide that further comprises a transmembrane domain consisting of residues 227 (Trp) to 249 (Trp) of SEQ ID NO:2. In another embodiment, the isolated polynucleotide is as described above, wherein the polynucleotide encodes a polypeptide that further comprises an intracellular domain consisting of residues 250 (Lys) to 491 (Arg) of SEQ ID NO:2, or 250 (Lys) to 520 (Arg) of SEQ ID NO:19. In another embodiment, the isolated polynucleotide is as described above, wherein the polypeptide encoded by the polynucleotide has activity as measured by cell proliferation, activation of transcription of a reporter gene, or wherein the polypeptide encoded by the polynucleotide further binds to an antibody, wherein the antibody is raised to a polypeptide comprising a sequence of amino acids from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:2 from amino acid number 250 (Lys) to amino acid number 491 (Arg); (e) the amino acid sequence as shown in SEQ ID NO:19 from amino acid number 250 (Lys) to 520 (Arg); (f) the amino acid sequence as shown in SEQ ID NO:2 from amino acid number 21 (Arg) to amino acid number 491 (Arg); (g) the amino acid sequence as shown in SEQ ID NO:19 from amino acid number 21 (Arg) to amino acid number 520 (Arg); (h) the amino acid sequence as shown in SEQ ID NO:2 from amino acid number 1 (Met) to amino acid number 491 (Arg); (i) the amino acid sequence as shown in SEQ ID NO:19 from amino acid number 1 (Met) to amino acid number 520 (Arg); (j) the amino acid sequence as shown in SEQ ID NO:21 from amino acid number 21 (Arg) to amino acid number 163 (Trp); (k) the amino acid sequence as shown in SEQ ID NO:21 from amino acid number 21 (Arg) to amino acid number 211 (Ser); and (l) the amino acid sequence as shown in SEQ ID NO:21 from amino acid number 1 (Met) to amino acid number 211 (Ser); and wherein the binding of the antibody to the isolated polypeptide is measured by a biological or biochemical assay including radioimmunoassay, radioimmuno-precipitation, Western blot, or enzyme-linked immunosorbent assay.

Within a second aspect, the present invention provides an expression vector comprising the following operably linked elements: a transcription promoter; a DNA segment encoding a polypeptide from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:2 from amino acid number 250 (Lys) to amino acid number 491 (Arg); (e) the amino acid sequence as shown in SEQ ID NO:19 from amino acid number 250 (Lys) to 520 (Arg); (f) the amino acid sequence as shown in SEQ ID NO:2 from amino acid number 21 (Arg) to amino acid number 491 (Arg); (g) the amino acid sequence as shown in SEQ ID NO:19 from amino acid number 21 (Arg) to amino acid number 520 (Arg); (h) the amino acid sequence as shown in SEQ ID NO:2 from amino acid number 1 (Met) to amino acid number 491 (Arg); (i) the amino acid sequence as shown in SEQ ID NO:19 from amino acid number 1 (Met) to amino acid number 520 (Arg); (j) the amino acid sequence as shown in SEQ ID NO:21 from amino acid number 21 (Arg) to amino acid number 163 (Trp); (k) the amino acid sequence as shown in SEQ ID NO:21 from amino acid number 21 (Arg) to amino acid number 211 (Ser); and (l) the amino acid sequence as shown in SEQ ID NO:21 from amino acid number 1 (Met) to amino acid number 211 (Ser); and a transcription terminator, wherein the promoter is operably linked to the DNA segment, and the DNA segment is operably linked to the transcription terminator. In one embodiment, the expression vector described above further comprises a secretory signal sequence operably linked to the DNA segment.

Within a third aspect, the present invention provides a cultured cell comprising an expression vector according to the previous paragraph, wherein the cell expresses a polypeptide encoded by the DNA segment. In another embodiment, the expression vector is as described above, wherein the polypeptide further comprises a transmembrane domain consisting of residues 227 (Trp) to 249 (Trp) of SEQ ID NO:2. In another embodiment, the expression vector is as described above, wherein the polypeptide further comprises an intracellular domain consisting of residues 250 (Lys) to 491 (Arg) of SEQ ID NO:2 or 250 (Lys) to 520 (Arg) of SEQ ID NO:19. In another embodiment, the expression vector is as described above, comprising the following operably linked elements: a transcription promoter; a DNA segment encoding a polypeptide from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:21 from amino acid number 21 (Arg) to amino acid number 211 (Ser); and a transcription terminator, wherein the promoter is operably linked to the DNA segment, and the DNA segment is operably linked to the transcription terminator.

Within another aspect, the present invention provides a cultured cell into which has been introduced an expression vector according to the previous paragraph, wherein the cell expresses a soluble receptor polypeptide encoded by the DNA segment.

Within another aspect, the present invention provides a DNA construct encoding a fusion protein, the DNA construct comprising: a first DNA segment encoding a polypeptide comprising a sequence of amino acid residues selected from the group consisting of: (a) the amino acid sequence of SEQ ID NO:2 from amino acid number 1 (Met), to amino acid number 20 (Gly); (b) the amino acid sequence as shown in SEQ ID NO:2 from amino acid number 21 (Arg) to amino acid number 223 (Pro); (c) the amino acid sequence as shown in SEQ ID NO:2 from amino acid number 21 (Arg) to amino acid number 226 (Asn); (d) the amino acid sequence as shown in SEQ ID NO:2 from amino acid number 21 (Arg) to amino acid number 249 (Trp); (e) the amino acid sequence as shown in SEQ ID NO:2 from amino acid number 250 (Lys) to amino acid number 491 (Arg); (f) the amino acid sequence as shown in SEQ ID NO:19 from amino acid number 250 (Lys) to amino acid number 520 (Arg); (g) the amino acid sequence as shown in SEQ ID NO:2 from amino acid number 227 (Trp) to amino acid number 249 (Trp); (h) the amino acid sequence as shown in SEQ ID NO:2 from amino acid number 227 (Trp) to amino acid number 491 (Arg); (i) the amino acid sequence as shown in SEQ ID NO:19 from amino acid number 227 (Trp) to amino acid number 520 (Arg); (j) the amino acid sequence as shown in SEQ ID NO:2 from amino acid number 21 (Arg) to amino acid number 491 (Arg); (k) the amino acid sequence as shown in SEQ ID NO:19 from amino acid number 21 (Arg) to amino acid number 520 (Arg); (l) the amino acid sequence as shown in SEQ ID NO:2 from amino acid number 1 (Met) to amino acid number 491 (Arg); and (m) the amino acid sequence as shown in SEQ ID NO:19 from amino acid number 1 (Met) to amino acid number 520 (Arg); (n) the amino acid sequence as shown in SEQ ID NO:21 from amino acid number 21 (Arg) to amino acid number 163 (Trp); (o) the amino acid sequence as shown in SEQ ID NO:21 from amino acid number 21 (Arg) to amino acid number 211 (Ser); and (p) the amino acid sequence as shown in SEQ ID NO:21 from amino acid number 1 (Met) to amino acid number 211 (Ser); and at least one other DNA segment encoding an additional polypeptide, wherein the first and other DNA segments are connected in-frame; and wherein the first and other DNA segments encode the fusion protein.

Within another aspect, the present invention provides an expression vector comprising the following operably linked elements: a transcription promoter; a DNA construct encoding a fusion protein according to the previous paragraph; and a transcription terminator, wherein the promoter is operably linked to the DNA construct, and the DNA construct is operably linked to the transcription terminator.

Within another aspect, the present invention provides a cultured cell comprising an expression vector according to the previous paragraph, wherein the cell expresses a polypeptide encoded by the DNA construct.

Within another aspect, the present invention provides a method of producing a fusion protein comprising: culturing a cell according to the previous paragraph; and isolating the polypeptide produced by the cell.

Within another aspect, the present invention provides an isolated polypeptide comprising a sequence of amino acid residues selected from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:2 from amino acid number 250 (Lys) to amino acid number 491 (Arg); (e) the amino acid sequence as shown in SEQ ID NO:19 from amino acid number 250 (Lys) to 520 (Arg); (f) the amino acid sequence as shown in SEQ ID NO:2 from amino acid number 21 (Arg) to amino acid number 491 (Arg); (g) the amino acid sequence as shown in SEQ ID NO:19 from amino acid number 21 (Arg) to amino acid number 520 (Arg); (h) the amino acid sequence as shown in SEQ ID NO:2 from amino acid number 1 (Met) to amino acid number 491 (Arg); (i) the amino acid sequence as shown in SEQ ID NO:19 from amino acid number 1 (Met) to amino acid number 520 (Arg); (j) the amino acid sequence as shown in SEQ ID NO:21 from amino acid number 21 (Arg) to amino acid number 163 (Trp); (k) the amino acid sequence as shown in SEQ ID NO:21 from amino acid number 21 (Arg) to amino acid number 211 (Ser); and (l) the amino acid sequence as shown in SEQ ID NO:21 from amino acid number 1 (Met) to amino acid number 211 (Ser). In one embodiment, the isolated polypeptide is as described above, wherein the polypeptide consists of a sequence of amino acid residues that is selected from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:2 from amino acid number 250 (Lys) to amino acid number 491 (Arg); (e) the amino acid sequence as shown in SEQ ID NO:19 from amino acid number 250 (Lys) to 520 (Arg); (f) the amino acid sequence as shown in SEQ ID NO:2 from amino acid number 21 (Arg) to amino acid number 491 (Arg); (g) the amino acid sequence as shown in SEQ ID NO:19 from amino acid number 21 (Arg) to amino acid number 520 (Arg); (h) the amino acid sequence as shown in SEQ ID NO:2 from amino acid number 1 (Met) to amino acid number 491 (Arg); (i) the amino acid sequence as shown in SEQ ID NO:19 from amino acid number 1 (Met) to amino acid number 520 (Arg); (j) the amino acid sequence as shown in SEQ ID NO:21 from amino acid number 21 (Arg) to amino acid number 163 (Trp); (k) the amino acid sequence as shown in SEQ ID NO:21 from amino acid number 21 (Arg) to amino acid number 211 (Ser); and (l) the amino acid sequence as shown in SEQ ID NO:21 from amino acid number 1 (Met) to amino acid number 211 (Ser). In another embodiment, the isolated polypeptide is as described above, wherein the polypeptide further comprises a transmembrane domain consisting of residues 227 (Trp) to 249 (Trp) of SEQ ID NO:2. In another embodiment, the isolated polypeptide is as described above, wherein the polypeptide further comprises an intracellular domain consisting of residues 250 (Lys) to amino acid number 491 (Arg) of SEQ ID NO:2, or 250 (Lys) to amino acid number 520 (Arg) of SEQ ID NO:19. In another embodiment, the isolated polypeptide is as described above, wherein the polypeptide has activity as measured by cell proliferation, activation of transcription of a reporter gene, or wherein the polypeptide encoded by the polynucleotide further binds to an antibody, wherein the antibody is raised to a polypeptide comprising a sequence of amino acids from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:2 from amino acid number 250 (Lys) to amino acid number 491 (Arg); (e) the amino acid sequence as shown in SEQ ID NO:19 from amino acid number 250 (Lys) to 520 (Arg); (f) the amino acid sequence as shown in SEQ ID NO:2 from amino acid number 21 (Arg) to amino acid number 491 (Arg); (g) the amino acid sequence as shown in SEQ ID NO:19 from amino acid number 21 (Arg) to amino acid number 520 (Arg); (h) the amino acid sequence as shown in SEQ ID NO:2 from amino acid number 1 (Met) to amino acid number 491 (Arg); (i) the amino acid sequence as shown in SEQ ID NO:19 from amino acid number 1 (Met) to amino acid number 520 (Arg); (j) the amino acid sequence as shown in SEQ ID NO:21 from amino acid number 21 (Arg) to amino acid number 163 (Trp); (k) the amino acid sequence as shown in SEQ ID NO:21 from amino acid number 21 (Arg) to amino acid number 211 (Ser); and (l) the amino acid sequence as shown in SEQ ID NO:21 from amino acid number 1 (Met) to amino acid number 211 (Ser); and wherein the binding of the antibody to the isolated polypeptide is measured by a biological or biochemical assay including radioimmunoassay, radioimmuno-precipitation, Western blot, or enzyme-linked immunosorbent assay.

Within another aspect, the present invention provides a method of producing a polypeptide comprising: culturing a cell as described in the third aspect, above; and isolating the polypeptide produced by the cell.

Within another aspect, the present invention provides an isolated polypeptide comprising an amino acid segment selected from the group consisting of: (a) the amino acid sequence as shown in SEQ ID NO:2 from amino acid number 21 (Arg) to amino acid number 226 (Asn)); (b) the amino acid sequence as shown in SEQ ID NO:4; (c) the amino acid sequence as shown in SEQ ID NO:21 from amino acid number 21 (Arg) to amino acid number 211 (Ser); and (c) sequences that are at least 90% identical to (a), (b) or (c), wherein the polypeptide is substantially free of transmembrane and intracellular domains ordinarily associated with hematopoietic receptors.

Within another aspect, the present invention provides a method of producing a polypeptide comprising: culturing a cell according to into which has been introduced an expression vector comprising the following operably linked elements: a transcription promoter; a DNA segment encoding a polypeptide from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:21 from amino acid number 21 (Arg) to amino acid number 211 (Ser); and a transcription terminator, wherein the promoter is operably linked to the DNA segment, and the DNA segment is operably linked to the transcription terminator; and isolating the polypeptide produced by the cell.

Within another aspect, the present invention provides a method of producing an antibody to a polypeptide comprising: inoculating an animal with a polypeptide selected from the group consisting of: (a) a polypeptide consisting of 50 to 471 amino acids, wherein the polypeptide comprises a contiguous sequence of amino acids in SEQ ID NO:2 from amino acid number 21 (Arg), to amino acid number 491 (Arg); (b) a polypeptide consisting of 50 to 500 amino acids, wherein the polypeptide comprises a contiguous sequence of amino acids in SEQ ID NO:19 from amino acid number 21 (Arg), to amino acid number 520 (Arg); (c) a polypeptide consisting of 50 to 191 amino acids, wherein the polypeptide comprises a contiguous sequence of amino acids in SEQ ID NO:21 from amino acid number 21 (Arg), to amino acid number 211 (Ser); (d) a polypeptide according to claim 2; (e) a polypeptide comprising amino acid number 21 (Arg) to 119 (Tyr) of SEQ ID NO:2; (f) a polypeptide comprising amino acid number 125 (Pro) to 223 (Pro) of SEQ ID NO:2; (g) a polypeptide comprising a hydrophilic peptide of SEQ ID NO:2 as predicted from a hydrophobicity plot using a Hopp/Woods hydrophilicity profile based on a sliding six-residue window, with buried G, S, and T residues and exposed H, Y, and W residues ignored; and wherein the polypeptide elicits an immune response in the animal to produce the antibody; and isolating the antibody from the animal.

Within another aspect, the present invention provides an antibody produced by the method described in the previous paragraph, which specifically binds to a polypeptide of SEQ ID NO:2, SEQ ID NO:19 or SEQ ID NO:21. In one embodiment, the antibody described above is a monoclonal antibody.

Within another aspect, the present invention provides an antibody that specifically binds to a polypeptide as disclosed above.

Within another aspect, the present invention provides a method of detecting, in a test sample, the presence of a modulator of the activity of a cytokine receptor protein comprising: culturing a cell into which has been introduced an expression vector according to claim 6, wherein the cell expresses the protein encoded by the DNA segment in the presence and absence of a test sample; and comparing levels of activity of the protein in the presence and absence of a test sample, by a biological or biochemical assay; and determining from the comparison, the presence of modulator the cytokine receptor protein activity in the test sample.

Within another aspect, the present invention provides a method for detecting a cytokine receptor ligand within a test sample, comprising: contacting a test sample with a cytokine receptor polypeptide comprising an amino acid sequence from the group consisting of: (a) the amino acid sequence as shown in SEQ ID NO:4; (b) the amino acid sequence as shown in SEQ ID NO:2 from amino acid number 21 (Arg) to amino acid number 226 (Asn); and (c) the amino acid sequence as shown in SEQ ID NO:21 from amino acid number 21 (Arg) to amino acid number 211 (Ser); and detecting the binding of the cytokine receptor polypeptide to a ligand in the sample. In one embodiment, the method for detecting a cytokine receptor ligand is as disclosed above, wherein the cytokine receptor polypeptide is membrane bound within a cultured cell, and the detecting step comprises measuring a biological response in the cultured cell. In another embodiment, the method for detecting a cytokine receptor ligand is as disclosed above, wherein the biological response is cell proliferation or activation of transcription of a reporter gene.

Within another aspect, the present invention provides a method for detecting a genetic abnormality in a patient, comprising: obtaining a genetic sample from a patient; producing a first reaction product by incubating the genetic sample with a polynucleotide comprising at least 14 contiguous nucleotides of SEQ ID NO:1, SEQ ID NO:18 or SEQ ID NO:20 or the complement of SEQ ID NO:1, SEQ ID NO:18 or SEQ ID NO:20, under conditions wherein said polynucleotide will hybridize to complementary polynucleotide sequence; visualizing the first reaction product; and comparing said first reaction product to a control reaction product from a wild type patient, wherein a difference between said first reaction product and said control reaction product is indicative of a genetic abnormality in the patient.

Within another aspect, the present invention provides a method for detecting a cancer in a patient, comprising: obtaining a tissue or biological sample from a patient; incubating the tissue or biological sample with an antibody of that specifically binds a polypeptide consisting of a sequence of amino acid residues that is selected from the group consisting of: (a) the amino acid sequence as shown in SEQ ID NO:2 from amino acid number 21 (Arg) to amino acid number 223 (Pro); (b) the amino acid sequence as shown in SEQ ID NO:2 from amino acid number 21 (Arg) to amino acid number 226 (Asn); (c) the amino acid sequence as shown in SEQ ID NO:2 from amino acid number 21 (Arg) to amino acid number 249 (Trp); (d) the amino acid sequence as shown in SEQ ID NO:2 from amino acid number 250 (Lys) to amino acid number 491 (Arg); (e) the amino acid sequence as shown in SEQ ID NO:19 from amino acid number 250 (Lys) to 520 (Arg); (f) the amino acid sequence as shown in SEQ ID NO:2 from amino acid number 21 (Arg) to amino acid number 491 (Arg); (g) the amino acid sequence as shown in SEQ ID NO:19 from amino acid number 21 (Arg) to amino acid number 520 (Arg); (h) the amino acid sequence as shown in SEQ ID NO:2 from amino acid number 1 (Met) to amino acid number 491 (Arg); (i) the amino acid sequence as shown in SEQ ID NO:19 from amino acid number 1 (Met) to amino acid number 520 (Arg); (j) the amino acid sequence as shown in SEQ ID NO:21 from amino acid number 21 (Arg) to amino acid number 163 (Trp); (k) the amino acid sequence as shown in SEQ ID NO:21 from amino acid number 21 (Arg) to amino acid number 211 (Ser); and (l) the amino acid sequence as shown in SEQ ID NO:21 from amino acid number 1 (Met) to amino acid number 211 (Ser) under conditions wherein the antibody binds to its complementary polypeptide in the tissue or biological sample; visualizing the antibody bound in the tissue or biological sample; and comparing levels of antibody bound in the tissue or biological sample from the patient to a normal control tissue or biological sample, wherein an increase in the level of antibody bound to the patient tissue or biological sample relative to the normal control tissue or biological sample is indicative of a cancer in the patient.

Within another aspect, the present invention provides a method for detecting a cancer in a patient, comprising:

obtaining a tissue or biological sample from a patient;

labeling a polynucleotide comprising at least 14 contiguous nucleotides of SEQ ID NO:1, SEQ ID NO:18 or SEQ ID NO:20 or the complement of SEQ ID NO:1, SEQ ID NO:18 or SEQ ID NO:20;

incubating the tissue or biological sample with under conditions wherein the polynucleotide will hybridize to complementary polynucleotide sequence;

visualizing the labeled polynucleotide in the tissue or biological sample; and comparing the level of labeled polynucleotide hybridization in the tissue or biological sample from the patient to a normal control tissue or biological sample, wherein an increase in the labeled polynucleotide hybridization to the patient tissue or biological sample relative to the normal control tissue or biological sample is indicative of a cancer in the patient.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9 M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers, multimers, or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14-17 nucleotides) can be used. PCR primers are at least 5 nucleotides in length, preferably 15 or more nt, more preferably 20-30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. Cell-surface cytokine receptors are characterized by a multi-domain structure as discussed in more detail below. These receptors are anchored in the cell membrane by a transmembrane domain characterized by a sequence of hydrophobic amino acid residues (typically about 21-25 residues), which is commonly flanked by positively charged residues (Lys or Arg). In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). The term "receptor polypeptide" is used to denote complete receptor polypeptide chains and portions thereof, including isolated functional domains (e.g., ligand-binding domains). The terms "ligand-binding domain(s)" and "cytokine-binding domain(s)" can be used interchangeably.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

Cytokine receptor subunits are characterized by a multi-domain structure comprising a ligand-binding domain and an effector domain that is typically involved in signal transduction. Multimeric cytokine receptors include homodimers (e.g., PDGF receptor αα and ββ isoforms, erythropoietin receptor, MPL (thrombopoietin receptor), and G-CSF receptor); heterodimers whose subunits each have ligand-binding and effector domains (e.g., PDGF receptor αβ isoform); and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of their structures and functions. Class I hematopoietic receptors, for example, are characterized by the presence of a domain containing conserved cysteine residues and the WSXWS motif (SEQ ID NO:5). Additional domains, including protein kinase domains; fibronectin type III domains; and immunoglobulin domains, which are characterized by disulfide-bonded loops, are present in certain hematopoietic receptors. Cytokine receptor structure has been reviewed by Urdal, *Ann. Reports Med. Chem.* 26:221-228, 1991 and Cosman, *Cytokine* 5:95-106, 1993. It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members.

Cell-surface cytokine receptors are further characterized by the presence of additional domains. These receptors are anchored in the cell membrane by a transmembrane domain characterized by a sequence of hydrophobic amino acid residues (typically about 21-25 residues), which is commonly flanked by positively charged residues (Lys or Arg). On the opposite end of the protein from the extracellular domain and separated from it by the transmembrane domain is an intracellular domain.

The Zcytor19 receptor of the present invention is a class II cytokine receptor. These receptors usually bind to four-helix-bundle cytokines. Interleukin-10 and the interferons have receptors in this class (e.g., interferon-gamma, alpha and beta chains and the interferon-alpha/beta receptor alpha and beta chains). Class II cytokine receptors are characterized by the presence of one or more cytokine receptor modules (CRM) in their extracellular domains. Other class II cytokine receptors include zcytor11 (commonly owned U.S. Pat. No. 5,965,704), CRF2-4 (Genbank Accession No. Z17227), IL-10R (Genbank Accession No.s U00672 and NM_001558), DIRS1, zcytor7 (commonly owned U.S. Pat. No. 5,945,511), zcytor16, tissue factor, and the like. The CRMs of class II cytokine receptors are somewhat different than the better-known CRMs of class I cytokine receptors. While the class II CRMs contain two type-III fibronectin-like domains, they differ in organization.

Zcytor19, like all known class II receptors except interferon-alpha/beta receptor alpha chain, has only a single class II CRM in its extracellular domain. Zcytor19 is a receptor for a helical cytokine of the interferon/IL-10 class. As was stated above, Zcytor19 is similar to other Class II cytokine receptors such as zcytor11 and zcytor16. Analysis of a human cDNA clone encoding Zcytor19 (SEQ ID NO:1) revealed an open reading frame encoding 491 amino acids (SEQ ID NO:2) comprising a secretory signal sequence (residues 1 (Met) to 20 (Gly) of SEQ ID NO:2) and a mature zcytor19 cytokine receptor polypeptide (residues 21 (Arg) to 491 (Arg) of SEQ ID NO:2) an extracellular ligand-binding domain of approximately 206 amino acid residues (residues 21 (Arg) to 226 (Asn) of SEQ ID NO:2), a transmembrane domain of approximately 23 amino acid residues (residues 227 (Trp) to 249 (Trp) of SEQ ID NO:2), and an intracellular domain of approximately 242 amino acid residues (residues 250 (Lys) to 491 (Arg) of SEQ ID NO:2). Within the extracellular ligand-binding domain, there are two fibronectin type III domains and a linker region. The first fibronectin type III domain comprises residues 21 (Arg) to 119 (Tyr) of SEQ ID NO:2, the linker comprises residues 120 (Leu) to 124 (Glu) of SEQ ID NO:2, and the second fibronectin type III domain is short, and comprises residues 125 (Pro) to 223 (Pro) of SEQ ID NO:2. Thus, a polypeptide comprising amino acids 21 (Arg) to 223 (Pro) of SEQ ID NO:2 (SEQ ID NO:4) is considered a ligand binding fragment. In addition as typically conserved in class II receptors, there are conserved Tryptophan residues comprising residues 43 (Trp) and 68 (Trp) as shown in SEQ ID NO:2, and conserved Cysteine residues at positions 74, 82, 195, 217 of SEQ ID NO:2.

In addition, the present invention includes a variant of zcytor19 receptor that includes an approximately 30 amino acid insertion in the intracellular domain of the polypeptide (in reference to SEQ ID NO:2). Analysis of a human cDNA clone encoding Zcytor19 (SEQ ID NO:18) revealed an open reading frame encoding 520 amino acids (SEQ ID NO:19) comprising a secretory signal sequence (residues 1 (Met) to 20 (Gly) of SEQ ID NO:19) and a mature zcytor19 cytokine receptor polypeptide (residues 21 (Arg) to 520 (Arg) of SEQ ID NO:19) an extracellular ligand-binding domain of approximately 206 amino acid residues (residues 21 (Arg) to 226 (Asn) of SEQ ID NO:19), a transmembrane domain of approximately 23 amino acid residues (residues 227 (Trp) to 249 (Trp) of SEQ ID NO:19), and an intracellular domain of approximately 271 amino acid residues (residues 250 (Lys) to 520 (Arg) of SEQ ID NO:19). Within the extracellular ligand-binding domain, there are two fibronectin type III domains and a linker region. The first fibronectin type III domain comprises residues 21 (Arg) to 119 (Tyr) of SEQ ID NO:19, the linker comprises residues 120 (Leu) to 124 (Glu) of SEQ ID NO:19, and the second fibronectin type III domain comprises residues 125 (Pro) to 223 (Pro) of SEQ ID NO:19. Thus, a polypeptide comprising amino acids 21 (Arg) to 223 (Pro) of SEQ ID NO:19 (SEQ ID NO:4) is considered a ligand binding fragment. In addition as typically conserved in class II receptors, there are conserved Tryptophan residues comprising residues 43 (Trp) and 68 (Trp) as shown in SEQ ID NO:19, and conserved Cysteine residues at positions 74, 82, 195, 217 of SEQ ID NO:19.

Moreover, a truncated soluble form of the zcytor19 receptor polypeptide appears to be naturally expressed. Analysis of a human cDNA clone encoding the truncated soluble Zcytor19 (SEQ ID NO:20) revealed an open reading frame encoding 211 amino acids (SEQ ID NO:21) comprising a secretory signal sequence (residues 1 (Met) to 20 (Gly) of SEQ ID NO:21) and a mature truncated soluble zcytor19 receptor polypeptide (residues 21 (Arg) to 211 (Ser) of SEQ ID NO:21) a truncated extracellular ligand-binding domain of approximately 143 amino acid residues (residues 21 (Arg) to 163 (Trp) of SEQ ID NO:21), no transmembrane domain, but an additional domain of approximately 48 amino acid residues (residues 164 (Lys) to 211 (Ser) of SEQ ID NO:21). Within the truncated extracellular ligand-binding domain, there are two fibronectin type III domains and a linker region. The first fibronectin type III domain comprises residues 21 (Arg) to 119 (Tyr) of SEQ ID NO:21, the linker comprises residues 120 (Leu) to 124 (Glu) of SEQ ID NO:21, and the second fibronectin type III domain comprises residues 125 (Pro) to 163 (Trp) of SEQ ID NO:21. Thus, a polypeptide comprising amino acids 21 (Arg) to 163 (Trp) of SEQ ID NO:21 is considered a ligand binding fragment. In addition as typically conserved in class II receptors, there are conserved Tryptophan residues comprising residues 43 (Trp) and 68 (Trp) as shown in SEQ ID NO:21, and conserved Cysteine residues in this truncated soluble form of the zcytor19 receptor are at positions 74, and 82 of SEQ ID NO:21.

Moreover, the zcytor19 polypeptide of the present invention can be naturally expressed wherein the extracellular ligand binding domain comprises an additional 5-15 amino acid residues at the N-terminus of the mature polypeptide, or extracellular cytokine binding domain or cytokine binding fragment, as described above.

Those skilled in the art will recognize that these domain boundaries are approximate and are based on alignments with known proteins and predictions of protein folding. Deletion of residues from the ends of the domains is possible. Moreover the regions, domains and motifs described above in reference to SEQ ID NO:2 are also as shown in SEQ ID NO:1; domains and motifs described above in reference to SEQ ID NO:19 are also as shown in SEQ ID NO:18; and domains and motifs described above in reference to SEQ ID NO:21 are also as shown in SEQ ID NO:20.

The presence of transmembrane regions, and conserved and low variance motifs generally correlates with or defines important structural regions in proteins. Regions of low variance (e.g., hydrophobic clusters) are generally present in regions of structural importance (Sheppard, P. et al., *Gene* 150:163-167, 1994). Such regions of low variance often contain rare or infrequent amino acids, such as Tryptophan. The regions flanking and between such conserved and low variance motifs may be more variable, but are often functionally significant because they may relate to or define important structures and activities such as binding domains, biological and enzymatic activity, signal transduction, cell-cell interaction, tissue localization domains and the like.

The regions of conserved amino acid residues in zcytor19, described above, can be used as tools to identify new family members. For instance, reverse transcription-polymerase chain reaction (RT-PCR) can be used to amplify sequences encoding the conserved regions from RNA obtained from a variety of tissue sources or cell lines. In particular, highly degenerate primers designed from the zcytor19 sequences are useful for this purpose. Designing and using such degenerate primers may be readily performed by one of skill in the art.

The present invention provides polynucleotide molecules, including DNA and RNA molecules that encode the zcytor19 polypeptides disclosed herein. Those skilled in the art will recognize that, in view of the degeneracy of the genetic code, considerable sequence variation is possible among these polynucleotide molecules. SEQ ID NO:3 is a degenerate DNA sequence that encompass all DNAs that encode the zcytor19 polypeptide of SEQ ID NO:2; SEQ ID NO:28 is a degenerate DNA sequence that encompass all DNAs that encode the zcytor19 polypeptide of SEQ ID NO:19; and SEQ ID NO:29 is a degenerate DNA sequence that encompass all DNAs that encode the zcytor19 polypeptide of SEQ ID NO:21. Those skilled in the art will recognize that the degenerate sequences of SEQ ID NO:3, SEQ ID NO:28, and SEQ ID NO:29 also provide all RNA sequences encoding SEQ ID NO:2, SEQ ID NO:19, and SEQ ID NO:21 by substituting U for T. Thus, zcytor19 polypeptide-encoding polynucleotides comprising nucleotide 1 to nucleotide 1473 of SEQ ID NO:3, 1 to nucleotide 1560 of SEQ ID NO:28, 1 to nucleotide 633 of SEQ ID NO:29, and their RNA equivalents are contemplated by the present invention. Moreover, subfragments of these degenerate sequences such as the mature forms of the polypeptides, extracellular, cytokine binding domains, intracellular domains, and the like, as described herein are included in the present invention. One of skill in the art upon reference to SEQ ID NO:2, SEQ ID NO:19 and SEQ ID NO:21 and the subfragments thereof described herein could readily determine the respective nucleotides in SEQ ID NO:3, SEQ ID NO:28 or SEQ ID NO:29, that encode those subfragments. Table 1 sets forth the one-letter codes used within SEQ ID NO:3, to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |

TABLE 1-continued

| Nucleotide | Resolution | Complement | Resolution |
|---|---|---|---|
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN)

can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2, SEQ ID NO:19, and/or SEQ ID NO:21. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene* 18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as templates for optimizing expression of zcytor19 polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, SEQ ID NO:18, or SEQ ID NO:20, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences (e.g., >50 base pairs) is performed at temperatures of about 20-25° C. below the calculated $T_m$. For smaller probes (e.g., <50 base pairs) hybridization is typically carried out at the $T_m$ or 5-10° C. below. This allows for the maximum rate of hybridization for DNA-DNA and DNA-RNA hybrids. Higher degrees of stringency at lower temperatures can be achieved with the addition of formamide which reduces the $T_m$ of the hybrid about 1° C. for each 1% formamide in the buffer solution. Suitable stringent hybridization conditions are equivalent to about a 5 h to overnight incubation at about 42° C. in a solution comprising: about 40-50% formamide, up to about 6×SSC, about 5× Denhardt's solution, zero up to about 10% dextran sulfate, and about 10-20 μg/ml denatured commercially-available carrier DNA. Generally, such stringent conditions include temperatures of 20-70° C. and a hybridization buffer containing up to 6×SSC and 0-50% formamide; hybridization is then followed by washing filters in up to about 2×SSC. For example, a suitable wash stringency is equivalent to 0.1×SSC to 2×SSC, 0.1% SDS, at 55° C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the Tm, hybridization and wash solutions used, and are routinely determined empirically by one of skill in the art.

As previously noted, the isolated polynucleotides of the present invention include DNA and RNA. Methods for preparing DNA and RNA are well known in the art. In general, RNA is isolated from a tissue or cell that produces large amounts of zcytor19 RNA. Such tissues and cells are identified by Northern blotting (Thomas, *Proc. Natl. Acad. Sci. USA* 77:5201, 1980), and include PBLs, spleen, thymus, bone marrow, and lymph tissues, human erythroleukemia cell lines, acute monocytic leukemia cell lines, B-cell and T-cell leukemia tissue or cell lines, other lymphoid and hematopoietic cell lines, and the like. Total RNA can be prepared using guanidinium isothiocyanate extraction followed by isolation by centrifugation in a CsCl gradient (Chirgwin et al., *Biochemistry* 18:52-94, 1979). Poly $(A)^+$ RNA is prepared from total RNA using the method of Aviv and Leder (*Proc. Natl. Acad. Sci. USA* 69:1408-12, 1972). Complementary DNA (cDNA) is prepared from poly$(A)^+$ RNA using known methods. In the alternative, genomic DNA can be isolated. Polynucleotides encoding zcytor19 polypeptides are then identified and isolated by, for example, hybridization or polymerase chain reaction (PCR) (Mullis, U.S. Pat. No. 4,683,202).

A full-length clone encoding zcytor19 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zcytor19, receptor fragments, or other specific binding partners.

The polynucleotides of the present invention can also be synthesized using DNA synthesis machines. Currently the method of choice is the phosphoramidite method. If chemically synthesized double stranded DNA is required for an application such as the synthesis of a gene or a gene fragment, then each complementary strand is made separately. The production of short polynucleotides (60 to 80 bp) is technically straightforward and can be accomplished by synthesizing the complementary strands and then annealing them. However, for producing longer polynucleotides (>300 bp), special strategies are usually employed, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

An alternative way to prepare a full-length gene is to synthesize a specified set of overlapping oligonucleotides (40 to 100 nucleotides). After the 3' and 5' short overlapping complementary regions (6 to 10 nucleotides) are annealed, large gaps still remain, but the short base-paired regions are both long enough and stable enough to hold the structure together. The gaps are filled and the DNA duplex is completed via enzymatic DNA synthesis by *E. coli* DNA polymerase I. After the enzymatic synthesis is completed, the nicks are sealed with T4 DNA ligase. Double-stranded constructs are sequentially linked to one another to form the entire gene sequence which is verified by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem.* 53: 323-56, 1984 and Climie et al., *Proc. Natl. Acad. Sci. USA* 87:633-7, 1990. Moreover, other sequences are generally added that contain signals for proper initiation and termination of transcription and translation.

The present invention further provides counterpart polypeptides and polynucleotides from other species (orthologs). These species include, but are not limited to mammalian, avian, amphibian, reptile, fish, insect and other vertebrate and invertebrate species. Of particular interest are zcytor19 polypeptides from other mammalian species, including murine, porcine, ovine, bovine, canine, feline, equine, and other primate polypeptides. Orthologs of human zcytor19 can be cloned using information and compositions provided by the present invention in combination with conventional cloning techniques. For example, a cDNA can be cloned using mRNA obtained from a tissue or cell type that expresses zcytor19 as disclosed herein. Suitable sources of mRNA can be identified by probing Northern blots with probes designed from the sequences disclosed herein. A library is then prepared from mRNA of a positive tissue or cell line. A zcytor19-encoding cDNA can then be isolated by a variety of methods, such as by probing with a complete or partial human cDNA or with one or more sets of degenerate probes based on the disclosed sequences. A cDNA can also be cloned using PCR (Mullis, supra.), using primers designed from the representative human zcytor19 sequence disclosed herein. Within an additional method, the cDNA library can be used to transform or transfect host cells, and expression of the cDNA of interest can be detected with an antibody to zcytor19 polypeptide. Similar techniques can also be applied to the isolation of genomic clones.

Cytokine receptor subunits are characterized by a multi-domain structure comprising an extracellular domain, a transmembrane domain that anchors the polypeptide in the cell membrane, and an intracellular domain. The extracellular domain is typically a ligand-binding domain, and the intracellular domain is typically an effector domain involved in signal transduction, although ligand-binding and effector functions may reside on separate subunits of a multimeric receptor. The ligand-binding domain may itself be a multi-domain structure. Multimeric receptors include homodimers (e.g., PDGF receptor αα and ββ isoforms, erythropoietin receptor, MPL, and G-CSF receptor), heterodimers whose subunits each have ligand-binding and effector domains (e.g., PDGF receptor αβ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of the structure and function. Hematopoietic receptors, for example, are characterized by the presence of a domain containing conserved cysteine residues and the WSXWS motif (SEQ ID NO:5). Cytokine receptor structure has been reviewed by Urdal, *Ann. Reports Med. Chem.* 26:221-228, 1991 and Cosman, *Cytokine* 5:95-106, 1993. Under selective pressure for organisms to acquire new biological functions, new receptor family members likely arise from duplication of existing receptor genes leading to the existence of multi-gene families. Family members thus contain vestiges of the ancestral gene, and these characteristic features can be exploited in the isolation and identification of additional family members. Thus, the cytokine receptor superfamily is subdivided into several families, for example, the immunoglobulin family (including CSF-1, MGF, IL-1, and PDGF receptors); the hematopoietin family (including IL-2 receptor β-subunit, GM-CSF receptor α-subunit, GM-CSF receptor β-subunit; and G-CSF, EPO, IL-3, IL-4, IL-5, IL-6, IL-7, and IL-9 receptors); TNF receptor family (including TNF (p80) TNF (p60) receptors, CD27, CD30, CD40, Fas, and NGF receptor).

Analysis of the zcytor19 sequence suggests that it is a member of the same receptor subfamily as the class II cytokine receptors, for example, interferon-gamma, alpha and beta chains and the interferon-alpha/beta receptor alpha and beta chains, zcytor11 (commonly owned U.S. Pat. No. 5,965,704), CRF2-4 (Genbank Accession No. Z17227), DIRS1, zcytor7 (commonly owned U.S. Pat. No. 5,945,511) receptors. Receptors in this subfamily may associate to form homodimers that transduce a signal. Several members of the subfamily (e.g., receptors that bind interferon, IL-10, IL-19, and IL-TIF) combine with a second subunit (termed a β-subunit) to bind ligand and transduce a signal. Specific β-subunits associate with a plurality of specific cytokine receptor subunits. For example, with class II cytokine receptors commonly owned zcytor11 (U.S. Pat. No. 5,965,704) and CRF2-4 receptor heterodimerize to bind the cytokine IL-TIF (See, WIPO publication WO 00/24758; Dumontier et al., *J. Immunol.* 164:1814-1819, 2000; Spencer, S D et al., *J. Exp. Med.* 187:571-578, 1998; Gibbs, V C and Pennica *Gene* 186:97-101, 1997 (CRF2-4 cDNA); Xie, M H et al., *J. Biol. Chem.* 275: 31335-31339, 2000; and Kotenko, S V et al., *J. Biol. Chem.* manuscript in press M007837200). Moreover, IL-10β receptor may be involved as a receptor for IL-TIF, and it is believed to be synonymous with CRF2-4 (Dumoutier, L. et al., *Proc. Nat'l. Acad. Sci.* 97:10144-10149, 2000; Liu Y et al, *J. Immunol.* 152; 1821-1829, 1994 (IL-10R cDNA). As such, class II receptor complexes can be heterodimeric, or multimeric. Thus, monomeric, homodimeric, heterodimeric and multimeric receptors comprising a zcytor19 subunit are encompassed by the present invention.

Those skilled in the art will recognize that the sequence disclosed in SEQ ID NO:1, SEQ ID NO:18, or SEQ ID NO:20 represents one allele of human zcytor19 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, SEQ ID NO:18 or SEQ ID NO:20 including those containing silent mutations and those in which mutations result in amino acid sequence changes, are within the scope of the present invention, as are proteins which are allelic variants of SEQ ID NO:2, SEQ ID NO:19 or SEQ ID NO:21. cDNAs generated from alternatively spliced mRNAs, which retain the properties of the zcytor19 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated zcytor19 polypeptides that are substantially similar to the polypeptides of SEQ ID NO:2, SEQ ID NO:19 or SEQ ID NO:21 and their orthologs. The term "substantially similar" is used herein to denote polypeptides having at least 70%, more preferably at least 80%, sequence identity to the sequences shown in SEQ ID NO:2, SEQ ID NO:19 or SEQ ID NO:21 or their orthologs. Such polypeptides will more preferably be at least 90% identical, and most preferably 95% or more identical to SEQ ID NO:2, SEQ ID NO:19 or SEQ ID NO:21 or its orthologs.) Percent sequence identity is determined by conventional methods. See, for example, Altschul et al., *Bull. Math. Bio.* 48: 603-616, 1986 and Henikoff and Henikoff, *Proc. Natl. Acad. Sci. USA* 89:10915-10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{\begin{gathered}[\text{length of the longer sequence plus the}\\ \text{number of gaps introduced into the longer}\\ \text{sequence in order to align the two sequences}]\end{gathered}} \times 100$$

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zcytor19. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2, SEQ ID NO:19 or SEQ ID NO:21) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62, with other parameters set as default. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

between one to six, preferably from three to six, most preferably three, with other FASTA program parameters set as default.

The BLOSUM62 table (Table 3) is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant zcytor19 polypeptides or substantially homologous zcytor19 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag. The present invention thus includes polypeptides that comprise a sequence that is at least 80%, preferably at least 90%, and more preferably 95% or more identical to the corresponding region of SEQ ID NO:2, SEQ ID NO:19 or SEQ ID NO:21, excluding the tags, extension, linker sequences and the like. Polypeptides comprising affinity tags can further comprise a proteolytic cleavage site between the zcytor19 polypeptide and the affinity tag. Suitable sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions. For example, a zcytor19 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zcytor19 polypeptide fusions can be expressed in genetically engineered cells to produce a variety of multimeric zcytor19 analogs. Auxiliary domains can be fused to zcytor19 polypeptides to target them to specific cells, tissues, or macromolecules (e.g., collagen). A zcytor19 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for zcytor19 amino acid residues.

Essential amino acids in the polypeptides of the present invention can be identified according to procedures known in the art, such as site-directed mutagenesis or alanine-scanning mutagenesis (Cunningham and Wells, *Science* 244: 1081-5, 1989; Bass et al., *Proc. Natl. Acad. Sci. USA* 88:4498-502, 1991). In the latter technique, single alanine mutations are introduced at every residue in the molecule, and the resultant mutant molecules are tested for biological activity (e.g. ligand binding and signal transduction) as disclosed below to identify amino acid residues that are critical to the activity of the molecule. See also, Hilton et al., *J. Biol. Chem.* 271:4699-4708, 1996. Sites of ligand-receptor, protein-protein or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-312, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related receptors.

Determination of amino acid residues that are within regions or domains that are critical to maintaining structural integrity can be determined. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the Insight II® viewer and homology modeling tools; MSI, San Diego, Calif.), secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in zcytor19 polypeptides so as to minimize disruption of higher order structure essential to biological activity. For example, when the zcytor19 polypeptide comprises one or more structural domains, such as Fibronectin Type III domains, changes in amino acid residues will be made so as not to disrupt the domain structure and geometry and other components of the molecule where changes in conformation ablate some critical function, for example, binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same disulfide bonding pattern as the standard molecule folding would be affected. Another well known and accepted method for measuring folding is circular dichroism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structural similarities between proteins and polypeptides (Schaanan et al., *Science* 257:961-964, 1992).

A Hopp/Woods hydrophilicity profile of the zcytor19 protein sequence as shown in SEQ ID NO:2, SEQ ID NO:19 or SEQ ID NO:21 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in zcytor19, hydrophilic regions include amino acid residues 295 through 300 of SEQ ID NO:2; 451 through 456 of SEQ ID NO:2; 301 through 306 of SEQ ID NO:2; 244 through 299 of SEQ ID NO:2; and 65 through 70 of SEQ ID NO:2. Moreover, one of skill in the art would recognize that zcytor19 hydrophilic regions including antigenic epitope-bearing polypeptides can be predicted by a Jameson-Wolf plot, e.g., using DNASTAR Protean program (DNASTAR, Inc., Madison, Wis.).

Those skilled in the art will recognize that hydrophilicity or hydrophobicity will be taken into account when designing modifications in the amino acid sequence of a zcytor19 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such residues as shown in SEQ ID NO:2. However, Cysteine residues at positions 74, 82, 195, and 217 of SEQ ID NO:2 or SEQ ID NO:19, and corresponding Cys residues in SEQ ID NO:4 are relatively intolerant of substitution. Moreover, Cysteine residues at positions 74, 82, of SEQ ID NO:21 are relatively intolerant of substitution.

The identities of essential amino acids can also be inferred from analysis of sequence similarity between class II cytokine receptor family members with zcytor19. Using methods such as "FASTA" analysis described previously, regions of high similarity are identified within a family of proteins and used to analyze amino acid sequence for conserved regions. An alternative approach to identifying a variant zcytor19 polynucleotide on the basis of structure is to determine whether a nucleic acid molecule encoding a potential variant zcytor19 polynucleotide can hybridize to a nucleic acid molecule having the nucleotide sequence of SEQ ID NO:1, SEQ ID NO:18, or SEQ ID NO:20 as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. Such mutagenesis and screening methods are routine in the art. See also, Hilton et al., *J. Biol. Chem.* 271:4699 (1996).

The present invention also includes functional fragments of zcytor19 polypeptides and nucleic acid molecules encoding such functional fragments. A "functional" zcytor19 or fragment thereof defined herein is characterized by its proliferative or differentiating activity, by its ability to induce or inhibit specialized cell functions, or by its ability to bind specifically to an anti-zcytor19 antibody or zcytor19 ligand (either soluble or immobilized). Moreover, functional fragments also include the signal peptide, intracellular signaling domain, and the like. As previously described herein, zcytor19 is characterized by a class II cytokine receptor structure. Thus, the present invention further provides fusion proteins encompassing: (a) polypeptide molecules comprising an extracellular domain, cytokine-binding domain, or intracellular domain described herein; and (b) functional fragments comprising one or more of these domains. The other polypeptide portion of the fusion protein may be contributed by another class II cytokine receptor, for example, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511), and the like, or by a non-native and/or an unrelated secretory signal peptide that facilitates secretion of the fusion protein.

Routine deletion analyses of nucleic acid molecules can be performed to obtain functional fragments of a nucleic acid molecule that encodes a zcytor19 polypeptide. As an illustration, DNA molecules having the nucleotide sequence of SEQ ID NO:1, SEQ ID NO:18, or SEQ ID NO:20 or fragments thereof, can be digested with Bal31 nuclease to obtain a series of nested deletions. These DNA fragments are then inserted into expression vectors in proper reading frame, and the expressed polypeptides are isolated and tested for zcytor19 activity, or for the ability to bind anti-zcytor19 antibodies or zcytor19 ligand. One alternative to exonuclease digestion is to use oligonucleotide-directed mutagenesis to introduce deletions or stop codons to specify production of a desired zcytor19 fragment. Alternatively, particular fragments of a zcytor19 polynucleotide can be synthesized using the polymerase chain reaction.

Standard methods for identifying functional domains are well-known to those of skill in the art. For example, studies on the truncation at either or both termini of interferons have been summarized by Horisberger and *Di Marco, Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1, Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241:53-57, 1988) or Bowie and Sauer (*Proc. Natl. Acad. Sci. USA* 86:2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/062045) and region-directed mutagenesis (Derbyshire et al., *Gene* 46:145, 1986; Ner et al., *DNA* 7:127, 1988).

Variants of the disclosed zcytor19 DNA and polypeptide sequences can be generated through DNA shuffling as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized zcytor19 receptor polypeptides in host cells. Preferred assays in this regard include cell proliferation assays and biosensor-based ligand-binding assays, which are described below. Mutagenized DNA molecules that encode active receptors or portions thereof (e.g., ligand-binding fragments, signaling domains, and the like) can be recovered from the host cells and rapidly sequenced using modern equipment. These methods allow the routine and rapid determination of the importance of individual amino acid residues in a polypeptide of interest.

In addition, the proteins of the present invention (or polypeptide fragments thereof) can be joined to other bioactive molecules, particularly cytokine receptors, to provide multi-functional molecules. For example, one or more domains from zcytor19 soluble receptor can be joined to other cytokine soluble receptors to enhance their biological properties or efficiency of production.

The present invention thus provides a series of novel, hybrid molecules in which a segment comprising one or more of the domains of zcytor19 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Using the methods discussed herein, one of ordinary skill in the art can identify and/or prepare a variety of polypeptide fragments or variants of SEQ ID NO:2 or SEQ ID NO:19 that retain the signal transduction or ligand binding activity. For example, one can make a zcytor19 "soluble receptor" by preparing a variety of polypeptides that are substantially homologous to the extracellular cytokine-binding domain (residues 21 (Arg) to 226 (Asn) of SEQ ID NO:2 or SEQ ID NO:19), a cytokine-binding fragment (e.g., residues 21 (Arg) to 223 (Pro) of SEQ ID NO:2 or SEQ ID NO:19; SEQ ID NO:4) or allelic variants or species orthologs thereof) and retain ligand-binding activity of the wild-type zcytor19 protein. Moreover, variant zcytor19 soluble receptors can be isolated. Such polypeptides may include additional amino acids from, for example, part or all of the transmembrane and intracellular domains. Such polypeptides may also include additional polypeptide segments as generally disclosed herein such as labels, affinity tags, and the like.

For any zcytor19 polypeptide, including variants, soluble receptors, and fusion polypeptides or proteins, one of ordinary skill in the art can readily generate a fully degenerate polynucleotide sequence encoding that variant using the information set forth in Tables 1 and 2 above.

The zcytor19 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual,* 2nd ed., Cold Spring Harbor Laboratory Press, Cold Spring Harbor, N.Y., 1989, and Ausubel et al., eds., *Current Protocols in Molecular Biology*, John Wiley and Sons, Inc., N.Y., 1987.

In general, a DNA sequence encoding a zcytor19 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zcytor19 polypeptide into the secretory pathway of a host cell, a secretory signal sequence (also known as a leader sequence, prepro sequence or pre sequence) is provided in the expression vector. The secretory signal sequence may be that of zcytor19, or may be derived from another secreted protein (e.g., t-PA) or synthesized de novo. The secretory signal sequence is operably linked to the zcytor19 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid 1 (Met) to amino acid 20 (Gly) of SEQ ID NO:2 or SEQ ID NO:19 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of a polypeptide fragment or an active component of a normally non-secreted protein. Such fusions may be used in vivo or in vitro to direct peptides through the secretory pathway. Moreover, such fusion constructs allow for the expression, secretion, and purification of zcytor19 polypepitde fragments that can be used to inoculate an animal and generate antibodies, as described herein.

Cultured mammalian cells are suitable hosts within the present invention. Methods for introducing exogenous DNA into mammalian host cells include calcium phosphate-mediated transfection (Wigler et al., Cell 14:725, 1978; Corsaro and Pearson, *Somatic Cell Genetics* 7:603, 1981: Graham and Van der Eb, Virology 52:456, 1973), electroporation (Neumann et al., EMBO J. 1:841-845, 1982), DEAE-dextran mediated transfection (Ausubel et al., ibid.), and liposome-mediated transfection (Hawley-Nelson et al., Focus 15:73, 1993; Ciccarone et al., Focus 15:80, 1993, and viral vectors (Miller and Rosman, BioTechniques 7:980-90, 1989; Wang and Finer, Nature Med. 2:714-716, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al, U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59-72, 1977) and Chinese hamster ovary (e.g. CHO-K1; ATCC No. CCL 61) cell lines. Additional suitable cell lines are known in the art and available from public depositories such as the American Type Culture Collection (ATCC), Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zcytor19 baculovirus utilizes a transposon-based system described by Luckow (Luckow, V. A, et al., *J Virol* 67:4566-79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zcytor19 polypeptide into a baculovirus genome maintained in *E. coli* as a large plasmid called a "bacmid." See, Hill-Perkins, M. S. and Possee, R. D., *J Gen Virol* 71:971-6, 1990; Bonning, B. C. et al., *J Gen Virol* 75:1551-6, 1994; and, Chazenbalk, G. D., and Rapoport, B., *J Biol Chem* 270:1543-9, 1995. In addition, transfer vectors can include an in-frame fusion with DNA encoding an epitope tag at the C- or N-terminus of the expressed zcytor19 polypeptide, for example, a Glu-Glu epitope tag (Grussenmeyer, T. et al., *Proc. Natl. Acad. Sci.* 82:7952-4, 1985). Using a technique known in the art, a transfer vector containing zcytor19 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zcytor19 is subsequently produced. Recombinant viral stocks are made by methods commonly used in the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. Procedures used are generally described in available laboratory manuals (King, L. A. and Possee, R. D., ibid.; O'Reilly, D. R. et al., ibid.; Richardson, C. D., ibid.). Subsequent purification of the zcytor19 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-3465, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zcytor19 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Within one aspect of the present invention, a zcytor19 cytokine receptor (including transmembrane and intracellular domains) is produced by a cultured cell, and the cell is used to screen for ligands for the receptor, including the natural ligand, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Mammalian cells suitable for use in expressing the novel receptors of the present invention and transducing a receptor-mediated signal include cells that express a β-subunit, such as a class II cytokine receptor subunit, for example, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511) receptors. Such subunits can either naturally be expressed in the cells, or be co-transfected with zcytor19 receptor. An exemplary cell system for class I cytokine receptors is to use cells that express gp130, and cells that co-express gp130 and LIF receptor (Gearing et al., *EMBO J.* 10:2839-2848, 1991; Gearing et al., U.S. Pat. No. 5,284,755). In this regard it is generally preferred to employ a cell that is responsive to other cytokines that bind to receptors in the same subfamily, such as IL-6 or LIF, because such cells will contain the requisite signal transduction pathway(s). Preferred cells of this type include BaF3 cells (Palacios and Steinmetz, *Cell* 41: 727-734, 1985; Mathey-Prevot et al., *Mol. Cell. Biol.* 6: 4133-4135, 1986), the human TF-1 cell line (ATCC number CRL-2003) and the DA-1 cell line (Branch et al., *Blood* 69:1782, 1987; Broudy et al., *Blood* 75:1622-1626, 1990). In the alternative, suitable host cells can be engineered to produce a β-subunit or other cellular component needed for the desired cellular response. For example, the murine cell line BaF3 (Palacios and Steinmetz, *Cell* 41:727-734, 1985; Mathey-Prevot et al., *Mol. Cell. Biol.* 6: 4133-4135, 1986), a baby hamster kidney (BHK) cell line, or the CTLL-2 cell line (ATCC TIB-214) can be transfected to express individual class II subunits such as, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511) receptors in addition to zcytor19. It is generally preferred to use a host cell and receptor(s) from the same species, however this approach allows cell lines to be engineered to express multiple receptor subunits from any species, thereby overcoming potential limitations arising from species specificity. In the alternative, species homologs of the human receptor cDNA can be cloned and used within cell lines from the same species, such as a mouse cDNA, in the BaF3 cell line. Cell lines that are dependent upon one hematopoietic growth factor, such as IL-3, can thus be engineered to become dependent upon a zcytor19 ligand or anti-zcytor19 antibody.

Cells expressing functional zcytor19 are used within screening assays. A variety of suitable assays are known in the art. These assays are based on the detection of a biological response in the target cell. One such assay is a cell proliferation assay. Cells are cultured in the presence or absence of a test compound, and cell proliferation is detected by, for example, measuring incorporation of tritiated thymidine or by colorimetric assay based on the reduction or metabolic breakdown of Alymar Blue™ (AccuMed, Chicago, Ill.) or 3-(4,5-dimethylthiazol-2-yl)-2,5-diphenyl tetrazolium bromide (MTT) (Mosman, *J. Immunol. Meth.* 65: 55-63, 1983). An alternative assay format uses cells that are further engineered to express a reporter gene. The reporter gene is linked to a promoter element that is responsive to the receptor-linked pathway, e.g, JAK/STAT pathway, and the assay detects activation of transcription of the reporter gene. A preferred promoter element in this regard is a serum response element, SRE (see, for example, Shaw et al., *Cell* 56:563-572, 1989). A preferred such reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:19094-29101, 1994; Schenborn and Goiffin, *Promega Notes* 41:11, 1993). Luciferase assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell- or tissue-conditioned media samples can be assayed on a target cell to identify cells that produce ligand. Positive cells are then used to produce a cDNA library in a mammalian cell expression vector, which is divided into pools, transfected into host cells, and expressed. Media samples from the transfected cells are then assayed, with subsequent division of pools, retransfection, subculturing, and re-assay of positive cells to isolate a clonal cell line expressing the ligand. Alternatively, media samples from the transfected cells can be assayed, with subsequent division of pools, retransfection, and re-assay to isolate a bacterial clone expressing the ligand cDNA. Media samples conditioned by kidney, liver, spleen, thymus, other lymphoid tissues, B-cells, T-cells, or leukemia cell lines are preferred sources of ligand for use in screening procedures.

A natural ligand for zcytor19 can also be identified by mutagenizing a cytokine-dependent cell line expressing zcytor19 and culturing it under conditions that select for autocrine growth. See WIPO publication WO 95/21930. Within a typical procedure, cells expressing zcytor19 are mutagenized, such as with EMS. The cells are then allowed to recover in the presence of the required cytokine, then transferred to a culture medium lacking the cytokine. Surviving cells are screened for the production of a ligand for zcytor19, such as by adding soluble receptor polypeptide comprising the zcytor19 extracellular cytokine-binding domain, or cytokine-binding fragment described herein to the culture medium to compete against the ligand or by assaying conditioned media on wild-type cells compared to transfected cells expressing the zcytor19 receptor. Preferred cell lines for use within this method include cells that are transfected to express gp130 or gp130 in combination with LIF receptor. Preferred such host cell lines include transfected CTLL-2 cells (Gillis and Smith, *Nature* 268:154-156, 1977) and transfected BaF3 cells.

Moreover, a secretion trap method employing zcytor19 soluble receptor polypeptide can be used to isolate a zcytor19 ligand (Aldrich, et al, *Cell* 87: 1161-1169, 1996). A cDNA expression library prepared from a known or suspected ligand source is transfected into COS-7 cells. The cDNA library vector generally has an SV40 origin for amplification in COS-7 cells, and a CMV promoter for high expression. The transfected COS-7 cells are grown in a monolayer and then fixed and permeabilized. Tagged or biotin-labeled zcytor19 soluble receptor, described herein, is then placed in contact with the cell layer and allowed to bind cells in the monolayer that express an anti-complementary molecule, i.e., a zcytor19 ligand. A cell expressing a ligand will thus be bound with receptor molecules. An anti-tag antibody (anti-Ig for Ig fusions, M2 or anti-FLAG for FLAG-tagged fusions, streptavidin, anti-Glu-Glu tag, and the like) which is conjugated with horseradish peroxidase (HRP) is used to visualize these cells to which the tagged or biotin-labeled zcytor19 soluble receptor has bound. The HRP catalyzes deposition of a tyramide reagent, for example, tyramide-FITC. A commercially-available kit can be used for this detection (for example, Renaissance TSA-Direct™ Kit; NEN Life Science Products, Boston, Mass.). Cells which express zcytor19 receptor ligand will be identified under fluorescence microscopy as green cells and picked for subsequent cloning of the ligand using procedures for plasmid rescue as outlined in Aldrich, et al, supra., followed by subsequent rounds of secretion trap assay, or conventional screening of cDNA library pools, until single clones are identified.

As a receptor, the activity of zcytor19 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol.* 228:84-108, 1997; Arimilli, S. et al., *J. Immunol. Meth.* 212:49-59, 1998; Van Liefde, I. Et al., *Eur. J. Pharmacol.* 346:87-95, 1998. The microphysiometer can be used for assaying eukaryotic, prokaryotic, adherent or non-adherent cells. By measuring extracellular acidification changes in cell media over time, the microphysiometer directly measures cellular responses to various stimuli, including agonists, ligands, or antagonists of the zcytor19 polypeptide. Preferably, the microphysiometer is used to measure responses of a zcytor19-expressing eukaryotic cell, compared to a control eukaryotic cell that does not express zcytor19 polypeptide. Zcytor19-expressing eukaryotic cells comprise cells into which zcytor19 has been transfected or infected via adenovirus vector, and the like, as described herein, creating a cell that is responsive to zcytor19-modulating stimuli, or are cells naturally expressing zcytor19, such as zcytor19-expressing cells derived from lymphoid, spleen, thymus tissue or PBLs. Differences, measured by an increase or decrease in extracellular acidification, in the response of cells expressing zcytor19, relative to a control, are a direct measurement of zcytor19-modulated cellular responses. Moreover, such zcytor19-modulated responses can be assayed under a variety of stimuli. Also, using the microphysiometer, there is provided a method of identifying agonists and antagonists of zcytor19 polypeptide, comprising providing cells expressing a zcytor19 polypeptide, culturing a first portion of the cells in the absence of a test compound, culturing a second portion of the cells in the presence of a test compound, and detecting an increase or a decrease in a cellular response of the second portion of the cells as compared to the first portion of the cells. Antagonists and agonists, including the natural ligand for zcytor19 polypeptide, can be rapidly identified using this method.

Additional assays provided by the present invention include the use of hybrid receptor polypeptides. These hybrid polypeptides fall into two general classes. Within the first class, the intracellular domain of zcytor19, comprising approximately residues 250 (Lys) to 491 (Arg) of SEQ ID NO:2 or residues 250 (Lys) to 520 (Arg) of SEQ ID NO:19), is joined to the ligand-binding domain of a second receptor. It is preferred that the second receptor be a hematopoietic cytokine receptor, such as mp1 receptor (Souyri et al., *Cell* 63:1137-1147, 1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by zcytor19 while using readily available ligands. This system can also be used to determine if particular cell lines are capable of responding to signals transduced by zcytor19. A second class of hybrid receptor polypeptides comprise the extracellular (ligand-binding) cytokine-binding domain (residues 21 (Arg) to 226 (Asn) of SEQ ID NO:2 or SEQ ID NO:19), or cytokine-binding fragment (e.g., residues 21 (Arg) to 223 (Pro) of SEQ ID NO:2 or SEQ ID NO:19; SEQ ID NO:4) with a cytoplasmic domain of a second receptor, preferably a cytokine receptor, and a transmembrane domain. The transmembrane domain may be derived from either receptor. Hybrid receptors of this second class are expressed in cells known to be capable of responding to signals transduced by the second receptor. Together, these two classes of hybrid receptors enable the use of a broad spectrum of cell types within receptor-based assay systems.

Cells found to express a ligand for zcytor19 are then used to prepare a cDNA library from which the ligand-encoding cDNA may be isolated as disclosed above. The present invention thus provides, in addition to novel receptor polypeptides, methods for cloning polypeptide ligands for the receptors.

The zcytor19 structure and tissue expression suggests a role in early hematopoietic or thymocyte development and immune response regulation. These processes involve stimulation of cell proliferation and differentiation in response to the binding of one or more cytokines to their cognate receptors. In view of the tissue distribution observed for this receptor, agonists (including the natural ligand) and antagonists have enormous potential in both in vitro and in vivo applications. Compounds identified as receptor agonists are useful for stimulating proliferation and development of target cells in vitro and in vivo. For example, agonist compounds or antizcytor19 antibodies, are useful as components of defined cell culture media, and may be used alone or in combination with other cytokines and hormones to replace serum that is commonly used in cell culture. Agonists are thus useful in specifically promoting the growth and/or development of T-cells, B-cells, and other cells of the lymphoid and myeloid lineages, and hematopoietic cells in culture.

Agonist ligands for zcytor19, or anti-zcytor19 antibodies, may be useful in stimulating cell-mediated immunity and for stimulating lymphocyte proliferation, such as in the treatment of infections involving immunosuppression, including certain viral infections. Additional uses include tumor suppression, where malignant transformation results in tumor cells that are antigenic. Agonist ligands or anti-zcytor19 antibodies could be used to induce cytotoxicity, which may be mediated through activation of effector cells such as T-cells, NK (natural killer) cells, or LAK (lymphoid activated killer) cells, or induced directly through apoptotic pathways. For example, zcytor19 antibodies could be used for stimulating cytotoxicity or ADCC on zcytor19-bearing cancer cells. Agonist ligands may also be useful in treating leukopenias by increasing the levels of the affected cell type, and for enhancing the regeneration of the T-cell repertoire after bone marrow transplantation.

Antagonist ligands, compounds, soluble zcytor19 receptors, or anti-zcytor19 antibodies may find utility in the suppression of the immune system, such as in the treatment of autoimmune diseases, including rheumatoid arthritis, multiple sclerosis, diabetes mellitis, inflammatory bowel disease, Crohn's disease, etc. Immune suppression can also be used to reduce rejection of tissue or organ transplants and grafts and to treat T-cell specific leukemias or lymphomas by inhibiting proliferation of the affected cell type.

The present invention contemplates the use of naked anti-zcytor19 antibodies (or naked antibody fragments thereof), as well as the use of immunoconjugates to effect treatment of various disorders, including B-cell malignancies and other cancers described herein wherein zcytor19 is expressed. Such immunoconjugates as well as anti-zcytor19 antibodies can be used for stimulating cytotoxicity or ADCC on zcytor19-bearing cancer cells. Immunoconjugates can be prepared using standard techniques. For example, immunoconjugates can be produced by indirectly conjugating a therapeutic agent to an antibody component (see, for example, Shih et al., *Int. J. Cancer* 41:832-839 (1988); Shih et al., *Int. J. Cancer* 46:1101-1106 (1990); and Shih et al., U.S. Pat. No. 5,057,313). Briefly, one standard approach involves reacting an antibody component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer can be an aminodextran or polypeptide of at least 50 amino acid residues, although other substantially equivalent polymer carriers can also be used. Preferably, the final immunoconjugate is soluble in an aqueous solution, such as mammalian serum, for ease of administration and effective targeting for use in therapy. Thus, solubilizing functions on the carrier polymer will enhance the serum solubility of the final immunoconjugate.

In an alternative approach for producing immunoconjugates comprising a polypeptide therapeutic agent, the therapeutic agent is coupled to aminodextran by glutaraldehyde condensation or by reaction of activated carboxyl groups on the polypeptide with amines on the aminodextran. Chelators can be attached to an antibody component to prepare immunoconjugates comprising radiometals or magnetic resonance enhancers. Illustrative chelators include derivatives of ethylenediaminetetraacetic acid and diethylenetriaminepentaacetic acid. Boron addends, such as carboranes, can be attached to antibody components by conventional methods.

Immunoconjugates can also be prepared by directly conjugating an antibody component with a therapeutic agent. The general procedure is analogous to the indirect method of conjugation except that a therapeutic agent is directly attached to an oxidized antibody component.

As a further illustration, a therapeutic agent can be attached at the hinge region of a reduced antibody component via disulfide bond formation. For example, the tetanus toxoid peptides can be constructed with a single cysteine residue that is used to attach the peptide to an antibody component. As an alternative, such peptides can be attached to the antibody component using a heterobifunctional cross-linker, such as N-succinyl 3-(2-pyridyldithio)proprionate. Yu et al., *Int. J. Cancer* 56:244 (1994). General techniques for such conjugation are well-known in the art. See, for example, Wong, *Chemistry Of Protein Conjugation And Cross-Linking* (CRC Press 1991); Upeslacis et al., "Modification of Antibodies by Chemical Methods," in *Monoclonal Antibodies: Principles And Applications*, Birch et al. (eds.), pages 187-230 (Wiley-Liss, Inc. 1995); Price, "Production and Characterization of Synthetic Peptide-Derived Antibodies," in *Monoclonal Antibodies: Production, Engineering And Clinical Application*, Ritter et al. (eds.), pages 60-84 (Cambridge University Press 1995).

As described above, carbohydrate moieties in the Fc region of an antibody can be used to conjugate a therapeutic agent. However, the Fc region is absent if an antibody fragment is used as the antibody component of the immunoconjugate. Nevertheless, it is possible to introduce a carbohydrate moiety into the light chain variable region of an antibody or antibody fragment. See, for example, Leung et al., *J Immunol.* 154:5919 (1995); Hansen et al., U.S. Pat. No. 5,443,953 (1995). The engineered carbohydrate moiety is then used to attach a therapeutic agent.

In addition, those of skill in the art will recognize numerous possible variations of the conjugation methods. For example, the carbohydrate moiety can be used to attach polyethyleneglycol in order to extend the half-life of an intact antibody, or antigen-binding fragment thereof, in blood, lymph, or other extracellular fluids. Moreover, it is possible to construct a divalent immunoconjugate by attaching therapeutic agents to a carbohydrate moiety and to a free sulfhydryl group. Such a free sulfhydryl group may be located in the hinge region of the antibody component.

One type of immunoconjugate comprises an antibody component and a polypeptide cytotoxin. An example of a suitable polypeptide cytotoxin is a ribosome-inactivating protein. Type I ribosome-inactivating proteins are single-chain proteins, while type II ribosome-inactivating proteins consist of two nonidentical subunits (A and B chains) joined by a disulfide bond (for a review, see Soria et al., *Targeted Diagn. Ther.* 7:193 (1992)). Useful type I ribosome-inactivating proteins include polypeptides from *Saponaria officinalis* (e.g., saporin-1, saporin-2, saporin-3, saporin-6), *Momordica charantia* (e.g, momordin), *Byronia dioica* (e.g., bryodin, bryodin-2), *Trichosanthes kirilowii* (e.g., trichosanthin, trichokirin), *Gelonium multiflorum* (e.g., gelonin), *Phytolacca americana* (e.g., pokeweed antiviral protein, pokeweed antiviral protein-II, pokeweed antiviral protein-S), *Phytolacca dodecandra* (e.g., dodecandrin, *Mirabilis* antiviral protein), and the like. Ribosome-inactivating proteins are described, for example, by Walsh et al., U.S. Pat. No. 5,635,384.

Suitable type II ribosome-inactivating proteins include polypeptides from *Ricinus communis* (e.g., ricin), *Abrus precatorius* (e.g., abrin), *Adenia digitata* (e.g., modeccin), and the like. Since type II ribosome-inactiving proteins include a B chain that binds galactosides and a toxic A chain that depurinates adensoine, type II ribosome-inactivating protein conjugates should include the A chain. Additional useful ribosome-inactivating proteins include bouganin, clavin, maize ribosome-inactivating proteins, *Vaccaria pyramidata* ribosome-inactivating proteins, nigrine b, basic nigrine 1, ebuline, racemosine b, luffin-a, luffin-b, luffin-S, and other ribosome-inactivating proteins known to those of skill in the art. See, for example, Bolognesi and Stirpe, international publication No. WO98/55623, Colnaghi et al., international publication No. WO97/49726, Hey et al., U.S. Pat. No. 5,635, 384, Bolognesi and Stirpe, international publication No. WO95/07297, Arias et al., international publication No. WO94/20540, Watanabe et al., *J. Biochem.* 106:6 977 (1989); Islam et al., *Agric. Biol. Chem.* 55:229 (1991), and Gao et al., *FEBS Lett.* 347:257 (1994).

Analogs and variants of naturally-occurring ribosome-inactivating proteins are also suitable for the targeting compositions described herein, and such proteins are known to those of skill in the art. Ribosome-inactivating proteins can be produced using publicly available amino acid and nucleotide sequences. As an illustration, a nucleotide sequence encoding saporin-6 is disclosed by Lorenzetti et al., U.S. Pat. No. 5,529,932, while Walsh et al., U.S. Pat. No. 5,635,384, describe maize and barley ribosome-inactivating protein nucleotide and amino acid sequences. Moreover, ribosome-inactivating proteins are also commercially available.

Additional polypeptide cytotoxins include ribonuclease, DNase I, Staphylococcal enterotoxin-A, diphtheria toxin, *Pseudomonas* exotoxin, and *Pseudomonas* endotoxin. See, for example, Pastan et al., *Cell* 47:641 (1986), and Goldenberg, *CA—A Cancer Journal for Clinicians* 44:43 (1994).

Another general type of useful cytotoxin is a tyrosine kinase inhibitor. Since the activation of proliferation by tyrosine kinases has been suggested to play a role in the development and progression of tumors, this activation can be inhibited by anti-zcytor19 antibody components that deliver tyrosine kinase inhibitors. Suitable tyrosine kinase inhibitors include isoflavones, such as genistein (5, 7, 4'-trihydroxyisoflavone), daidzein (7,4'-dihydroxyisoflavone), and biochanin A (4-methoxygenistein), and the like. Methods of conjugating tyrosine inhibitors to a growth factor are described, for example, by Uckun, U.S. Pat. No. 5,911,995.

Another group of useful polypeptide cytotoxins includes immunomodulators. As used herein, the term "immunomodulator" includes cytokines, stem cell growth factors, lymphotoxins, co-stimulatory molecules, hematopoietic factors, and the like, as well as synthetic analogs of these molecules. Examples of immunomodulators include tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, and IL-20), colony stimulating factors (e.g., granulocyte-colony stimulating factor and granulocyte macrophage-colony stimulating factor), interferons (e.g., interferons-α, -β, -γ, -ω, -ε, and -τ), the stem cell growth factor designated "S1 factor," erythropoietin, and thrombopoietin. Illustrative immunomodulator moieties include IL-2, IL-6, IL-10, interferon-□, TNF-□, and the like.

Immunoconjugates that include an immunomodulator provide a means to deliver an immunomodulator to a target cell, and are particularly useful against tumor cells. The cytotoxic effects of immunomodulators are well known to those of skill in the art. See, for example, Klegerman et al., "Lymphokines and Monokines," in *Biotechnology And Pharmacy*, Pessuto et al. (eds.), pages 53-70 (Chapman & Hall 1993). As an illustration, interferons can inhibit cell proliferation by inducing increased expression of class I histocompatibility antigens on the surface of various cells and thus, enhance the rate of destruction of cells by cytotoxic T lymphocytes. Furthermore, tumor necrosis factors, such as tumor necrosis factor-α, are believed to produce cytotoxic effects by inducing DNA fragmentation.

The present invention also includes immunocongugates that comprise a nucleic acid molecule encoding a cytotoxin. As an example of this approach, Hoganson et al., *Human Gene Ther.* 9:2565 (1998), describe FGF-2 mediated delivery of a saporin gene by producing an FGF-2-polylysine conjugate which was condensed with an expression vector comprising a saporin gene.

Other suitable toxins are known to those of skill in the art.

Conjugates of cytotoxic polypeptides and antibody components can be prepared using standard techniques for conjugating polypeptides. For example, Lam and Kelleher, U.S. Pat. No. 5,055,291, describe the production of antibodies conjugated with either diphtheria toxin fragment A or ricin toxin. The general approach is also illustrated by methods of conjugating fibroblast growth factor with saporin, as described by Lappi et al., *Biochem. Biophys. Res. Comm n.* 160:917 (1989), Soria et al., *Targeted Diagn. Ther.* 7:193 (1992), Buechler et al., *Eur. J. Biochem.* 234:706 (1995), Behar-Cohen et al., *Invest. Ophthalmol. Vis. Sci.* 36:2434 (1995), Lappi and Baird, U.S. Pat. No. 5,191,067, Calabresi et al., U.S. Pat. No. 5,478,804, and Lappi and Baird, U.S. Pat. No. 5,576,288. Also see, Ghetie and Vitteta, "Chemical Construction of Immunotoxins," in *Drug Targeting: Strategies, Principles, and Applications*, Francis and Delgado (Eds.), pages 1-26 (Humana Press, Inc. 2000), Hall (Ed.), *Immunotoxin Methods and Protocols* (Humana Press, Inc. 2000), and Newton and Rybak, "Construction of Ribonuclease-Antibody Conjugates for Selective Cytotoxicity," in *Drug Targeting: Strategies, Principles, and Applications*, Francis and Delgado (Eds.), pages 27-35 (Humana Press, Inc. 2000).

Alternatively, fusion proteins comprising an antibody component and a cytotoxic polypeptide can be produced using standard methods. Methods of preparing fusion proteins comprising a cytotoxic polypeptide moiety are well-known in the art of antibody-toxin fusion protein production. For example, antibody fusion proteins comprising an interleukin-2 moiety are described by Boleti et al., *Ann. Oncol.* 6:945 (1995), Nicolet et al., *Cancer Gene Ther.* 2:161 (1995), Becker et al., *Proc. Natl. Acad. Sci. USA* 93:7826 (1996), Hank et al., *Clin. Cancer Res.* 2:1951 (1996), and Hu et al., *Cancer Res.* 56:4998 (1996). In addition, Yang et al., *Hum. Antibodies Hybridomas* 6:129 (1995), describe a fusion protein that includes an $F(ab')_2$ fragment and a tumor necrosis factor alpha moiety. Antibody-*Pseudomonas* exotoxin A fusion proteins have been described by Chaudhary et al., *Nature* 339:394 (1989), Brinkmann et al., *Proc. Nat'l Acad. Sci. USA* 88:8616 (1991), Batra et al., *Proc. Nat'l Acad. Sci. USA* 89:5867 (1992), Friedman et al., *J. Immunol.* 150:3054 (1993), Wels et al., *Int. J. Can.* 60:137 (1995), Fominaya et al., *J. Biol. Chem.* 271:10560 (1996), Kuan et al., *Biochemistry* 35:2872 (1996), and Schmidt et al., *Int. J. Can.* 65:538 (1996). Antibody-toxin fusion proteins containing a diphtheria toxin moiety have been described by Kreitman et al., *Leukemia* 7:553 (1993), Nicholls et al., *J. Biol. Chem.* 268:5302 (1993), Thompson et al., *J. Biol. Chem.* 270:28037 (1995), and Vallera et al., *Blood* 88:2342 (1996). Deonarain et al., *Tumor Targeting* 1:177 (1995), have described an antibody-toxin fusion protein having an RNase moiety, while Linardou et al., *Cell Biophys.* 24-25:243 (1994), produced an antibody-toxin fusion protein comprising a DNase I component. Gelonin was used as the toxin moiety in the antibody-toxin fusion protein of Better et al., *J. Biol. Chem.* 270:14951 (1995). As a further example, Dohlsten et al., *Proc. Natl. Acad. Sci. USA* 91:8945 (1994), reported an antibody-toxin fusion protein comprising Staphylococcal enterotoxin-A. Also see, Newton and Rybak, "Preparation of Recombinant RNase Single-Chain Antibody Fusion Proteins," in *Drug Targeting: Strategies, Principles, and Applications*, Francis and Delgado (Eds.), pages 77-95 (Humana Press, Inc. 2000).

As an alternative to a polypeptide cytotoxin, immunoconjugates can comprise a radioisotope as the cytotoxic moiety.

For example, an immunoconjugate can comprise an anti-zcytor19 antibody component and an α-emitting radioisotope, a β-emitting radioisotope, a γ-emitting radioisotope, an Auger electron emitter, a neutron capturing agent that emits α-particles or a radioisotope that decays by electron capture. Suitable radioisotopes include $^{198}$Au, $^{199}$Au, $^{32}$P, $^{33}$P, $^{125}$I, $^{131}$I, $^{123}$I, $^{90}$Y, $^{186}$Re, $^{188}$Re, $^{67}$Cu, $^{211}$At, $^{47}$Sc, $^{103}$Pb, $^{109}$Pd, $^{212}$Pb, $^{71}$Ge, $^{77}$As, $^{105}$Rh, $^{113}$Ag, $^{119}$Sb, $^{121}$Sn, $^{131}$Cs, $^{143}$Pr, $^{161}$Tb, $^{177}$Lu, $^{191}$Os, $^{193M}$Pt, $^{197}$Hg, and the like.

A radioisotope can be attached to an antibody component directly or indirectly, via a chelating agent. For example, $^{67}$Cu, which provides β-particles and γ-rays, can be conjugated to an antibody component using the chelating agent, p-bromoacetamido-benzyl-tetraethylaminetetraacetic acid. Chase and Shapiro, "Medical Applications of Radioisotopes," in Gennaro (Ed.), *Remington: The Science and Practice of Pharmacy,* 19th Edition, pages 843-865 (Mack Publishing Company 1995). As an alternative, $^{90}$Y, which emits an energetic β-particle, can be coupled to an antibody component using diethylenetriaminepentaacetic acid. Moreover, an exemplary suitable method for the direct radiolabeling of an antibody component with $^{131}$I is described by Stein et al., *Antibody Immunoconj. Radiopharm.* 4:703 (1991). Alternatively, boron addends such as carboranes can be attached to antibody components, using standard techniques.

Another type of suitable cytotoxin for the preparation of immunoconjugates is a chemotherapeutic drug. Illustrative chemotherapeutic drugs include nitrogen mustards, alkyl sulfonates, nitrosoureas, triazenes, folic acid analogs, pyrimidine analogs, purine analogs, antibiotics, epipodophyllotoxins, platinum coordination complexes, and the like. Specific examples of chemotherapeutic drugs include methotrexate, doxorubicin, daunorubicin, cytosinarabinoside, cis-platin, vindesine, mitomycin, bleomycin, melphalan, chlorambucil, maytansinoids, calicheamicin, taxol, and the like. Suitable chemotherapeutic agents are described in *Remington: The Science and Practice of Pharmacy,* 19th Edition (Mack Publishing Co. 1995), and in *Goodman And Gilman's The Pharmacological Basis Of Therapeutics,* 9th Ed. (MacMillan Publishing Co. 1995). Other suitable chemotherapeutic agents are known to those of skill in the art.

In another approach, immunoconjugates are prepared by conjugating photoactive agents or dyes to an antibody component. Fluorescent and other chromogens, or dyes, such as porphyrins sensitive to visible light, have been used to detect and to treat lesions by directing the suitable light to the lesion. This type of "photoradiation," "phototherapy," or "photodynamic" therapy is described, for example, by Mew et al., *J Immunol.* 130:1473 (1983), Jori et al. (eds.), *Photodynamic Therapy Of Tumors And Other Diseases* (Libreria Progetto 1985), Oseroff et al., *Proc. Natl. Acad. Sci. USA* 83:8744 (1986), van den Bergh, *Chem. Britain* 22:430 (1986), Hasan et al., *Prog. Clin. Biol. Res.* 288:471 (1989), Tatsuta et al., *Lasers Surg. Med.* 9:422 (1989), and Pelegrin et al., *Cancer* 67:2529 (1991).

The approaches described above can also be used to prepare multispecific antibody compositions that comprise an immunoconjugate.

Anti-zcytor19 antibodies and multispecific antibody compositions can be used to modulate the immune system by preventing the binding of zcytor19 ligands with endogenous zcytor19 receptors. Such antibodies can be administered to any subject in need of treatment, and the present invention contemplates both veterinary and human therapeutic uses. Illustrative subjects include mammalian subjects, such as farm animals, domestic animals, and human patients.

Multispecific antibody compositions and dual reactive antibodies that bind zcytor19 can be used for the treatment of autoimmune diseases, B cell cancers, immunomodulation, and other pathologies (e.g., ITCP, T cell-mediated diseases, cattleman's disease, autoimmune disease, myelodysplastic syndrome, and the like), renal diseases, graft rejection, and graft versus host disease. The antibodies of the present invention can be targeted to specifically regulate B cell responses during the immune response. Additionally, the antibodies of the present invention can be used to modulate B cell development, antigen presentation by B cells, antibody production, and cytokine production.

Antagonistic anti-zcytor19 antibodies can be useful to neutralize the effects of zcytor19 ligands for treating B cell lymphomas and leukemias, chronic or acute lymphocytic leukemia, myelomas such as multiple myeloma, plasma cytomas, and lymphomas such as non-Hodgkins lymphoma, for which an increase in zcytor19 ligand polypeptides is associated, or where zcytor19 ligand is a survival factor or growth factor. Anti-zcytor19 antibodies can also be used to treat Epstein Barr virus-associated lymphomas arising in immunocompromised patients (e.g., AIDS or organ transplant).

Anti-zcytor19 antibodies that induce a signal by binding with zcytor19 may inhibit the growth of lymphoma and leukemia cells directly via induction of signals that lead to growth inhibition, cell cycle arrest, apoptosis, or tumor cell death. Zcytor19 antibodies that initiate a signal are preferred antibodies to directly inhibit or kill cancer cells. In addition, agonistic anti-zcytor19 monoclonal antibodies may activate normal B cells and promote an anticancer immune response. Anti-zcytor19 antibodies may directly inhibit the growth of leukemias, lymphomas, and multiple myelomas, and the antibodies may engage immune effector functions. Anti-zcytor19 monoclonal antibodies may enable antibody-dependent cellular cytotoxicity, complement dependent cytotoxicity, and phagocytosis.

zcytor19 ligand may be expressed in neutrophils, monocytes, dendritic cells, and activated monocytes. In certain autoimmune disorders (e.g., myasthenia gravis, and rheumatoid arthritis), B cells might exacerbate autoimmunity after activation by zcytor19 ligand. Immunosuppressant proteins that selectively block the action of B-lymphocytes would be of use in treating disease. Autoantibody production is common to several autoimmune diseases and contributes to tissue destruction and exacerbation of disease. Autoantibodies can also lead to the occurrence of immune complex deposition complications and lead to many symptoms of systemic lupus erythematosus, including kidney failure, neuralgic symptoms and death. Modulating antibody production independent of cellular response would also be beneficial in many disease states. B cells have also been shown to play a role in the secretion of arthritogenic immunoglobulins in rheumatoid arthritis. As such, inhibition of zcytor19 ligand antibody production would be beneficial in treatment of autoimmune diseases such as myasthenia gravis and rheumatoid arthritis. Immunosuppressant therapeutics such as anti-zcytor19 antibodies that selectively block or neutralize the action of B-lymphocytes would be useful for such purposes.

The invention provides methods employing anti-zcytor19 antibodies, or multispecific antibody compositions, for selectively blocking or neutralizing the actions of B-cells in association with end stage renal diseases, which may or may not be associated with autoimmune diseases. Such methods would also be useful for treating immunologic renal diseases. Such methods would be would be useful for treating glomerulonephritis associated with diseases such as membranous nephropathy, IgA nephropathy or Berger's Disease, IgM nephropathy, Goodpasture's Disease, post-infectious glomerulonephritis, mesangioproliferative disease, chronic lymphocytic leukemia, minimal-change nephrotic syndrome. Such methods would also serve as therapeutic applications for treating secondary glomerulonephritis or vasculitis associated with such diseases as lupus, polyarteritis, Henoch-Schonlein, Scleroderma, HIV-related diseases, amyloidosis or hemolytic uremic syndrome. The methods of the present invention would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis.

The present invention also provides methods for treatment of renal or urological neoplasms, multiple myelomas, lymphomas, leukemias, light chain neuropathy, or amyloidosis.

The invention also provides methods for blocking or inhibiting activated B cells using anti-zcytor19 antibodies, or multispecific antibody compositions, for the treatment of asthma and other chronic airway diseases such as bronchitis and emphysema.

Also provided are methods for inhibiting or neutralizing a T cell response using anti-zcytor19 antibodies, or multispecific antibody compositions, for immunosuppression, in particular for such therapeutic use as for graft-versus-host disease and graft rejection. Moreover, anti-zcytor19 antibodies, or multispecific antibody compositions, would be useful in therapeutic protocols for treatment of such autoimmune diseases as insulin dependent diabetes mellitus (IDDM), multiple sclerosis, rheumatoid arthritis, systemic lupus erythematosus, inflammatory bowel disease (IBD), and Crohn's Disease. Methods of the present invention would have additional therapeutic value for treating chronic inflammatory diseases, in particular to lessen joint pain, swelling, anemia and other associated symptoms as well as treating septic shock.

B cell responses are important in fighting infectious diseases including bacterial, viral, protozoan and parasitic infections. Antibodies against infectious microorganisms can immobilize the pathogen by binding to antigen followed by complement mediated lysis or cell mediated attack. Agonistic, or signaling, anti-zcytor19 antibodies may serve to boost the humoral response and would be a useful therapeutic for individuals at risk for an infectious disease or as a supplement to vaccination.

Well established animal models are available to test in vivo efficacy of anti-zcytor19 antibodies, or multispecific antibody compositions, of the present invention in certain disease states. As an illustration, anti-zcytor19 antibodies can be tested in vivo in a number of animal models of autoimmune disease, such as MRL-lpr/lpr or NZB×NZW F1 congenic mouse strains which serve as a model of systemic lupus erythematosus. Such animal models are known in the art.

Offspring of a cross between New Zealand Black (NZB) and New Zealand White (NZW) mice develop a spontaneous form of systemic lupus erythematosus that closely resembles systemic lupus erythematosus in humans. The offspring mice, known as NZBW begin to develop IgM autoantibodies against T-cells at one month of age, and by 5-7 months of age, Ig anti-DNA autoantibodies are the dominant immunoglobulin. Polyclonal B-cell hyperactivity leads to overproduction of autoantibodies. The deposition of these autoantibodies, particularly ones directed against single stranded DNA is associated with the development of glomerulonephritis, which manifests clinically as proteinuria, azotemia, and death from renal failure. Kidney failure is the leading cause of death in mice affected with spontaneous systemic lupus erythematosus, and in the NZBW strain, this process is chronic and obliterative. The disease is more rapid and severe in females than males, with mean survival of only 245 days as compared to 406 days for the males. While many of the female mice will be symptomatic (proteinuria) by 7-9 months of age, some can be much younger or older when they develop symptoms. The fatal immune nephritis seen in the NZBW mice is very similar to the glomerulonephritis seen in human systemic lupus erythematosus, making this spontaneous murine model useful for testing of potential systemic lupus erythematosus therapeutics.

Murine models of experimental allergic encephalomyelitis have been used as tools to investigate both the mechanisms of immune-mediated disease, and methods of potential therapeutic intervention. The model resembles human multiple sclerosis, and produces demyelination as a result of T-cell activation to neural proteins such as myelin basic protein, or proteolipid protein. Inoculation with antigen leads to induction of CD4+, class II MHC-restricted T-cells. Changes in the protocol for experimental allergic encephalomyelitis can produce acute, chronic-relapsing, or passive-transfer variants of the model.

In the collagen-induced arthritis model, mice develop chronic inflammatory arthritis, which closely resembles human rheumatoid arthritis. Since collagen-induced arthritis shares similar immunological and pathological features with rheumatoid arthritis, this makes it an ideal model for screening potential human anti-inflammatory compounds. Another advantage in using the collagen-induced arthritis model is that the mechanisms of pathogenesis are known. The T and B cell epitopes on type II collagen have been identified, and various immunological (delayed-type hypersensitivity and anti-collagen antibody) and inflammatory (cytokines, chemokines, and matrix-degrading enzymes) parameters relating to immune-mediating arthritis have been determined, and can be used to assess test compound efficacy in the models.

Myasthenia gravis is another autoimmune disease for which murine models are available. Myasthenia gravis is a disorder of neuromuscular transmission involving the production of autoantibodies directed against the nicotinic acetylcholine receptor. Myasthenia gravis is acquired or inherited with clinical features including abnormal weakness and fatigue on exertion. A mouse model of myasthenia gravis have been established. Experimental autoimmune myasthenia gravis is an antibody mediated disease characterized by the presence of antibodies to acetylcholine receptor. These antibodies destroy the receptor leading to defective neuromuscular electrical impulses, resulting in muscle weakness. In the experimental autoimmune myasthenia gravis model, mice are immunized with the nicotinic acetylcholine receptor. Clinical signs of myasthenia gravis become evident weeks after the second immunization. Experimental autoimmune myasthenia gravis is evaluated by several methods including measuring serum levels of acetylcholine receptor antibodies by radioimmunoassay, measuring muscle acetylcholine receptor, or electromyography.

Generally, the dosage of administered anti-zcytor19 antibodies, or multispecific antibody compositions, will vary depending upon such factors as the subject's age, weight, height, sex, general medical condition and previous medical history. As an illustration, anti-zcytor19 antibodies, or multispecific antibody compositions, can be administered at low protein doses, such as 20 to 100 milligrams protein per dose, given once, or repeatedly. Alternatively, anti-zcytor19 antibodies, or multispecific antibody compositions, can be administered in doses of 30 to 90 milligrams protein per dose, or 40 to 80 milligrams protein per dose, or 50 to 70 milligrams protein per dose, although a lower or higher dosage also may be administered as circumstances dictate.

Administration of antibody components to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses. Additional routes of administration include oral, mucosal-membrane, pulmonary, and transcutaneous.

A pharmaceutical composition comprising an anti-zcytor19 antibody, or bispecific antibody components, can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, anti-zcytor19 antibodies, or bispecific antibody components, and a pharmaceutically acceptable carrier are administered to a patient in a therapeutically effective amount. A combination of anti-zcytor19 antibodies, or bispecific antibody components, and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response. As another example, an agent used to inhibit the growth of tumor cells is physiologically significant if the administration of the agent results in a decrease in the number of tumor cells, decreased metastasis, a decrease in the size of a solid tumor, or increased necrosis of a tumor.

A pharmaceutical composition comprising anti-zcytor19 antibodies, or bispecific antibody components, can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Those of skill in the art can devise various pharmaceutical compositions using standard techniques. See, for example, Lieberman et al., (Eds.), *Pharmaceutical Dosage Forms: Tablets, Vol.* 1, *2nd Edition* (Marcel Dekker, Inc. 1989), Lieberman et al., (Eds.), *Pharmaceutical Dosage Forms: Tablets, Vol.* 2, *2nd Edition* (Marcel Dekker, Inc. 1990), Lieberman et al., (Eds.), *Pharmaceutical Dosage Forms: Tablets, Vol.* 3, *2nd Edition* (Marcel Dekker, Inc. 1990), Lieberman et al., (Eds.), *Pharmaceutical Dosage Forms: Disperse Systems, Vol.* 1, 2nd Edition (Marcel Dekker, Inc. 1996), Lieberman et al., (Eds.), *Pharmaceutical Dosage Forms: Disperse Systems, Vol.* 2, 2nd Edition (Marcel Dekker, Inc. 1996), Lieberman et al., (Eds.), *Pharmaceutical Dosage Forms: Disperse Systems, Vol.* 3, *2nd Edition* (Marcel Dekker, Inc. 1998), Avis et al., (Eds.), *Pharmaceutical Dosage Forms: Parenteral Medications, Vol.* 1, *2nd Edition* (Marcel Dekker, Inc. 1991), Lieberman et al., (Eds.), *Pharmaceutical Dosage Forms: Parenteral Medications, Vol.* 2, *2nd Edition* (Marcel Dekker, Inc. 1992), and Avis et al., (Eds.), *Pharmaceutical Dosage Forms: Parenteral Medications, Vol.* 3, *2nd Edition* (Marcel Dekker, Inc. 1993).

As another example, liposomes provide a means to deliver anti-zcytor19 antibodies, or bispecific antibody components, to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (Eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

As an alternative to administering liposomes that comprise an anti-zcytor19 antibody component, target cells can be prelabeled with biotinylated anti-zcytor19 antibodies. After plasma elimination of free antibody, streptavidin-conjugated liposomes are administered. This general approach is described, for example, by Harasym et al., *Adv. Drug Deliv.*

*Rev.* 32:99 (1998). Such an approach can also be used to prepare multispecific antibody compositions.

Polypeptides comprising an anti-zcytor19 antibody component, or bispecific antibody components, can be encapsulated within liposomes, or attached to the exterior of liposomes, using standard techniques (see, for example, Anderson et al., *Infect. Immun.* 31:1099 (1981), Wassef et al., *Meth. Enzymol.* 149:124 (1987), Anderson et al., *Cancer Res.* 50:1853 (1990), Cohen et al., *Biochim. Biophys. Acta* 1063: 95 (1991), Alving et al. "Preparation and Use of Liposomes in Immunological Studies," in *Liposome Technology, 2nd Edition, Vol. III*, Gregoriadis (Ed.), page 317 (CRC Press 1993), and Ansell et al., "Antibody Conjugation Methods for Active Targeting of Liposomes," in *Drug Targeting: Strategies, Principles, and Applications*, Francis and Delgado (Eds.), pages 51-68 (Humana Press, Inc. 2000)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (Eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified antibody components, in which an antibody component is linked with a polymer. Typically, the polymer is water soluble so that an antibody component does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-($C_1$-$C_{10}$) alkoxy, or aryloxy derivatives thereof (see, for example, Harris, et al., U.S. Pat. No. 5,252,714). The polymer may be branched or unbranched. Moreover, a mixture of polymers can be used to produce conjugates with antibody components.

Suitable water-soluble polymers include polyethylene glycol (PEG), monomethoxy-PEG, mono-($C_1$-$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A conjugate can also comprise a mixture of such water-soluble polymers.

As an illustration, a polyalkyl oxide moiety can be attached to the N-terminus of antibody component. PEG is one suitable polyalkyl oxide. As an illustration, an antibody component can be modified with PEG, a process known as "PEGylation." PEGylation of an antibody component can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, antibody component conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with an antibody component. An example of an activated PEG ester is PEG esterified to N-hydroxysuccinimide. As used herein, the term "acylation" includes the following types of linkages between an antibody component and a water soluble polymer: amide, carbamate, urethane, and the like. Methods for preparing PEGylated anti-zcytor19 antibody components by acylation will typically comprise the steps of (a) reacting an antibody component with PEG (such as a reactive ester of an aldehyde derivative of PEG) under conditions whereby one or more PEG groups attach to the antibody component, and (b) obtaining the reaction product(s). Generally, the optimal reaction conditions for acylation reactions will be determined based upon known parameters and desired results. For example, the larger the ratio of PEG:antibody component, the greater the percentage of polyPEGylated antibody component product.

The product of PEGylation by acylation is typically a polyPEGylated antibody component product, wherein the lysine $\epsilon$-amino groups are PEGylated via an acyl linking group. An example of a connecting linkage is an amide. Typically, the resulting antibody component will be at least 95% mono-, di-, or tri-pegylated, although some species with higher degrees of PEGylation may be formed depending upon the reaction conditions. PEGylated species can be separated from unconjugated antibody component using standard purification methods, such as dialysis, ultrafiltration, ion exchange chromatography, affinity chromatography, and the like.

PEGylation by alkylation generally involves reacting a terminal aldehyde derivative of PEG with antibody component in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the $\epsilon$-amino groups of the lysine residues and the $\alpha$-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups.

Reductive alkylation to produce a substantially homogenous population of monopolymer antibody component conjugate molecule can comprise the steps of: (a) reacting an antibody component with a reactive PEG under reductive alkylation conditions at a pH suitable to permit selective modification of the $\alpha$-amino group at the amino terminus of the antibody component, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopolymer antibody component conjugates, the reductive alkylation reaction conditions are those which permit the selective attachment of the water soluble polymer moiety to the N-terminus of the antibody component. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:antibody component need not be as large because more reactive groups are available. Typically, the pH will fall within the range of 3 to 9, or 3 to 6.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther.* 59:636 (1996), Monkarsh et al., *Anal. Biochem.* 247:434 (1997)).

Polypeptide cytotoxins can also be conjugated with a soluble polymer using the above methods either before or after conjugation to an antibody component. Soluble polymers can also be conjugated with antibody fusion proteins.

Naked anti-zcytor19 antibodies, or antibody fragments, can be supplemented with immunoconjugate or antibody fusion protein administration. In one variation, naked anti-zcytor19 antibodies (or naked antibody fragments) are administered with low-dose radiolabeled anti-zcytor19 antibodies or antibody fragments. As a second alternative, naked anti-zcytor19 antibodies (or antibody fragments) are administered with low-dose radiolabeled anti-zcytor19 antibodies-cytokine immunoconjugates. As a third alternative, naked anti-zcytor19 antibodies (or antibody fragments) are administered with anti-zcytor19-cytokine immunoconjugates that are not radiolabeled. With regard to "low doses" of $^{131}$I-labeled immunoconjugates, a preferable dosage is in the range of 15 to 40 mCi, while the most preferable range is 20 to 30 mCi. In contrast, a preferred dosage of $^{90}$Y-labeled immunoconjugates is in the range from 10 to 30 mCi, while the most preferable range is 10 to 20 mCi. Similarly, bispecific antibody components can be supplemented with immunoconjugate or antibody fusion protein administration.

Immunoconjugates having a boron addend-loaded carrier for thermal neutron activation therapy will normally be effected in similar ways. However, it will be advantageous to wait until non-targeted immunoconjugate clears before neutron irradiation is performed. Clearance can be accelerated using an antibody that binds to the immunoconjugate. See U.S. Pat. No. 4,624,846 for a description of this general principle.

The present invention also contemplates a method of treatment in which immunomodulators are administered to prevent, mitigate or reverse radiation-induced or drug-induced toxicity of normal cells, and especially hematopoietic cells. Adjunct immunomodulator therapy allows the administration of higher doses of cytotoxic agents due to increased tolerance of the recipient mammal. Moreover, adjunct immunomodulator therapy can prevent, palliate, or reverse dose-limiting marrow toxicity. Examples of suitable immunomodulators for adjunct therapy include granulocyte-colony stimulating factor, granulocyte macrophage-colony stimulating factor, thrombopoietin, IL-1, IL-3, IL-12, and the like. The method of adjunct immunomodulator therapy is disclosed by Goldenberg, U.S. Pat. No. 5,120,525.

The efficacy of anti-zcytor19 antibody therapy can be enhanced by supplementing naked antibody components with immunoconjugates and other forms of supplemental therapy described herein. In such multimodal regimens, the supplemental therapeutic compositions can be administered before, concurrently or after administration of naked anti-zcytor19 antibodies. Multimodal therapies of the present invention further include immunotherapy with naked anti-zcytor19 antibody components supplemented with administration of anti-zcytor19 immunoconjugates. In another form of multimodal therapy, subjects receive naked anti-zcytor19 antibodies and standard cancer chemotherapy.

The efficacy of an antibody component as a vaccine can be enhanced by conjugating the antibody component to a soluble immunogenic carrier protein. Suitable carrier proteins include tetanus toxin/toxoid, NTHi high molecular weight protein, diphtheria toxin/toxoid, detoxified *P. aeruginosa* toxin A, cholera toxin/toxoid, pertussis toxin/toxoid, *Clostridium perfringens* exotoxins/toxoid, hepatitis B surface antigen, hepatitis B core antigen, rotavirus VP 7 protein, respiratory syncytial virus F and G protein, and the like. Methods of preparing conjugated vaccines are known to those of skill in the art. See, for example, Cruse and Lewis (Eds.), *Conjugate Vaccines* (S. Karger Publishing 1989), and O'Hagan (Ed.), *Vaccine Adjuvants* (Humana Press, Inc. 2000). A vaccination composition can also include an adjuvant. Examples of suitable adjuvants include aluminum hydroxide and lipid. Methods of formulating vaccine compositions are well-known to those of ordinary skill in the art. See, for example, Rola, "Immunizing Agents and Diagnostic Skin Antigens," in *Remington: The Science and Practice of Pharmacy,* 19th Edition, Gennaro (Ed.), pages 1417-1433 (Mack Publishing Company 1995).

Pharmaceutical compositions may be supplied as a kit comprising a container that comprises anti-zcytor19 antibody components, or bispecific antibody components. Therapeutic molecules can be provided in the form of an injectable solution for single or multiple doses, or as a sterile powder that will be reconstituted before injection. Alternatively, such a kit can include a dry-powder disperser, liquid aerosol generator, or nebulizer for administration of an anti-zcytor19 antibody component. Such a kit may further comprise written information on indications and usage of the pharmaceutical composition. Moreover, such information may include a statement that the composition is contraindicated in patients with known hypersensitivity to exogenous antibodies.

Zcytor19 polypeptides, such as soluble zcytor19 receptors, may also be used within diagnostic systems for the detection of circulating levels of ligand. Within a related embodiment, antibodies or other agents that specifically bind to zcytor19 receptor polypeptides can be used to detect circulating receptor polypeptides. Elevated or depressed levels of ligand or receptor polypeptides may be indicative of pathological conditions, including cancer. Soluble receptor polypeptides may contribute to pathologic processes and can be an indirect marker of an underlying disease. For example, elevated levels of soluble IL-2 receptor in human serum have been associated with a wide variety of inflammatory and neoplastic conditions, such as myocardial infarction, asthma, myasthenia gravis, rheumatoid arthritis, acute T-cell leukemia, B-cell lymphomas, chronic lymphocytic leukemia, colon cancer, breast cancer, and ovarian cancer (Heaney et al., *Blood* 87:847-857, 1996). Similarly, as zcytor19 is expressed in B-cell leukemia cells, an increase of zcytor19 expression can even serve as a marker of an underlying disease, such as leukemia.

A ligand-binding polypeptide of a zcytor19 receptor, or "soluble receptor," can be prepared by expressing a truncated DNA encoding the zcytor19 extracellular cytokine-binding domain (residues 21 (Arg) to 226 (Asn) of SEQ ID NO:2 or SEQ ID NO:19), cytokine-binding fragment (e.g., residues 21 (Arg) to 223 (Pro) of SEQ ID NO:2 or SEQ ID NO:19; SEQ ID NO:4), the soluble version of zcytor19 variant, or the corresponding region of a non-human receptor. It is preferred that the extracellular domain be prepared in a form substantially free of transmembrane and intracellular polypeptide segments. Moreover, ligand-binding polypeptide fragments within the zcytor19 cytokine-binding domain, described above, can also serve as zcytor19 soluble receptors for uses described herein. To direct the export of a receptor polypeptide from the host cell, the receptor DNA is linked to a second DNA segment encoding a secretory peptide, such as a t-PA secretory peptide or a zcytor19 secretory peptide. To facilitate purification of the secreted receptor polypeptide, a C-terminal extension, such as a poly-histidine tag, Glu-Glu tag peptide, substance P, Flag™ peptide (Hopp et al., *Bio/Technology* 6:1204-1210, 1988; available from Eastman Kodak Co., New Haven, Conn.) or another polypeptide or protein for which an antibody or other specific binding agent is available, can be fused to the receptor polypeptide.

In an alternative approach, a receptor extracellular domain can be expressed as a fusion with immunoglobulin heavy chain constant regions, typically an $F_c$ fragment, which contains two constant region domains and lacks the variable region. Such fusions are typically secreted as multimeric molecules wherein the Fc portions are disulfide bonded to each other and two receptor polypeptides are arrayed in close proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a zcytor19-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. Collected fractions can be re-fractionated until the desired level of purity is reached.

Moreover, zcytor19 soluble receptors can be used as a "ligand sink," i.e., antagonist, to bind ligand in vivo or in vitro in therapeutic or other applications where the presence of the ligand is not desired. For example, in cancers that are expressing large amount of bioactive zcytor19 ligand, zcytor19 soluble receptors can be used as a direct antagonist of the ligand in vivo, and may aid in reducing progression and symptoms associated with the disease. Moreover, zcytor19 soluble receptor can be used to slow the progression of cancers that over-express zcytor19 receptors, by binding ligand in vivo that would otherwise enhance proliferation of those cancers. Similar in vitro applications for a zcytor19 soluble receptor can be used, for instance, as a negative selection to select cell lines that grow in the absence of zcytor19 ligand.

Moreover, zcytor19 soluble receptor can be used in vivo or in diagnostic applications to detect zcytor19 ligand-expressing cancers in vivo or in tissue samples. For example, the zcytor19 soluble receptor can be conjugated to a radio-label or fluorescent label as described herein, and used to detect the presence of the ligand in a tissue sample using an in vitro ligand-receptor type binding assay, or fluorescent imaging assay. Moreover, a radiolabeled zcytor19 soluble receptor could be administered in vivo to detect ligand-expressing solid tumors through a radio-imaging method known in the art. Similarly, zcytor19 polynucleotides, polypeptides, anti-zcytor19 andibodies, or peptide binding fragments can be used to detect zcytor19 receptor expressing cancers. In a preferred embodiment zcytor19 polynucleotides, polypeptides, anti-zcytor19 andibodies, or peptide binding fragments can be used to detect leukemias, more preferably B-cell leukemias, and most preferably pre-B-cell acute lymphoblastic leukemia.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population. Myocytes, osteoblasts, adipocytes, chrondrocytes, fibroblasts and reticular cells are believed to originate from a common mesenchymal stem cell (Owen et al., *Ciba Fdn. Symp.* 136:42-46, 1988). Markers for mesenchymal stem cells have not been well identified (Owen et al., *J. of Cell Sci.* 87:731-738, 1987), so identification is usually made at the progenitor and mature cell stages. The novel polypeptides of the present invention may be useful for studies to isolate mesenchymal stem cells and myocyte or other progenitor cells, both in vivo and ex vivo.

There is evidence to suggest that factors that stimulate specific cell types down a pathway towards terminal differentiation or dedifferentiation affect the entire cell population originating from a common precursor or stem cell. Thus, the present invention includes stimulating or inhibiting the proliferation of lymphoid cells, hematopoietic cells and endothelial cells. Thus molecules of the present invention, such as soluble zcytor19 receptors, cytokine-binding fragments, anti-zcytor19 antibodies, sense and antisense polynucleotides may have use in inhibiting tumor cells, and particularly lymphoid, hematopoietic, prostate, endothelial, and thyroid tumor cells.

Assays measuring differentiation include, for example, measuring cell markers associated with stage-specific expression of a tissue, enzymatic activity, functional activity or morphological changes (Watt, *FASEB,* 5:281-284, 1991; Francis, *Differentiation* 57:63-75, 1994; Raes, *Adv. Anim. Cell Biol. Technol. Bioprocesses,* 161-171, 1989; all incorporated herein by reference). Alternatively, zcytor19 polypeptide itself can serve as an additional cell-surface or secreted marker associated with stage-specific expression of a tissue. As such, direct measurement of zcytor19 polypeptide, or its loss of expression in a tissue as it differentiates, can serve as a marker for differentiation of tissues. Moreover, since zcytor19 is specifically-expressed in pre-B cell acute lymphoblastic leukemia cells, as well as several other cancers as described herein. As such, one of skill in the art would recognize that the polynucleotides, polypeptides and antibodies of the present invention can be used as a marker for these cancers.

Similarly, direct measurement of zcytor19 polypeptide, or its loss of expression in a tissue can be determined in a tissue or cells as they undergo tumor progression. Increases in invasiveness and motility of cells, or the gain or loss of expression of zcytor19 in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to zcytor19 expression. For example, appearance or disappearance of polypeptides that regulate cell motility can be used to aid diagnosis and prognosis of prostate cancer (Banyard, J. and Zetter, B. R., *Cancer and Metast. Rev.* 17:449-458, 1999). As an effector of cell motility, or as a B-cell tumor-specific marker, zcytor19 gain or loss of expression may serve as a diagnostic for lymphoid, B-cell, endothelial, hematopoietic and other cancers. Moreover, analogous to the prostate specific antigen (PSA), as a naturally-expressed tissue-specific marker, increased levels of zcytor19 polypeptides, or anti-zcytor19 antibodies in a patient, relative to a normal control can be indicative of disease in normal tissues where zcytor19 is expressed (See, e.g., Mulders, T M T, et al., *Eur. J. Surgical Oncol.* 16:37-41, 1990). Moreover, where zcytor19 expression appears to be restricted to specific normal human tissues, lack of zcytor19 expression in those tissues or strong zcytor19 expression in non-specific tissues would serve as a diagnostic of an abnormality in the cell or tissue type, of invasion or metastasis of cancerous tissues into non-cancerous tissue, and could aid a physician in directing further testing or investigation, or aid in directing therapy. As zcytor19 is expressed in esophagus, liver, ovary, rectum, stomach, and uterus tumors, and melanoma, diagnostic probes have particular use in diagnosing and identifying tissues from these cancers.

In addition, as zcytor19 is tissue-specific, polynucleotide probes, anti-zcytor19 antibodies, and detection the presence of zcytor19 polypeptides in tissue can be used to assess whether a specific tissue is present, for example, after surgery involving the excision of a diseased or cancerous tissues in which zcytor19 is expressed. As such, the polynucleotides, polypeptides, and antibodies of the present invention can be used as an aid to determine whether all tissue is excised after surgery, for example, after surgery for cancer. In such instances, it is especially important to remove all potentially diseased tissue to maximize recovery from the cancer, and to minimize recurrence. Preferred embodiments include fluorescent, radiolabeled, or calorimetrically labeled anti-zcytor19 antibodies and zcytor19 polypeptide binding partners, that can be used histologically or in situ. Specific tissues in which zcytor19 is expressed are disclosed herein.

Moreover, the activity and effect of zcytor19 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315-328, 1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing zcytor19, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 $mm^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., zcytor19, on the ability of the tumor to recruit vasculature and undergo metastasis can thus be assessed. In addition, aside from using adenovirus, the implanted cells can be transiently transfected with zcytor19. Use of stable zcytor19 transfectants as well as use of inducible promoters to activate zcytor19 expression in vivo are known in the art and can be used in this system to assess zcytor19 induction of metastasis. Moreover, purified zcytor19 or zcytor19 conditioned media can be directly injected in to this mouse model, and hence be used in this system. For general reference see, O'Reilly M S, et al. *Cell* 79:315-328, 1994; and Rusciano D, et al. Murine Models of Liver Metastasis. *Invasion Metastasis* 14:349-361, 1995.

The activity of zcytor19 and its derivatives (conjugates) on growth and dissemination of tumor cells derived from human hematologic malignancies can also be measured in vivo in a mouse Xenograft model. Several mouse models have been developed in which human tumor cells are implanted into immunodeficient mice, collectively referred to as xenograft models. See Cattan, A R and Douglas, E *Leuk. Res.* 18:513-22, 1994; and Flavell, D J, *Hematological Oncology* 14:67-82, 1996. The characteristics of the disease model vary with the type and quantity of cells delivered to the mouse. Typically, the tumor cells will proliferate rapidly and can be found circulating in the blood and populating numerous organ systems. Therapeutic strategies appropriate for testing in such a model include antibody induced toxicity, ligand-toxin conjugates or cell-based therapies. The latter method, commonly referred to adoptive immunotherapy, involves treatment of the animal with components of the human immune system (i.e. lymphocytes, NK cells) and may include ex vivo incubation of cells with zcytor19 or other immunomodulatory agents.

The mRNA corresponding to this novel DNA shows expression in lymphoid tissues, including pre-B cell acute lymphoblastic leukemia, bone marrow, and may be expressed in spleen, lymph nodes, and peripheral blood leukocytes. These data indicate a role for the zcytor19 receptor in leukemia, including B-cell leukemia, proliferation, differentiation, and/or activation of immune cells, and suggest a role in development and regulation of immune responses. The data also suggest that the interaction of zcytor19 with its ligand may stimulate proliferation and development of myeloid cells and may, like cytoikine receptors IL-2, IL-6, LIF, IL-11 and OSM (Baumann et al., *J. Biol. Chem.* 268:8414-8417, 1993), induce acute-phase protein synthesis in hepatocytes.

It is preferred to purify the polypeptides of the present invention to >80% purity, more preferably to >90% purity, even more preferably >95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zcytor19 polypeptides (or zcytor19 chimeric or fusion polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their biochemical, structural, and biological properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol*., Vol. 182, "Guide to Protein Purification", M. Deutscher, (ed.), Acad. Press, San Diego, 1990, pp. 529-39). Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid zcytor19 proteins, are constructed using regions or domains of the inventive zcytor19 in combination with those of other human cytokine receptor family proteins, or heterologous proteins (Sambrook et al., ibid., Altschul et al., ibid., Picard, *Cur. Opin. Biology,* 5:511-5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion polypeptides or proteins can be prepared by methods known to those skilled in the art by preparing each component of the fusion protein and chemically conjugating them. Alternatively, a polynucleotide encoding one or more components of the fusion protein in the proper reading frame can be generated using known techniques and expressed by the methods described herein. For example, part or all of a domain(s) conferring a biological function may be swapped between zcytor19 of the present invention with the functionally equivalent domain(s) from another cytokine family member. Such domains include, but are not limited to, the secretory signal sequence, extracellular cytokine binding domain, cytokine binding fragment, fibronectin type III domains, transmembrane domain, and intracellular signaling domain, as disclosed herein. Such fusion proteins would be expected to have a biological functional profile that is the same or similar to polypeptides of the present invention or other known family proteins, depending on the fusion constructed. Moreover, such fusion proteins may exhibit other properties as disclosed herein.

Standard molecular biological and cloning techniques can be used to swap the equivalent domains between the zcytor19 polypeptide and those polypeptides to which they are fused. Generally, a DNA segment that encodes a domain of interest, e.g., a zcytor19 domain described herein, is operably linked in frame to at least one other DNA segment encoding an additional polypeptide (for instance a domain or region from another cytokine receptor, such as, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511), or other class II cytokine receptor), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a cytokine binding domain, followed by a transmembrane domain, followed by an intracellular signaling domain. Such fusion proteins can be expressed, isolated, and assayed for activity as described herein. Moreover, such fusion proteins can be used to express and secrete fragments of the zcytor19 polypeptide, to be used, for example to inoculate an animal to generate anti-zcytor19 antibodies as described herein. For example a secretory signal sequence can be operably linked to extracellular cytokine binding domain, cytokine binding fragment, individual fibronectin type III domains, transmembrane domain, and intracellular signaling domain, as disclosed herein, or a combination thereof (e.g., operably linked polypeptides comprising a fibronectin III domain attached to a linker, or zcytor19 polypeptide fragments described herein), to secrete a fragment of zcytor19 polypeptide that can be purified as described herein and serve as an antigen to be inoculated into an animal to produce anti-zcytor19 antibodies, as described herein.

Zcytor19 polypeptides or fragments thereof may also be prepared through chemical synthesis. Zcytor19 polypeptides may be monomers or multimers; glycosylated or non-glycosylated; pegylated or non-pegylated; and may or may not include an initial methionine amino acid residue.

Polypeptides of the present invention can also be synthesized by exclusive solid phase synthesis, partial solid phase methods, fragment condensation or classical solution synthesis. Methods for synthesizing polypeptides are well known in the art. See, for example, Merrifield, *J. Am. Chem. Soc.* 85:2149, 1963; Kaiser et al., *Anal. Biochem.* 34:595, 1970. After the entire synthesis of the desired peptide on a solid support, the peptide-resin is with a reagent which cleaves the polypeptide from the resin and removes most of the side-chain protecting groups. Such methods are well established in the art.

The activity of molecules of the present invention can be measured using a variety of assays that measure cell differentiation and proliferation. Such assays are well known in the art and described herein.

Proteins of the present invention are useful for example, in treating lymphoid, immune, inflammatory, spleenic, blood or bone disorders, and can be measured in vitro using cultured cells or in vivo by administering molecules of the present invention to the appropriate animal model. For instance, host cells expressing a zcytor19 soluble receptor polypeptide can be embedded in an alginate environment and injected (implanted) into recipient animals. Alginate-poly-L-lysine microencapsulation, permselective membrane encapsulation and diffusion chambers are a means to entrap transfected mammalian cells or primary mammalian cells. These types of non-immunogenic "encapsulations" permit the diffusion of proteins and other macromolecules secreted or released by the captured cells to the recipient animal. Most importantly, the capsules mask and shield the foreign, embedded cells from the recipient animal's immune response. Such encapsulations can extend the life of the injected cells from a few hours or days (naked cells) to several weeks (embedded cells). Alginate threads provide a simple and quick means for generating embedded cells.

The materials needed to generate the alginate threads are known in the art. In an exemplary procedure, 3% alginate is prepared in sterile $H_2O$, and sterile filtered. Just prior to preparation of alginate threads, the alginate solution is again filtered. An approximately 50% cell suspension (containing about $5\times10^5$ to about $5\times10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle). A large bore needle is then attached to the syringe, and the thread is intraperitoneally injected into a recipient in a minimal volume of the Lactated Ringer's Solution.

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161-89, 1994; and J. T. Douglas and D. T. Curiel, *Science & Medicine* 4:44-53, 1997). The adenovirus system offers several advantages: (i) adenovirus can accommodate relatively large DNA inserts; (ii) can be grown to high-titer; (iii) infect a broad range of mammalian cell types; and (iv) can be used with a large number of different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022-2032, 1998; Raper, S. E. et al., *Human Gene Therapy* 9:671-679, 1998). In addition, deletion of E2b is reported to reduce immune responses (Amalfitano, A. et al., *J. Virol.* 72:926-933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615-623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

In view of the tissue distribution observed for zcytor19, agonists (including the natural ligand/substrate/cofactor/etc.) and antagonists have enormous potential in both in vitro and in vivo applications. Compounds identified as zcytor19 agonists are useful for stimulating growth of immune and hematopoietic cells in vitro and in vivo. For example, zcytor19 soluble receptors, and agonist compounds are useful as components of defined cell culture media, and may be used alone or in combination with other cytokines and hormones to replace serum that is commonly used in cell culture. Agonists are thus useful in specifically promoting the growth and/or development of T-cells, B-cells, and other cells of the lymphoid and myeloid lineages in culture. Moreover, zcytor19 soluble receptor, agonist, or antagonist may be used in vitro in an assay to measure stimulation of colony formation from isolated primary bone marrow cultures. Such assays are well known in the art.

Antagonists are also useful as research reagents for characterizing sites of ligand-receptor interaction. Inhibitors of zcytor19 activity (zcytor19 antagonists) include anti-zcytor19 antibodies and soluble zcytor19 receptors, as well as other peptidic and non-peptidic agents (including ribozymes).

Zcytor19 can also be used to identify modulators (e.g, antagonists) of its activity. Test compounds are added to the assays disclosed herein to identify compounds that inhibit the activity of zcytor19. In addition to those assays disclosed herein, samples can be tested for inhibition of zcytor19 activity within a variety of assays designed to measure zcytor19 binding, oligomerization, or the stimulation/inhibition of zcytor19-dependent cellular responses. For example, zcytor19-expressing cell lines can be transfected with a reporter gene construct that is responsive to a zcytor19-stimulated cellular pathway. Reporter gene constructs of this type are known in the art, and will generally comprise a zcytor19-DNA response element operably linked to a gene encoding an assay detectable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273-7, 1990) and serum response elements (SRE) (Shaw et al. *Cell* 56: 563-72, 1989). Cyclic AMP response elements are reviewed in Roestler et al., *J. Biol. Chem.* 263 (19):9063-6; 1988 and Habener, *Molec. Endocrinol.* 4 (8):1087-94; 1990. Hormone response elements are reviewed in Beato, *Cell* 56:335-44; 1989. Candidate compounds, solutions, mixtures or extracts or conditioned media from various cell types are tested for the ability to enhance the activity of zcytor19 receptor as evidenced by a increase in zcytor19 stimulation of reporter gene expression. Assays of this type will detect compounds that directly stimulate zcytor19 signal transduction activity through binding the receptor or by otherwise stimulating part of the signal cascade. As such, there is provided a method of identifying agonists of zcytor19 polypeptide, comprising providing cells responsive to a zcytor19 polypeptide, culturing a first portion of the cells in the absence of a test compound, culturing a second portion of the cells in the presence of a test compound, and detecting a increase in a cellular response of the second portion of the cells as compared to the first portion of the cells. Moreover a third cell, containing the reporter gene construct described above, but not expressing zcytor19 receptor, can be used as a control cell to assess non-specific, or non-zcytor19-mediated, stimulation of the reporter. Agonists, including the natural ligand, are therefore useful to stimulate or increase zcytor19 polypeptide function.

A zcytor19 ligand-binding polypeptide, such as the extracellular domain or cytokine binding domain disclosed herein, can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HC1), or pH to disrupt ligand-receptor binding.

An assay system that uses a ligand-binding receptor (or an antibody, one member of a complement/anti-complement pair) or a binding fragment thereof, and a commercially available biosensor instrument may be advantageously employed (e.g., BIAcore™, Pharmacia Biosensor, Piscataway, N.J.; or SELDI™ technology, Ciphergen, Inc., Palo Alto, Calif.). Such receptor, antibody, member of a complement/anti-complement pair or fragment is immobilized onto the surface of a receptor chip. Use of this instrument is disclosed by Karlsson, *J. Immunol. Methods* 145:229-240, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660-672, 1949) and calorimetric assays (Cunningham et al., *Science* 253:545-48, 1991; Cunningham et al., *Science* 245:821-25, 1991).

Zcytor19 polypeptides can also be used to prepare antibodies that bind to zcytor19 epitopes, peptides or polypeptides. The zcytor19 polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a zcytor19 polypeptide (e.g., SEQ ID NO:2, SEQ ID NO:19 or SEQ ID NO:21). Polypeptides comprising a larger portion of a zcytor19 polypeptide, i.e., from 30 to 100 residues up to the entire length of the amino acid sequence are included. Antigens or immunogenic epitopes can also include attached tags, adjuvants and carriers, as described herein. Suitable antigens include the zcytor19 polypeptide encoded by SEQ ID NO:2 from amino acid number 21 (Arg) to amino acid number 491 (Arg), or a contiguous 9 to 471 amino acid fragment thereof. Suitable antigens also include the zcytor19 polypeptide encoded by SEQ ID NO:19 from amino acid number 21 (Arg) to amino acid number 520 (Arg), or a contiguous 9 to 500 amino acid fragment thereof; and the truncated soluble zcytor19 polypeptide encoded by SEQ ID NO:21 from amino acid number 21 (Arg) to amino acid number 211 (Ser), or a contiguous 9 to 191 amino acid fragment thereof. Preferred peptides to use as antigens are the extracellular cytokine binding domain, cytokine binding fragment, fibronectin type III domains, intracellular signaling domain, or other domains and motifs disclosed herein, or a combination thereof; and zcytor19 hydrophilic peptides such as those predicted by one of skill in the art from a hydrophobicity plot, determined for example, from a Hopp/Woods hydrophilicity profile based on a sliding six-residue window, with buried G, S, and T residues and exposed H, Y, and W residues ignored. Zcytor19 hydrophilic peptides include peptides comprising amino acid sequences selected from the group consisting of: (1) residues 295 through 300 of SEQ ID NO:2; (2) residues 451 through 456 of SEQ ID NO:2; (3) residues 301 through 306 of SEQ ID NO:2; (4) residues 294 through 299 of SEQ ID NO:2; and (5) residues 65 through 70 of SEQ ID NO:2. In addition, zcytor19 antigenic epitopes as predicted by a Jameson-Wolf plot, e.g., using DNASTAR Protean program (DNASTAR, Inc., Madison, Wis.) are suitable antigens. In addition, conserved motifs, and variable regions between conserved motifs of zcytor19 are suitable antigens. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zcytor19 polypeptide or a fragment thereof. The immunogenicity of a zcytor19 polypeptide may be increased through the use of an adjuvant, such as alum (aluminum hydroxide) or Freund's complete or incomplete adjuvant. Polypeptides useful for immunization also include fusion polypeptides, such as fusions of zcytor19 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Alternative techniques for generating or selecting antibodies useful herein include in vitro exposure of lymphocytes to zcytor19 protein or peptide, and selection of antibody display libraries in phage or similar vectors (for instance, through use of immobilized or labeled zcytor19 protein or peptide). Genes encoding polypeptides having potential zcytor19 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zcytor19 sequences disclosed herein to identify proteins which bind to zcytor19. These "binding peptides" which interact with zcytor19 polypeptides can be used for tagging cells, e.g., such as those in which zcytor19 is specifically expressed; for isolating homolog polypeptides by affinity purification; they can be directly or indirectly conjugated to drugs, toxins, radionuclides and the like. These binding peptides can also be used in analytical methods such as for screening expression libraries and neutralizing activity. The binding peptides can also be used for diagnostic assays for determining circulating levels of zcytor19 polypeptides; for detecting or quantitating soluble zcytor19 polypeptides as marker of underlying pathology or disease. These binding peptides can also act as zcytor19 "antagonists" to block zcytor19 binding and signal transduction in vitro and in vivo. These anti-zcytor19 binding peptides would be useful for inhibiting the action of a ligand that binds with zcytor19.

Antibodies are considered to be specifically binding if: 1) they exhibit a threshold level of binding activity, and 2) they do not significantly cross-react with related polypeptide molecules. A threshold level of binding is determined if anti-zcytor19 antibodies herein bind to a zcytor19 polypeptide, peptide or epitope with an affinity at least 10-fold greater than the binding affinity to control (non-zcytor19) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

Whether anti-zcytor19 antibodies do not significantly cross-react with related polypeptide molecules is shown, for example, by the antibody detecting zcytor19 polypeptide but not known related polypeptides using a standard Western blot analysis (Ausubel et al., ibid.). Examples of known related polypeptides are those disclosed in the prior art, such as known orthologs, and paralogs, and similar known members of a protein family (e.g., class II cytokine receptors, for example, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511) receptors). Screening can also be done using non-human zcytor19, and zcytor19 mutant polypeptides. Moreover, using routine methods, antibodies can be "screened against" known related polypeptides, to isolate a population that specifically binds to the zcytor19 polypeptides. For example, antibodies raised to zcytor19 are adsorbed to related polypeptides adhered to insoluble matrix; antibodies specific to zcytor19 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies: Principles and Practice, Goding*, J. W. (eds.), Academic Press Ltd., 1996; Benjamin et al., *Ann. Rev. Immunol.* 2: 67-101, 1984. Specifically binding anti-zcytor19 antibodies can be detected by a number of methods in the art, and disclosed below.

A variety of assays known to those skilled in the art can be utilized to detect antibodies which specifically bind to zcytor19 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zcytor19 protein or polypeptide.

Antibodies to zcytor19 may be used for tagging cells that express zcytor19; for isolating zcytor19 by affinity purification; for diagnostic assays for determining circulating levels of zcytor19 polypeptides; for detecting or quantitating soluble zcytor19 as marker of underlying pathology or disease; for detecting or quantitating in a histologic, biopsy, or tissue sample zcytor19 receptor as marker of underlying pathology or disease; for stimulating cytotoxicity or ADCC on zcytor19-bearing cancer cells; in analytical methods employing FACS; for screening expression libraries; for generating anti-idiotypic antibodies; and as neutralizing antibodies or as antagonists to block zcytor19 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zcytor19 or fragments thereof may be used in vitro to detect denatured zcytor19 or fragments thereof in assays, for example, Western Blots or other assays known in the art.

Antibodies to zcytor19 are useful for tagging cells that express the receptor and assaying Zcytor19 expression levels, for affinity purification, within diagnostic assays for determining circulating levels of soluble receptor polypeptides, analytical methods employing fluorescence-activated cell sorting. Divalent antibodies may be used as agonists to mimic the effect of a zcytor19 ligand.

Antibodies herein can also be directly or indirectly conjugated to drugs, toxins, radionuclides and the like, and these conjugates used for in vivo diagnostic or therapeutic applications. For instance, antibodies or binding polypeptides which recognize zcytor19 of the present invention can be used to identify or treat tissues or organs that express a corresponding anti-complementary molecule (i.e., a zcytor19 receptor). More specifically, anti-zcytor19 antibodies, or bioactive fragments or portions thereof, can be coupled to detectable or cytotoxic molecules and delivered to a mammal having cells, tissues or organs that express the zcytor19 molecule. A preferred use of such conjugated antibodies is to target the drug to cancers that express the zcytor19 receptor. For example, such antibodies can be used to target lymphoid, B-cell, and pre-B-cell acute lymphoblastic leukemia cancers, and esophagus, liver, ovary, rectum, stomach, and uterus tumors, and melanoma, Suitable detectable molecules may be directly or indirectly attached to polypeptides that bind zcytor19 ("binding polypeptides," including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues, e.g., such as those specific tissues and tumors wherein zcytor19 is expressed). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

Similarly, in another embodiment, zcytor19 binding polypeptide-cytokine or antibody-cytokine fusion proteins can be used for enhancing in vivo killing of target tissues (for example, blood, lymphoid, colon, and bone marrow cancers, or other cancers described herein wherein zcytor19 is expressed), if the binding polypeptide-cytokine or anti-zcytor19 antibody targets the hyperproliferative cell (See, generally, Hornick et al., *Blood* 89:4437-47, 1997). They described fusion proteins enable targeting of a cytokine to a desired site of action, thereby providing an elevated local concentration of cytokine. Suitable anti-zcytor19 antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, zcytor19 binding polypeptide or antibody fusion proteins described herein can be used for enhancing in vivo killing of target tissues by directly stimulating a zcytor19-modulated apoptotic pathway, resulting in cell death of hyperproliferative cells expressing zcytor19.

The bioactive binding polypeptide or antibody conjugates described herein can be delivered orally, intravenously, intraarterially or intraductally, or may be introduced locally at the intended site of action.

Moreover, anti-zcytor19 antibodies and binding fragments can be used for tagging and sorting cells that specifically-express Zcytor19, such as bone marrow and thyroid cells, and other cells, described herein. Such methods of cell tagging and sorting are well known in the art (see, e.g., "Molecular Biology of the Cell", 3$^{rd}$ Ed., Albert, B. et al. (Garland Publishing, London & New York, 1994). One of skill in the art would recognize the importance of separating cell tissue types to study cells, and the use of antibodies to separate specific cell tissue types. Basically, antibodies that bind to the surface of a cell type are coupled to various matrices such as collagen, polysaccharide beads, or plastic to form an affinity surface to which only cells recognized by the antibodies will adhere. The bound cells are then recovered by conventional techniques. Other methods involve separating cells by flow cytometry, or using a fluorescence-activated cell sorter (FACS). In this technique one labels cells with antibodies that are coupled to a fluorescent dye. The labeled cells are then separated from unlabeled cells in a FACS machine. In FACS sorting individual cells traveling in single file pass through a laser beam and the fluorescence of each cell is measured. Slightly further down-stream, tiny droplets, most containing either one or no cells, are formed by a vibrating nozzle. The droplets containing a single cell are automatically give a positive or negative charge at the moment of formation, depending on whether the cell they contain is fluorescent, and then deflected by a strong electric field into an appropriate container. Such machines can select 1 cell in 1000 and sort about 5000 cells each second. This produces a uniform population of cells for cell culture.

One of skill in the art would recognize that the antibodies to the Zcytor19 polypeptides of the present invention are useful, because not all tissue types express the Zcytor19 receptor and because it is important that biologists be able to separate specific cell types for further study and/or therapeutic re-implantation into the body. This is particularly relevant in cells such as immune cells, wherein zcytor19 is expressed.

Four-helix bundle cytokines that bind to cytokine receptors as well as other proteins produced by activated lymphocytes play an important biological role in cell differentiation, activation, recruitment and homeostasis of cells throughout the body. Therapeutic utility includes treatment of diseases which require immune regulation including autoimmune diseases, such as, rheumatoid arthritis, multiple sclerosis, myasthenia gravis, systemic lupus erythomatosis and diabetes. Zcytor19 receptor antagonists or agonists, including zcytor19 soluble receptors, anti-receptor antibodies, and the natural ligand, may be important in the regulation of inflammation, and therefore would be useful in treating rheumatoid arthritis, asthma, ulcerative colitis, inflammatory bowel disease, Crohn's disease, and sepsis. There may be a role of zcytor19 antagonists or agonists, including soluble receptors, anti-receptor antibodies and the natural ligand, in mediating tumorgenesis, and therefore would be useful in the treatment of cancer. Zcytor19 antagonists or agonists, including soluble receptors anti-receptor antibodies and the natural ligand, may be a potential therapeutic in suppressing the immune system which would be important for reducing graft rejection or in prevention of graft vs. host disease.

Alternatively, zcytor19 antagonists or agonists, including soluble receptors, anti-zcytor19 receptor antibodies and the natural ligand may activate the immune system which would be important in boosting immunity to infectious diseases, treating immunocompromised patients, such as HIV+patient, or in improving vaccines. In particular, zcytor19 antagonists or agonists, including soluble receptors, anti-receptor antibodies, and the natural ligand can modulate, stimulate or expand NK cells, or their progenitors, and would provide therapeutic value in treatment of viral infection, and as an anti-neoplastic factor. NK cells are thought to play a major role in elimination of metastatic tumor cells and patients with both metastases and solid tumors have decreased levels of NK cell activity (Whiteside et. al., *Curr. Top. Microbiol. Immunol.* 230:221-244, 1998).

Polynucleotides encoding zcytor19 polypeptides are useful within gene therapy applications where it is desired to increase or inhibit zcytor19 activity. If a mammal has a mutated or absent zcytor19 gene, the zcytor19 gene can be introduced into the cells of the mammal. In one embodiment, a gene encoding a zcytor19 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-30, 1991); an attenuated adenovirus vector, such as the vector described by Stratford-Perricaudet et al., *J. Clin. Invest.* 90:626-30, 1992; and a defective adeno-associated virus vector (Samulski et al., *J. Virol.* 61:3096-101, 1987; Samulski et al., *J. Virol.* 63:3822-8, 1989).

In another embodiment, a zcytor19 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413-7, 1987; Mackey et al., *Proc. Natl. Acad. Sci. USA* 85:8027-31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7, 1992; Wu et al., *J. Biol. Chem.* 263:14621-4, 1988.

Antisense methodology can be used to inhibit zcytor19 gene transcription, such as to inhibit cell proliferation in vivo. Polynucleotides that are complementary to a segment of a zcytor19-encoding polynucleotide (e.g., a polynucleotide as set forth in SEQ ID NO:1 SEQ ID NO:18, or SEQ ID NO:20) are designed to bind to zcytor19-encoding mRNA and to inhibit translation of such mRNA. Such antisense polynucleotides are used to inhibit expression of zcytor19 polypeptide-encoding genes in cell culture or in a subject.

In addition, as a cell surface molecule, zcytor19 polypeptides can be used as a target to introduce gene therapy into a cell. This application would be particularly appropriate for introducing therapeutic genes into cells in which zcytor19 is normally expressed, such as lymphoid tissue, bone marrow, prostate, thyroid, and PBLs, or cancer cells which express zcytor19 polypeptide. For example, viral gene therapy, such as described above, can be targeted to specific cell types in which express a cellular receptor, such as zcytor19 polypeptide, rather than the viral receptor. Antibodies, or other molecules that recognize zcytor19 molecules on the target cell's surface can be used to direct the virus to infect and administer gene therapeutic material to that target cell. See, Woo, S. L. C, *Nature Biotech.* 14:1538, 1996; Wickham, T. J. et al, *Nature Biotech.* 14:1570-1573, 1996; Douglas, J. T et al., *Nature Biotech.* 14:1574-1578, 1996; Rihova, B., *Crit. Rev. Biotechnol.* 17:149-169, 1997; and Vile, R. G. et al., *Mol. Med. Today* 4:84-92, 1998. For example, a bispecific antibody containing a virus-neutralizing Fab fragment coupled to a zcytor19-specific antibody can be used to direct the virus to cells expressing the zcytor19 receptor and allow efficient entry of the virus containing a genetic element into the cells. See, for example, Wickham, T. J., et al., *J. Virol.* 71:7663-7669, 1997; and Wickham, T. J., et al., *J. Virol.* 70:6831-6838, 1996.

The present invention also provides reagents which will find use in diagnostic applications. For example, the zcytor19 gene, a probe comprising zcytor19 DNA or RNA or a subsequence thereof can be used to determine if the zcytor19 gene is present on chromosome 1 or if a mutation has occurred. Zcytor19 is located at the 1p36.11 region of chromosome 1. Detectable chromosomal aberrations at the zcytor19 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, fluorescence in situ hybridization methods, short tandem repeat (STR) analysis employing PCR techniques, and other genetic linkage analysis techniques known in the art (Sambrook et al., ibid.; Ausubel et. al., ibid.; Marian, *Chest* 108:255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The zcytor19 gene is located at the 1p36.11 region of chromosome 1. One of skill in the art would recognize that chromosomal aberrations in and around the 1p36 region are involved in several cancers including neuroblastoma, melanoma, breast, colon, prostate and other cancers. Such aberrations include gross chromosomal abnormalities such as translocations, loss of heterogeneity (LOH) and the like in and around 1p36. Thus, a marker in the 1p36.11 locus, such as provided by the polynucleotides of the present invention, would be useful in detecting translocations, aneuploidy, rearrangements, LOH other chromosomal abnormalities involving this chromosomal region that are present in cancers. For example, zcytor19 polynucleotide probes can be used to detect abnormalities or genotypes associated with neuroblastoma, wherein LOH between 1p36.1 and 1p36.3 is prevalent, and a breakpoint at 1p36.1 is evident. At least 70% of neuroblastomas have cytogenetically visible chromosomal aberrations in 1p, including translocation and deletion, and that the abnormality is most likely due to complex translocation and deletion mechanisms. See, for example Ritke, M K et al., *Cytogenet. Cell Genet.* 50:84-90, 1989; and Weith, A et al., *Genes Chromosomes Cancer* 1:159-166, 1989). As zcytor19 is localized to 1p36.11, and falls directly within the region wherein aberrations are prevalent in neuroblastoma, one of skill in the art would appreciate that the polynucleotides of the present invention could serve as a diagnostic for neuroblastoma, as well as aid in the elucidation of translocation and deletion mechanisms that give rise to neuroblastoma. In addition, LOH at 1p36 is evident in melanoma (Dracopoli, N C et al, *Am. J. Hum. Genet.* 45 (suppl.):A19, 1989; Dracopoli, N C et al, *Proc. Nat. Acad. Sci.* 86:4614-4618, 1989; Goldstein, A M et al., *Am. J. Hum. Genet.* 52:537-550, 1993); as well as prostate cancer in families with a history of both prostate and brain cancer (1p36, LOH) (Gibbs, M et al., *Am. J. Hum. Genet.* 64:776-787, 1999); and breast cancer, wherein deletions and duplications of chromosome 1 are the most common aberrations in breast carcinoma (1p36) (Kovacs, G. *Int. J. Cancer* 21:688-694, 1978; Rodgers, C et al., *Cancer Genet. Cytogent.* 13:95-119, 1984; and Genuardi, M et al., *Am. J. Hum. Genet.* 45:73-82, 1989). Since translocation, LOH and other aberrations in this region of human chromosome 1 are so prevalent in human cancers, and the zcytor19 gene is specifically localized to 1p36.11, the polynucleotides of the present invention have use in detecting such aberrations that are clearly associated with human disease, as described herein.

Moreover, there is further evidence for cancer resulting from mutations in the 1p36 region wherein zcytor19 is located, and polynucleotide probes can be used to detect abnormalities or genotypes associated therewith: P73, a potential tumor suppressor maps to 1p36 a region frequently deleted in neuroblastoma and other cancers (Kaghad, M et al., Cell 90:809-819, 1997); rhabdomyosarcoma, which involves a translocation at the 1p36.2-p36.12 region of chromosome 1 that results in a fusion of the PAX7 gene from chromosome 1 with FKHR gene on chromosome 13; Leukemia-associated Protein (LAP) (1p36.1-p35) is increased in the cells of various types of leukemia; heparin sulfate proteoglycan (Perlecan) (1p36.1) associated with tumors, and wherein translocations are seen; and colon cancer (1p36-p35). Further, zcytor19 polynucleotide probes can be used to detect abnormalities or genotypes associated with chromosome 1p36.11 deletions and translocations associated with human diseases, and preferably cancers, as described above. Moreover, amongst other genetic loci, those for C1q complement components (C1QA, B, and G) (1p36.3-p34.1); dyslexia (1p36-p34); lymphoid activation antigen CD30 (1p36); sodium channel non-voltage-gated type 1 (1p36.3-p36.2); tumor necrosis factor receptors (TNFRSF1b and TNFRS12) (1p36.3-p36.2) which like zcytor19 are cytokine receptors; phospholipase A2 (PLA2) (1p35); rigid spine muscular dystrophy (1p36-p35) all manifest themselves in human disease states as well as map to this region of the human genome. See the Online Mendellian Inheritance of Man (OMIM™, National Center for Biotechnology Information, National Library of Medicine. Bethesda, Md.) gene map, and references therein, for this region of human chromosome 1 on a publicly available world wide web server. All of these serve as possible candidate genes for an inheritable disease which show linkage to the same chromosomal region as the zcytor19 gene. Thus, zcytor19 polynucleotide probes can be used to detect abnormalities or genotypes associated with these defects.

Similarly, defects in the zcytor19 gene itself may result in a heritable human disease state. The zcytor19 gene (1p36.11) is located near another class II receptor, the zcytor11 cytokine receptor gene (1p35.1) (commonly owned U.S. Pat. No. 5,965,704), as well as TNF receptors (1p36.3-p36.2), suggesting that this chromosomal region is commonly regulated, and/or important for immune function. Moreover, one of skill in the art would appreciate that defects in cytokine receptors are known to cause disease states in humans. For example, growth hormone receptor mutation results in dwarfism (Amselem, S et al., *New Eng. J. Med.* 321: 989-995, 1989), IL-2 receptor gamma mutation results in severe combined immunodeficiency (SCID) (Noguchi, M et al., *Cell* 73: 147-157, 1993), c-Mp1 mutation results in thrombocytopenia (Ihara, K et al., *Proc. Nat. Acad. Sci.* 96: 3132-3136, 1999), and severe mycobacterial and *Salmonella* infections result in interleukin-12 receptor-deficient patients (de Jong, R et al., *Science* 280: 1435-1438, 1998), amongst others. Thus, similarly, defects in zcytor19 can cause a disease state or susceptibility to disease or infection. As, zcytor19 is a cytokine receptor in a chromosomal hot spot for aberrations involved in numerous cancers and is shown to be expressed in pre-B-cell acute leukemia cells, and other cancers described herein, the molecules of the present invention could also be directly involved in cancer formation or metastasis. As the zcytor19 gene is located at the 1p36.11 region zcytor19, polynucleotide probes can be used to detect chromosome 1p36.11 loss, trisomy, duplication or translocation associated with human diseases, such as immune cell cancers, neuroblastoma, bone marrow cancers, thyroid, parathyroid, prostate, melanoma, or other cancers, or immune diseases. Moreover, molecules of the present invention, such as the polypeptides, antagonists, agonists, polynucleotides and antibodies of the present invention would aid in the detection, diagnosis prevention, and treatment associated with a zcytor19 genetic defect.

A diagnostic could assist physicians in determining the type of disease and appropriate associated therapy, or assistance in genetic counseling. As such, the inventive anti-zcytor19 antibodies, polynucleotides, and polypeptides can be used for the detection of zcytor19 polypeptide, mRNA or anti-zcytor19 antibodies, thus serving as markers and be directly used for detecting or genetic diseases or cancers, as described herein, using methods known in the art and described herein. Further, zcytor19 polynucleotide probes can be used to detect abnormalities or genotypes associated with chromosome 1p36.11 deletions and translocations associated with human diseases, other translocations involved with malignant progression of tumors or other 1p36.11 mutations, which are expected to be involved in chromosome rearrangements in malignancy; or in other cancers, or in spontaneous abortion. Similarly, zcytor19 polynucleotide probes can be used to detect abnormalities or genotypes associated with chromosome 1p36.11 trisomy and chromosome loss associated with human diseases. Thus, zcytor19 polynucleotide probes can be used to detect abnormalities or genotypes associated with these defects.

As discussed above, defects in the zcytor19 gene itself may result in a heritable human disease state. Molecules of the present invention, such as the polypeptides, antagonists, agonists, polynucleotides and antibodies of the present invention would aid in the detection, diagnosis prevention, and treatment associated with a zcytor19 genetic defect. In addition, zcytor19 polynucleotide probes can be used to detect allelic differences between diseased or non-diseased individuals at the zcytor19 chromosomal locus. As such, the zcytor19 sequences can be used as diagnostics in forensic DNA profiling.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14-17 nt). PCR primers are at least 5 nt in length, preferably 15 or more, more preferably 20-30 nt. For gross analysis of genes, or chromosomal DNA, a zcytor19 polynucleotide probe may comprise an entire exon or more. Exons are readily determined by one of skill in the art by comparing zcytor19 sequences (SEQ ID NO:1 SEQ ID NO:18, or SEQ ID NO:20) with the human genomic DNA for zcytor19 (Genbank Accession No. AL358412). In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a zcytor19 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a zcytor19 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zcytor19 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1 SEQ ID NO:18, or SEQ ID NO:20 the complement of SEQ ID NO: 1, SEQ ID NO:18, or SEQ ID NO:20 or an RNA equivalent thereof. Such methods of showing genetic linkage analysis to human disease phenotypes are well known in the art. For reference to PCR based methods in diagnostics see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the zcytor19 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83-88 (Humana Press, Inc. 1998)). Direct analysis of an zcytor19 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Mice engineered to express the zcytor19 gene, referred to as "transgenic mice," and mice that exhibit a complete absence of zcytor19 gene function, referred to as "knockout mice," may also be generated (Snouwaert et al., *Science* 257: 1083, 1992; Lowell et al., *Nature* 366:740-42, 1993; Capecchi, M. R., Science 244: 1288-1292, 1989; Palmiter, R. D. et al. *Annu Rev Genet.* 20: 465-499, 1986). For example, transgenic mice that over-express zcytor19, either ubiquitously or under a tissue-specific or tissue-restricted promoter can be used to ask whether over-expression causes a phenotype. For example, over-expression of a wild-type zcytor19 polypeptide, polypeptide fragment or a mutant thereof may alter normal cellular processes, resulting in a phenotype that identifies a tissue in which zcytor19 expression is functionally relevant and may indicate a therapeutic target for the zcytor19, its agonists or antagonists. For example, a preferred transgenic mouse to engineer is one that expresses a "dominant-negative" phenotype, such as one that over-expresses the zcytor19 polypeptide comprising an extracellular cytokine binding domain with the transmembrane domain attached (approximately amino acids 21 (Arg) to 249 (Trp) of SEQ ID NO:2 or SEQ ID NO:19; or SEQ ID NO:4 attached in frame to a transmembrane domain). Another preferred transgenic mouse is one that over-expresses zcytor19 soluble receptors, such as those disclosed herein. Moreover, such over-expression may result in a phenotype that shows similarity with human diseases. Similarly, knockout zcytor19 mice can be used to determine where zcytor19 is absolutely required in vivo. The phenotype of knockout mice is predictive of the in vivo effects of a zcytor19 antagonist, such as those described herein, may have. The mouse or the human zcytor19 cDNA can be used to isolate murine zcytor19 mRNA, cDNA and genomic DNA, which are subsequently used to generate knockout mice. These transgenic and knockout mice may be employed to study the zcytor19 gene and the protein encoded thereby in an in vivo system, and can be used as in vivo models for corresponding human or animal diseases (such as those in commercially viable animal populations). The mouse models of the present invention are particularly relevant as tumor models for the study of cancer biology and progression. Such models are useful in the development and efficacy of therapeutic molecules used in human cancers. Because increases in zcytor19 expression, as well as decreases in zcytor19 expression are associated with specific human cancers, both transgenic mice and knockout mice would serve as useful animal models for cancer. Moreover, in a preferred embodiment, zcytor19 transgenic mouse can serve as an animal model for specific tumors, particularly esophagus, liver, ovary, rectum, stomach, and uterus tumors, and melanoma, B-cell leukemia and other lymphoid cancers. Moreover, transgenic mice expression of zcytor19 antisense polynucleotides or ribozymes directed against zcytor19, described herein, can be used analogously to transgenic mice described above.

For pharmaceutical use, the soluble receptor polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a zcytor19 soluble receptor polypeptide in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of zcytor19 soluble receptor polypeptide is an amount sufficient to produce a clinically significant effect.

Polynucleotides and polypeptides of the present invention will additionally find use as educational tools as a laboratory practicum kits for courses related to genetics and molecular biology, protein chemistry and antibody production and analysis. Due to its unique polynucleotide and polypeptide sequence molecules of zcytor19 can be used as standards or as "unknowns" for testing purposes. For example, zcytor19 polynucleotides can be used as an aid, such as, for example, to teach a student how to prepare expression constructs for bacterial, viral, and/or mammalian expression, including fusion constructs, wherein zcytor19 is the gene to be expressed; for determining the restriction endonuclease cleavage sites of the polynucleotides; determining mRNA and DNA localization of zcytor19 polynucleotides in tissues (i.e., by Northern and Southern blotting as well as polymerase chain reaction); and for identifying related polynucleotides and polypeptides by nucleic acid hybridization.

Zcytor19 polypeptides can be used educationally as an aid to teach preparation of antibodies; identifying proteins by Western blotting; protein purification; determining the weight of expressed zcytor19 polypeptides as a ratio to total protein expressed; identifying peptide cleavage sites; coupling amino and carboxyl terminal tags; amino acid sequence analysis, as well as, but not limited to monitoring biological activities of both the native and tagged protein (i.e., receptor binding, signal transduction, proliferation, and differentiation) in vitro and in vivo. Zcytor19 polypeptides can also be used to teach analytical skills such as mass spectrometry, circular dichroism to determine conformation, especially of the four alpha helices, x-ray crystallography to determine the three-dimensional structure in atomic detail, nuclear magnetic resonance spectroscopy to reveal the structure of proteins in solution. For example, a kit containing the zcytor19 can be given to the student to analyze. Since the amino acid sequence would be known by the professor, the specific protein can be given to the student as a test to determine the skills or develop the skills of the student, the teacher would then know whether or not the student has correctly analyzed the polypeptide. Since every polypeptide is unique, the educational utility of zcytor19 would be unique unto itself.

Moreover, since zcytor19 has a tissue-specific expression and is a polypeptide with a class II cytokine receptor structure and a distinct chromosomal localization, and expression pattern, activity can be measured using proliferation assays; luciferase and binding assays described herein. Moreover, expression of zcytor19 polynucleotides and polypeptides in lymphoid and other tissues can be analyzed in order to train students in the use of diagnostic and tissue-specific identification and methods. Moreover zcytor19 polynucleotides can be used to train students on the use of chromosomal detection and diagnostic methods, since it's locus is known. Moreover, students can be specifically trained and educated about human chromosome 1, and more specifically the locus 1p36.11 wherein the zcytor19 gene is localized. Such assays are well known in the art, and can be used in an educational setting to teach students about cytokine receptor proteins and examine different properties, such as cellular effects on cells, enzyme kinetics, varying antibody binding affinities, tissue specificity, and the like, between zcytor19 and other cytokine receptor polypeptides in the art.

The antibodies which bind specifically to zcytor19 can be used as a teaching aid to instruct students how to prepare affinity chromatography columns to purify zcytor19, cloning and sequencing the polynucleotide that encodes an antibody and thus as a practicum for teaching a student how to design humanized antibodies. Moreover, antibodies which bind specifically to zcytor19 can be used as a teaching aid for use in detection of B-cell tumor tissue, esophagus, liver, ovary, rectum, stomach, and uterus tumors, and melanoma, pre-B-cell lymphoblastic leukemia and other lymphoid cancers using histological, and in situ methods amongst others known in the art. The zcytor19 gene, polypeptide or antibody would then be packaged by reagent companies and sold to universities and other educational entities so that the students gain skill in art of molecular biology. Because each gene and protein is unique, each gene and protein creates unique challenges and learning experiences for students in a lab practicum. Such educational kits containing the zcytor19 gene, polypeptide or antibody are considered within the scope of the present invention.

The invention is further illustrated by the following non-limiting examples.

EXAMPLES

Example 1

Identification and Isolation of Full-length Human zcytor19 cDNA

Zcytor19 was identified as a predicted full-length cDNA from human genomic DNA AL358412 (Genbank). The sequence of the predicted full length zcytor19 polynucleotide is shown in SEQ ID NO:1 and the corresponding polypeptide is shown in SEQ ID NO:2. A variant full-length zcytor19 cDNA sequence was identified and is shown in SEQ ID NO:18 and the corresponding polynucleotides shown in SEQ ID NO:19. Moreover, a truncated soluble form of zcytor19 cDNA sequence was identified and is shown in SEQ ID NO:20 and the corresponding polypeptide is shown in SEQ ID NO:21.

Example 2

Tissue Distribution in Tissue Panels Using Northern Blot and PCR

A. Human zcytor19 Tissue Distribution using Northern Blot

Human Multiple Tissue Northern Blots (Human 12-lane MTN Blot I and II, and Human Immune System MTN Blot II) (Clontech) are probed to determine the tissue distribution of human zcytor19 expression. A PCR derived probe that hybridizes to SEQ ID NO:1 or SEQ ID NO:18 is amplified using standard PCR amplification methods. An exemplary PCR reaction is carried out as follows using primers designed to hybridize to SEQ ID NO:1, SEQ ID NO:18 or its complement: 30 cycles of 94° C. for 1 minute, 65° C. for 1 minute, and 72° C. for 1 minute; followed by 1 cycle at 72° C. for 7 minutes. The PCR product is visualized by agarose gel electrophoresis and the PCR product is gel purified as described herein. The probe is radioactively labeled using, e.g., the PRIME IT II™ Random Primer Labeling Kit (Stratagene) according to the manufacturer's instructions. The probe is purified using, e.g., a NUCTRAP™ push column (Stratagene). EXPRESSHYB™ (Clontech) solution is used for the prehybridization and as a hybridizing solution for the Northern blots. Prehybridization is carried out, for example, at 68° C. for 2 hours. Hybridization takes place overnight at about 68° C. with about $1.5\times10^6$ cpm/ml of labeled probe. The blots are washed three times at room temperature in 2×SSC, 0.05% SDS, followed by 1 wash for 10 minutes in 2×SSC, 0.1% SDS at 50° C. After exposure to X-ray film, a transcript corresponding to the length of SEQ ID NO:1 SEQ ID NO:18, or SEQ ID NO:20 or of an mRNA encoding SEQ ID NO:2, SEQ ID NO:19 or SEQ ID NO:21 is expected to be seen in tissues that specifically express zcytor19, but not other tissues.

Northern analysis is also performed using Human Cancer Cell Line MTN™ (Clontech). PCR and probing conditions are as described above. A strong signal in a cancer line suggests that zcytor19 expression may be expressed in activated cells and/or may indicate a cancerous disease state. Moreover, using methods known in the art, Northern blots or PCR analysis of activated lymphocyte cells can also show whether zcytor19 is expressed in activated immune cells. Based on electronic Northern information zcytor19 was shown to be expressed specifically in pre-B cell acute lymphoblastic leukemia cells.

B. Tissue Distribution in Tissue Panels Using PCR

A panel of cDNAs from human tissues was screened for zcytor19 expression using PCR. The panel was made in-house and contained 94 marathon cDNA and cDNA samples from various normal and cancerous human tissues and cell lines are shown in Table 5, below. The cDNAs came from in-house libraries or marathon cDNAs from in-house RNA preps, Clontech RNA, or Invitrogen RNA. The marathon cDNAs were made using the marathon-Ready™ kit (Clontech, Palo Alto, Calif.) and QC tested with clathrin primers ZC21195 (SEQ ID NO:6) and ZC21196 (SEQ ID NO:7) and then diluted based on the intensity of the clathrin band. To assure quality of the panel samples, three tests for quality control (QC) were run: (1) To assess the RNA quality used for the libraries, the in-house cDNAs were tested for average insert size by PCR with vector oligos that were specific for the vector sequences for an individual cDNA library; (2) Standardization of the concentration of the cDNA in panel samples was achieved using standard PCR methods to amplify full length alpha tubulin or G3PDH cDNA using a 5' vector oligo ZC14,063 (SEQ ID NO:8) and 3' alpha tubulin specific oligo primer ZC17,574 (SEQ ID NO:9) or 3' G3PDH specific oligo primer ZC17,600 (SEQ ID NO:10); and (3) a sample was sent to sequencing to check for possible ribosomal or mitochondrial DNA contamination. The panel was set up in a 96-well format that included a human genomic DNA (Clontech, Palo Alto, Calif.) positive control sample. Each well contained approximately 0.2-100 pg/μl of cDNA. The PCR was set up using oligos ZC37685 (SEQ ID NO:26) and ZC37681 (SEQ ID NO:27), TaKaRa Ex Taq™ (TAKARA Shuzo Co LTD, Biomedicals Group, Japan), and Rediload dye (Research Genetics, Inc., Huntsville, Ala.). The amplification was carried out as follows: 1 cycle at 94° C. for 2 minutes, 5 cycles of 94° C. for 30 seconds, 70° C. for 30 seconds, 35 cycles of 94° C. for 30 seconds, 64° C. for 30 seconds and 72° C. for 30 seconds, followed by 1 cycle at 72° C. for 5 minutes. About 10 μl of the PCR reaction product was subjected to standard Agarose gel electrophoresis using a 4% agarose gel. The correct predicted DNA fragment size was observed in adrenal gland, bladder, cervix, colon, fetal heart, fetal skin, liver, lung, melanoma, ovary, salivary gland, small intestine, stomach, brain, fetal liver, kidney, prostate, spinal cord, thyroid, placenta, testis, tumor esophagus, tumor liver, tumor ovary, tumor rectum, tumor stomach, tumor uterus, bone marrow, CD3+ library, HaCAT library, HPV library and HPVS library. As this primer pair does not span an intron, there may be risk that some tissues that are contaminated with genomic DNA or unprocessed mRNA messages would create a false positive in this assay.

Therefore, a different primer pair ZC38481 (SEQ ID NO:47) and ZC38626 (SEQ ID NO:48) that span introns were used using the methods described above, to re-evaluate the tissue distribution. The correct predicted DNA fragment size (256 bp) was observed in colon, fetal heart, fetal liver, kidney, liver, lung, mammary gland, prostate, salivary gland, small intestine, adipocyte library, brain library, islet library, and prostate library, RPMI 1788 (B-cell line), spinal cord, placenta library, testis, tumor esophagus, tumor ovary, tumor rectum, tumor stomach, HaCAT library, HPV library and HPVS library.

Mouse tissue panels were also examined using another set of primer pairs: (1) ZC38706 (SEQ ID NO:49) and ZC38711 (SEQ ID NO:50) (800 bp product) using the methods described above. This panel showed a limited tissue distribution for mouse zcytor19: mouse prostate cell lines, salivary gland library, and skin.

TABLE 5

| Tissue/Cell line | #samples |
|---|---|
| Adrenal gland | 1 |
| Bladder | 1 |
| Bone Marrow | 1 |
| Brain | 1 |
| Cervix | 1 |
| Colon | 1 |
| Fetal brain | 1 |
| Fetal heart | 1 |
| Fetal kidney | 1 |
| Fetal liver | 1 |
| Fetal lung | 1 |
| Fetal muscle | 1 |
| Fetal skin | 1 |
| Heart | 2 |
| K562 (ATCC # CCL-243) | 1 |
| Kidney | 1 |
| Liver | 1 |
| Lung | 1 |
| Lymph node | 1 |
| Melanoma | 1 |
| Pancreas | 1 |
| Pituitary | 1 |
| Placenta | 1 |
| Prostate | 1 |
| Rectum | 1 |
| Salivary Gland | 1 |
| Skeletal muscle | 1 |
| Small intestine | 1 |
| Spinal cord | 1 |
| Spleen | 1 |
| Stomach | 1 |
| Testis | 2 |
| Thymus | 1 |
| Thyroid | 1 |
| Trachea | 1 |
| Uterus | 1 |
| Esophagus tumor | 1 |
| Gastric tumor | 1 |
| Kidney tumor | 1 |
| Liver tumor | 1 |
| Lung tumor | 1 |
| Ovarian tumor | 1 |
| Rectal tumor | 1 |
| Uterus tumor | 1 |
| Bone marrow | 3 |
| Fetal brain | 3 |
| Islet | 2 |
| Prostate | 3 |
| RPMI #1788 (ATCC # CCL-156) | 2 |
| Testis | 4 |
| Thyroid | 2 |
| WI38 (ATCC # CCL-75 | 2 |
| ARIP (ATCC # CRL-1674 - rat) | 1 |
| HaCat - human keratinocytes | 1 |
| HPV (ATCC # CRL-2221) | 1 |
| Adrenal gland | 1 |
| Prostate SM | 2 |
| CD3+ selected PBMC's Ionomycin + PMA stimulated | 1 |
| HPVS (ATCC # CRL-2221) - selected | 1 |
| Heart | 1 |
| Pituitary | 1 |
| Placenta | 2 |
| Salivary gland | 1 |
| HL60 (ATCC # CCL-240) | 3 |
| Platelet | 1 |

TABLE 5-continued

| Tissue/Cell line | #samples |
|---|---|
| HBL-100 | 1 |
| Renal mesangial | 1 |
| T-cell | 1 |
| Neutrophil | 1 |
| MPC | 1 |
| Hut-102 (ATCC # TIB-162) | 1 |
| Endothelial | 1 |
| HepG2 (ATCC # HB-8065) | 1 |
| Fibroblast | 1 |
| E. Histo | 1 |

Example 3

PCR-Based Chromosomal Mapping of the zcytor19 Gene

Zcytor19 is mapped to chromosome 1 using the commercially available "GeneBridge 5 4 Radiation Hybrid (RH) Mapping Panel" (Research Genetics, Inc., Huntsville, Ala.). The GeneBridge 4 RH panel contains DNA from each of 93 radiation hybrid clones, plus two control DNAs (the HFL donor and the A23 recipient). A publicly available WWW server allows mapping relative to the Whitehead Institute/MIT Center for Genome Research's radiation hybrid map of the human genome (the "WICGR" radiation hybrid map) which is 10 constructed with the GeneBridge 4 RH panel.

For the mapping of Zcytor19 with the GeneBridge 4 RH panel, 20 µl reactions are set up in a 96-well microtiter plate compatible for PCR (Stratagene, La Jolla, Calif.) and used in a "RoboCycler Gradient 96" thermal cycler (Stratagene). Each of the 95 PCR reactions consisted of 2 µl 10× KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, ZC27,895 (SEQ ID NO:14), 1 µl antisense primer, ZC27,899 (SEQ ID NO:24), 2 µl "RediLoad" (Research Genetics, Inc., Huntsville, Ala.), 0.4 µl 50× Advantage KlenTaq Polymerase Mix (Clontech Laboratories, Inc.), 25 ng of DNA from an individual hybrid clone or control and distilled water for a total volume of 20 µl. The reactions are overlaid with an equal amount of mineral oil and sealed. The PCR cycler conditions are as follows: an initial 1 cycle 5 minute denaturation at 94° C., 35 cycles of a 45 seconds denaturation at 94° C., 45 seconds annealing at 54° C. and 1 minute AND 15 seconds extension at 72° C., followed by a final 1 cycle extension of 7 minutes at 72° C. The reactions are separated by electrophoresis on a 2% agarose gel (EM Science, Gibbstown, N.J.) and visualized by staining with ethidium bromide. The results show that Zcytor19 maps on the chromosome 1 WICGR radiation hybrid map in the 1p36.11 chromosomal region.

Example 4

Construction of Mammalian Expression Vectors That Express zcytor19 Soluble Receptors: zcytor19CEE, zcytor19CFLG, zcytor19CHIS and zcytor19-Fc4

A. Construction of zcytor19 Mammalian Expression Vector Containing zcytor19CEE, zcytor19CFLG and zcytor19CHIS An expression vector is prepared for the expression of the soluble, extracellular domain of the zcytor19 polypeptide, pC4zcytor19CEE, wherein the construct is designed to express a zcytor19 polypeptide comprised of the predicted initiating methionine and truncated adjacent to the predicted transmembrane domain, and with a C-terminal Glu-Glu tag (SEQ ID NO:11).

A zcytor19 DNA fragment comprising the zcytor19 extracellular or cytokine binding domain of zcytor19 described herein, is created using PCR, and purified using standard methods. The excised DNA is subcloned into a plasmid expression vector that has a signal peptide, e.g., the native zcytor19 signal peptide, and attaches a Glu-Glu tag (SEQ ID NO:11) to the C-terminus of the zcytor19 polypeptide-encoding polynucleotide sequence. Such a mammalian expression vector contains an expression cassette having a mammalian promoter, multiple restriction sites for insertion of coding sequences, a stop codon and a mammalian terminator. The plasmid can also have an *E. coli* origin of replication, a mammalian selectable marker expression unit having an SV40 promoter, enhancer and origin of replication, a DHFR gene and the SV40 terminator.

Restriction digested zcytor19 insert and previously digested vector are ligated using standard molecular biological techniques, and electroporated into competent cells such as DH10B competent cells (GIBCO BRL, Gaithersburg, Md.) according to manufacturer's direction and plated onto LB plates containing 50 mg/ml ampicillin, and incubated overnight. Colonies are screened by restriction analysis of DNA prepared from individual colonies. The insert sequence of positive clones is verified by sequence analysis. A large scale plasmid preparation is done using a QIAGEN® Maxi prep kit (Qiagen) according to manufacturer's instructions.

The same process is used to prepare the zcytor19 soluble receptors with a C-terminal his tag, composed of 6 His residues in a row; and a C-terminal FLAG® tag (SEQ ID NO:12), zcytor19CFLAG. To construct these constructs, the aforementioned vector has either the CHIS or the FLAG® tag in place of the glu-glu tag (SEQ ID NO:11).

B. Mammalian Expression Construction of Soluble Human zcytor19 Receptor: zcytor19-Fc4

An expression vector, zcytor19/Fc4/pzmp20, was prepared to express a C-terminally Fc4 tagged soluble version of zcytor19 (human zcytor19-Fc4) in BHK cells. A fragment of zcytor19 cDNA that includes the polynucleotide sequence from extracellular domain of the zcytor19 receptor was fused in frame to the Fc4 polynucleotide sequence (SEQ ID NO:13) to generate a zcytor19-Fc4 fusion (SEQ ID NO:22 and SEQ ID NO:23). The pzmp20 vector is a mammalian expression vector that contains the Fc4 polynucleotide sequence and a cloning site that allows rapid construction of C-terminal Fc4 fusions using standard molecular biology techniques.

A 630 base pair fragment was generated by PCR, containing the extracellular domain of human zcytor19 with BamHI and Bg12 sites coded on the 5' and 3' ends, respectively. This PCR fragment was generated using primers ZC37967 (SEQ ID NO:24) and ZC37972 (SEQ ID NO:25) by amplification from human brain cDNA library. The PCR reaction conditions were as follows: 30 cycles of 94° C. for 20 seconds, and 68° C. for 2 minutes; 1 cycle at 68° C. for 4 minutes; followed by a 10° C. soak. The fragment was digested with BamHI and Bg12 restriction endonucleases and subsequently purified by 1% gel electrophoresis and band purification using QiaQuick gel extraction kit (Qiagen). The resulting purified DNA was ligated for 5 hours at room temperature into a pzmp20 vector previously digested with Bg12 containing Fc4 3' of the Bg12 sites.

One µl of the ligation mix was electroporated in 37 µl DH10B electrocompetent *E. coli* (Gibco) according to the manufacturer's directions. The transformed cells were diluted in 400 μl of LB media and plated onto LB plates containing 100 μg/ml ampicillin. Clones were analyzed by restriction digests and positive clones were sent for DNA sequencing to confirm the sequence of the fusion construct.

Example 5

Transfection And Expression Of Zcytor19 Soluble Receptor Polypeptides

A. Mammalian Expression Human zcytor19 Soluble Receptor: zcytor19/Fc4

BHK 570 cells (ATCC NO: CRL-10314) were plated in T-75 tissue culture flasks and allowed to grow to approximately 50 to 70% confluence at 37° C., 5% $CO_2$, in DMEM/FBS media (DMEM, Gibco/BRL High Glucose, (Gibco BRL, Gaithersburg, Md.), 5% fetal bovine serum, 1 mM L-glutamine (JRH Biosciences, Lenea, Kans.), 1 mM sodium pyruvate (Gibco BRL)). The cells were then transfected with the plasmid zcytor19/Fc4/pzmp20 (Example 4B) using Lipofectamine™ (Gibco BRL), in serum free (SF) media formulation (DMEM, 10 mg/ml transferrin, 5 mg/ml insulin, 2 mg/ml fetuin, 1% L-glutamine and 1% sodium pyruvate). Ten μg of the plasmid DNA zcytor19/Fc4/pzmp20 (Example 4B) was diluted into a 15 ml tube to a total final volume of 500 μl with SF media. 50 μl of Lipofectamine was mixed with 450 μl of SF medium. The Lipofectamine mix was added to the DNA mix and allowed to incubate approximately 30 minutes at room temperature. Four ml of SF media was added to the DNA:Lipofectamine mixture. The cells were rinsed once with 5 ml of SF media, aspirated, and the DNA:Lipofectamine mixture was added. The cells were incubated at 37° C. for five hours, and then 5 ml of DMEM/10% FBS media was added. The flask was incubated at 37° C. overnight after which time the cells were split into the selection media (DMEM/FBS media from above with the addition of 1 μM methotrexate (Sigma Chemical Co., St. Louis, Mo.) in 150 mm plates at 1:2, 1:10, and 1:50. Approximately 10 days post-transfection, one 150 mm plate of 1 μM methotrexate resistant colonies was trypsinized, the cells were pooled, and one-half of the cells were replated in 10 μM methotrexate; to further amplify expression of the zcytor19/Fc4 protein. A conditioned-media sample from this pool of amplified cells was tested for expression levels using SDS-PAGE and Western analysis.

Single clones expressing the soluble receptors can also isolated, screened and grown up in cell culture media, and purified using standard techniques. Moreover, CHO cells are also suitable cells for such purposes.

Example 6

Assessing Zcytor19 Receptor Heterodimerization Using ORIGEN Assay

Soluble zcytor19 receptor zcytor19CFLAG (Example 4 and Example 5), or gp130 (Hibi, M. et al., *Cell* 63:1149-1157, 1990) are biotinylated by reaction with a five-fold molar excess of sulfo-NHS-LC-Biotin (Pierce, Inc., Rockford, Ill.) according to the manufacturer's protocol. Soluble zcytor19 receptor and another soluble receptor subunit, for example, soluble class II cytokine receptors, for example, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511) soluble receptors. Receptors in this subfamily may associate to form homodimers that transduce a signal. These soluble receptors are labeled with a five fold molar excess of Ru-BPY-NHS (Igen, Inc., Gaithersburg, Md.) according to manufacturer's protocol. The biotinylated and Ru-BPY-NHS-labeled forms of the soluble zcytor19 receptor can be respectively designated Bio-zcytor19 receptor and Ru-zcytor19; the biotinylated and Ru-BPY-NHS-labeled forms of the other soluble receptor subunit can be similarly designated. Assays can be carried out using conditioned media from cells expressing a ligand that binds zcytor19 heterodimeric receptors, or using purified ligands. Preferred ligands are those that can bind class II heterodimeric cytokine receptors such as, IL-10, IL-9, IL-TIF, interferons, TSLP (Levine, S D et al., ibid.; Isaksen, D E et al., ibid.; Ray, R J et al., ibid.; Friend, S L et al., ibid.), and the like.

For initial receptor binding characterization a panel of cytokines or conditioned medium are tested to determine whether they can mediate homodimerization of zcytor19 receptor and if they can mediate the heterodimerization of zcytor19 receptor with the soluble receptor subunits described above. To do this, 50 μl of conditioned media or TBS-B containing purified cytokine, is combined with 50 μl of TBS-B (20 mM Tris, 150 mM NaCl, 1 mg/ml BSA, pH 7.2) containing e.g., 400 ng/ml of Ru-zcytor19 receptor and Bio-zcytor19, or 400 ng/ml of Ru-zcytor19 receptor and e.g., Bio-gp130, or 400 ng/ml of e.g., Ru-classIIsubunit and Bio-zcytor19. Following incubation for one hour at room temperature, 30 μg of streptavidin coated, 2.8 mm magnetic beads (Dynal, Inc., Oslo, Norway) are added and the reaction incubated an additional hour at room temperature. 200 μl ORIGEN assay buffer (Igen, Inc., Gaithersburg, Md.) is then added and the extent of receptor association measured using an M8 ORIGEN analyzer (Igen, Inc.).

Example 7

Construct for Generating a zcytor19 Receptor Heterodimer

A vector expressing a secreted human zcytor19 heterodimer is constructed. In this construct, the extracellular cytokine-binding domain of zcytor19 is fused to the heavy chain of IgG gamma 1 (IgGγ1) (SEQ ID NO:14 and SEQ ID NO:15), while the extracellular portion of the heteromeric cytokine receptor subunit (E.g., class II cytokine receptors, for example, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511) receptors)) is fused to a human kappa light chain (human κ light chain) (SEQ ID NO: 16 and SEQ ID NO:17).

A. Construction of IgG Gamma 1 and human κ Light Chain Fusion Vectors

The heavy chain of IgGγ1 (SEQ ID NO:14) is cloned into the Zem229R mammalian expression vector (ATCC deposit No. 69447) such that any desired cytokine receptor extracellular domain having a 5' EcoRI and 3' NheI site can be cloned in resulting in an N-terminal extracellular domain-C-terminal IgGγ1 fusion. The IgGγ1 fragment used in this construct is made by using PCR to isolate the IgGγ1 sequence from a Clontech hFetal Liver cDNA library as a template. PCR products are purified using methods described herein and digested with MluI and EcoRI (Boerhinger-Mannheim), ethanol precipitated and ligated with oligos that comprise an MluI/EcoRI linker, into Zem229R previously digested with and EcoRI using standard molecular biology techniques disclosed herein.

The human κ light chain (SEQ ID NO:16) is cloned in the Zem228R mammalian expression vector (ATCC deposit No. 69446) such that any desired cytokine receptor extracellular domain having a 5' EcoRI site and a 3' KpnI site can be cloned in resulting in a N-terminal cytokine extracellular domain-C-terminal human κ light chain fusion. As a KpnI site is located within the human κ light chain sequence (cleaved by the KpnI enzyme after nucleotide 62 in SEQ ID NO:16), a special primer is designed to clone the 3' end of the desired extracellular domain of a cytokine receptor into this KpnI site: The primer is designed so that the resulting PCR product contains the desired cytokine receptor extracellular domain with a segment of the human κ light chain up to the KpnI site (SEQ ID NO:16). This primer preferably comprises a portion of at least 10 nucleotides of the 3' end of the desired cytokine receptor extracellular domain fused in frame 5' to SEQ ID NO:16. The human κ light chain fragment used in this construct is made by using PCR to isolate the human κ light chain sequence from the same Clontech human Fetal Liver cDNA library used above. PCR products are purified using methods described herein and digested with MluI and EcoRI (Boerhinger-Mannheim), ethanol precipitated and ligated with the MluI/EcoRI linker described above, into Zem228R previously digested with and EcoRI using standard molecular biology techniques disclosed herein.

B. Insertion of zcytor19 Receptor or Heterodimeric Subunit Extracellular Domains into Fusion Vector Constructs Using the construction vectors above, a construct having zcytor19 fused to IgGγ1 is made. This construction is done by PCRing the extracellular domain or cytokine-binding domain of zcytor19 receptor described herein from a prostate cDNA library (Clontech) or activated lymphocyte cDNA library using standard methods, and oligos that provide EcoRI and NheI restriction sites. The resulting PCR product is digested with EcoRI and NheI, gel purified, as described herein, and ligated into a previously EcoRI and NheI digested and band-purified Zem229R/IgGγ1 described above. The resulting vector is sequenced to confirm that the zcytor19/IgG gamma 1 fusion (zcytor19/Ch1 IgG) is correct.

A separate construct having a heterodimeric cytokine receptor subunit extracellular domain fused to κ light is also constructed as above. The cytokine receptor/human κ light chain construction is performed as above by PCRing from, e.g., a lymphocyte cDNA library (Clontech) using standard methods, and oligos that provide EcoRI and KpnI restriction sites. The resulting PCR product is digested with EcoRI and KpnI and then ligating this product into a previously EcoRI and KpnI digested and band-purified Zem228R/human κ light chain vector described above. The resulting vector is sequenced to confirm that the cytokine receptor subunit/human κ light chain fusion is correct.

D. Co-Expression of the zcytor19 and Heterodimeric Cytokine Receptor Subunit Extracellular Domain Approximately 15 μg of each of vectors above, are co-transfected into mammalian cells, e.g., BHK-570 cells (ATCC No. CRL-10314) using LipofectaminePlus™ reagent (Gibco/BRL), as per manufacturer's instructions. The transfected cells are selected for 10 days in DMEM+5% FBS (Gibco/BRL) containing 1 μM of methotrexate (MTX) (Sigma, St. Louis, Mo.) and 0.5 mg/ml G418 (Gibco/BRL) for 10 days. The resulting pool of transfectants is selected again in 10 μm of MTX and 0.5 mg/ml G418 for 10 days.

The resulting pool of doubly selected cells is used to generate protein. Three Factories (Nunc, Denmark) of this pool are used to generate 10 L of serum free conditioned medium. This conditioned media is passed over a 1 ml protein-A column and eluted in about 10, 750 microliter fractions. The fractions having the highest protein concentration are pooled and dialyzed (10 kD MW cutoff) against PBS. Finally the dialyzed material is submitted for amino acid analysis (AAA) using routine methods.

Example 8

Reconstitution of zcytor19 Receptor In Vitro

To identify components involved in the zcytor19-signaling complex, receptor reconstitution studies are performed as follows. For example, BHK 570 cells (ATCC No. CRL-10314) transfected, using standard methods described herein, with a luciferase reporter mammalian expression vector plasmid serve as a bioassay cell line to measure signal transduction response from a transfected zcytor19 receptor complex to the luciferase reporter in the presence of zcytor19 Ligand. BHK cells would be used in the event that BHK cells do not endogenously express the zcytor19 receptor. Other cell lines can be used. An exemplary luciferase reporter mammalian expression vector is the KZ134 plasmid which is constructed with complementary oligonucleotides that contain STAT transcription factor binding elements from 4 genes. A modified c-fos Sis inducible element (m67SIE, or hSIE) (Sadowski, H. et al., *Science* 261:1739-1744, 1993), the p21 SIE1 from the p21 WAF1 gene (Chin, Y. et al., *Science* 272:719-722, 1996), the mammary gland response element of the β-casein gene (Schmitt-Ney, M. et al., *Mol. Cell. Biol.* 11:3745-3755, 1991), and a STAT inducible element of the Fcg RI gene, (Seidel, H. et al., *Proc. Natl. Acad. Sci.* 92:3041-3045, 1995). These oligonucleotides contain Asp718-XhoI compatible ends and are ligated, using standard methods, into a recipient firefly luciferase reporter vector with a c-Fos promoter (Poulsen, L. K. et al., *J. Biol. Chem.* 273:6229-6232, 1998) digested with the same enzymes and containing a neomycin selectable marker. The KZ134 plasmid is used to stably transfect BHK, or BaF3 cells, using standard transfection and selection methods, to make a BHK/KZ134 or BaF3/KZ134 cell line respectively.

The bioassay cell line is transfected with zcytor19 receptor alone, or co-transfected with zcytor19 receptor along with one of a variety of other known receptor subunits. Receptor complexes include but are not limited to zcytor19 receptor only, various combinations of zcytor19 receptor with class II cytokine receptors, for example, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511) receptors. Each independent receptor complex cell line is then assayed in the presence of cytokine-conditioned media or purified cytokines and luciferase activity measured using routine methods. The untransfected bioassay cell line serves as a control for the background luciferase activity, and is thus used as a baseline to compare signaling by the various receptor complex combinations. The conditioned medium or cytokine that binds the zcytor19 receptor in the presence of the correct receptor complex, is expected to give a luciferase readout of approximately 5 fold over background or greater.

As an alternative, a similar assay can be performed wherein the a Baf3/zcytor19 cell line isco-transfected as described herein and proliferation is measured, using a known assay such as a standard Alamar Blue proliferation assay.

Example 9

COS Cell Transfection and Secretion Trap

A secretion trap assay can be used to identify the zcytor19 receptor ligand. Since zcytor19 is a Class II cytokine receptor, the binding of zcytor19sR/Fc4 fusion protein with known or orphan cytokines was tested. The pZP7 expression vectors containing cDNAs of cytokines (including human IL-TIF, interferon alpha, interferon beta, interferon gamma, IL-10, amongst others) are transfected into COS cells, and the binding of zcytor19sR/Fc4 to transfected COS cells are carried out using the secretion trap assay described below. Positive binding in this assay shows potential zcytor19 receptor-ligand pairs.

A. COS Cell Transfections

The COS cell transfection was performed as follows: Mix 0.75 □g cytokine DNA in 50 μl serum free DMEM media (55 mg sodium pyruvate, 146 mg L-glutamine, 5 mg transferrin, 2.5 mg insulin, 1 μg selenium and 5 mg fetuin in 500 ml DMEM (Gibco BRL)), with 5 μl Lipofectamine™ and 45 μl serum free DMEM media. Incubate at room temperature for 30 minutes and then add 400 μl serum free DMEM media. Add this 500 μl mixture onto $1.5\times10^5$ COS cells/well plated on 12-well tissue culture plate and incubate for 5 hours at 37° C. Add 500 μl 20% FBS DMEM media (100 ml FBS, 55 mg sodium pyruvate and 146 mg L-glutamine in 500 ml DMEM) and incubate overnight.

B. Secretion Trap Assay

The secretion trap was performed as follows: Media was rinsed off cells with PBS and then fixed for 15 minutes with 1.8% Formaldehyde in PBS. Cells were then washed 2 times with TNT (0.1M Tris-HCL, 0.15M NaCl, and 0.05% Tween-20 in $H_2O$), and permeabilized with 0.1% Triton-X in PBS for 15 minutes, and washed 3 times with TNT. Cells were blocked for 1 hour with TNB (0.1M Tris-HCL, 0.15M NaCl and 0.5% Blocking Reagent (NEN Renaissance TSA-Direct Kit) in $H_2O$. The cells were incubated for 1 hour with 1 μg/ml, 0.5 μg/ml, or 0.25 μg/ml zcytor19-Fc4 soluble receptor fusion protein (Example 10) in TNB. Cells were then washed 3 times with TNT and were incubated for another hour with 1:1000 diluted goat-anti-human Ig-HRP (Fcγ specific) (Jackson Immuno Research) in TNB. Again cells were washed with TNT.

Positive binding was detected with fluorescein tyramide reagent diluted 1:50 in dilution buffer (NEN kit) and incubated for 4.5 minutes, and washed with TNT. Cells were preserved with Vectashield Mounting Media (Vector Labs Burlingame, Calif.) diluted 1:5 in TNT. Cells were visualized using a FITC filter on fluorescent microscope.

Since zcytor19 is a Class II cytokine receptor, the binding of zcytor19sR/Fc4 fusion protein with known or orphan cytokines is tested. The pZP7 expression vectors containing cDNAs of cytokines (including human IL-TIF, interferon alpha, interferon beta, interferon gamma, IL-10, amongst others are transfected into COS cells, and the binding of zcytor19sR/Fc4 to transfected COS cells are carried out using the secretion trap assay described above. Positive binding in this assay shows potential zcytor19 receptor-ligand pairs.

Example 10

Expression of Human zcytor19 in *E. coli*

A. Construction of zcytor19-MBP Fusion Expression Vector pTAP170/zcytor19

An expression plasmid containing a polynucleotide encoding part of the human zcytor19 fused N-terminally to maltose binding protein (MBP) was constructed via homologous recombination. A fragment of human zcytor19 cDNA (SEQ ID NO:1) was isolated using PCR. Two primers were used in the production of the human zcytor19 fragment in a PCR reaction: (1) Primer ZC39204 (SEQ ID NO:30), containing 40 bp of the vector flanking sequence and 24 bp corresponding to the amino terminus of the human zcytor19, and (2) primer ZC39205 (SEQ ID NO:31), containing 40 bp of the 3' end corresponding to the flanking vector sequence and 24 bp corresponding to the carboxyl terminus of the human zcytor19. The PCR reaction conditions were as follows: 1 cycle of 94 C for 1 minute. Then 20 cycles of 94° C. for 30 seconds, 60° C. for 30 seconds, and 68° C. for 1.5 minutes; followed by 4° C. soak, run in duplicate. Five μl of each 100 μl PCR reaction were run on a 1.0% agarose gel with 1×TBE buffer for analysis, and the expected band of approximately 700 bp fragment was seen. The remaining 95 μl of PCR reaction was combined with the second PCR tube precipitated with 400 μl of absolute ethanol and resuspended in 10 μl of water to be used for recombining into the Sma1 cut recipient vector pTAP170 to produce the construct encoding the MBP-human zcytor19 fusion, as described below.

Plasmid pTAP170 was derived from the plasmids pRS316 and pMAL-c2. The plasmid pRS316 is a *Saccharomyces cerevisiae* shuttle vector (Hieter P. and Sikorski, R., *Genetics* 122:19-27, 1989). pMAL-C2 (NEB) is an *E. coli* expression plasmid. It carries the tac promoter driving MalE (gene encoding MBP) followed by a His tag, a thrombin cleavage site, a cloning site, and the rrnB terminator. The vector pTAP170 was constructed using yeast homologous recombination. 100 ng of EcoR1 cut pMAL-c2 was recombined with 1 μg Pvul cut pRS316, 1 μg linker, and 1 μg Sca1/EcoR1 cut pRS316. The linker consisted of oligos zc19,372 (100 pmole): zc19,351 (1 pmole): zc19,352 (1 pmole), and zc19, 371 (100 pmole) combined in a PCR reaction. Conditions were as follows: 10 cycles of 94° C. for 30 seconds, 50° C. for 30 seconds, and 72° C. for 30 seconds; followed by 4° C. soak. PCR products were concentrated via 100% ethanol precipitation.

One hundred microliters of competent yeast cells (*S. cerevisiae*) were combined with 10 μl of a mixture containing approximately 1 μg of the human zcytor19 insert, and 100 ng of SmaI digested pTAP170 vector, and transferred to a 0.2 cm electroporation cuvette. The yeast/DNA mixture was electropulsed at 0.75 kV (5 kV/cm), infinite ohms, 25 μF. To each cuvette was added 600 μl of 1.2 M sorbitol. The yeast was then plated in two 300 μl aliquots onto two -URA D plates and incubated at 30° C.

After about 48 hours, the Ura+yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 500 μl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 μl ethanol (EtOH), followed by centrifugation for 10 minutes at 4° C. The DNA pellet was resuspended in 100 μl $H_2O$.

Transformation of electrocompetent *E. Coli* cells (MC1061, Casadaban et. al. *J. Mol. Biol.* 138, 179-207) was done with 1 μl yeast DNA prep and 40 μl of MC1061 cells. The cells were electropulsed at 2.0 kV, 25 μF and 400 ohms. Following electroporation, 0.6 ml SOC (2% BactoÎ Tryptone (Difco, Detroit, Mich.), 0.5% yeast extract (Difco), 10 mM NaCl, 2.5 mM KCl, 10 mM MgCl2, 10 mM MgSO4, 20 mM glucose) was added to the cells. After incubation for one hour at 37° C., the cells were plated in one aliquot on LB Kan plates (LB broth (Lennox), 1.8% Bacto™ Agar (Difco), 30 mg/L kanamycin).

Individual clones harboring the correct expression construct for human zcytor19 were identified by expression. Cells were grown in Superbroth II (Becton Dickinson) with 30 μg/ml of kanamycin overnight. 50 μl of the overnight culture was used to inoculate 2 ml of fresh Superbroth II+30 μg/ml kanamycin. Cultures were grown at 37° C., shaking for 2 hours. 1 ml of the culture was induced with 1 mM IPTG. 2-4 hours later the 250 μl of each culture was mixed 250 μl Thorner buffer with 5% βME and dye (8M urea, 100 mM Tris pH7.0, 10% glycerol, 2 mM EDTA, 5% SDS). Samples were boiled for 5-10 minutes. 20 μl were loaded per lane on a 4%-12% PAGE gel (NOVEX). Gels were run in 1×MES buffer. The positive clones were designated pTAP317 and subjected to sequence analysis. The polynucleotide sequence of MBP-zcytor19 fusion within pTAP317 is shown in SEQ ID NO:32, and the corresponding polypeptide sequence of the MBP-zcytor19 fusion is shown in SEQ ID NO:33.

B. Bacterial Expression of Human zcytor19.

Ten microliters of sequencing DNA was digested with Not1 (NEB) in the following reaction to remove the CEN-ARS: 10 μl DNA, 3 μl buffer3 (NEB), 15 μl water, and 2 μl Not1 (10U/μl NEB) at 37° C. for one hour. Then 7 μl of the digest was mixed with 2 μl of 5× buffer and T4DNA ligase (1 u/μl BRL). Reaction was incubated at room temperature for one hour. One microliter of the reaction was transformed into the *E. coli* strain W3110 (ATCC). The cells were electropulsed at 2.0 kV, 25 μF and 400 ohms. Following electroporation, 0.6 ml SOC (2% Bacto™ Tryptone (Difco, Detroit, Mich.), 0.5% yeast extract (Difco), 10 mM NaCl, 2.5 mM KCl, 10 mM MgCl2, 10 mM MgSO4, 20 mM glucose) was added to the cells. After a one hour incubation at 37° C., the cells were plated in one aliquot on LB Kan plates (LB broth (Lennox), 1.8% Bacto™ Agar (Difco), 30 mg/L Kanamycin). Individual clones were analyzed by diagnostic digests for the absence of yeast marker and replication sequence.

A positive clone was used to inoculate an overnight starter culture of Superbroth II (Becton Dickinson) with 30 μg/ml of kanamycin. The starter culture was used to inoculate 4 2L-baffled flasks each filled with 500 ml of Superbroth II+Kan. Cultures shook at 37° C. at 250 rpm until the $OD_{600}$ reached 4.1. At this point, the cultures were induced with 1 m MIPTG. Cultures grew for two more hours at 37° C., 250 rpm at which point 2 ml was saved for analysis and the rest was harvested via centrifugation. Pellet was saved at −80° C. until transferred to protein purification.

Example 11

Purification Scheme for zcytor19-FC4 Fusion

All procedures performed at 4 C, unless otherwise noted. The conditioned media was concentrated first 20 times by using an Amicon/Millipore Spiral cartridge, 10 kD MWCO. (at ambient temperature) The concentrated media was then applied to an appropriately sized POROS 50 A (coupled protein A) column at an optimal capture flow rate. The column was washed with 10 column volumes (CV) of equilibration buffer, then rapidly eluted with 3 CV of 0.1 M Glycine pH 3. The collected fractions had a predetermined volume of 2M TRIS pH 8.0 added prior to the elution to neutralize the pH to about 7.2.

Brilliant Blue (Sigma) stained NuPAGE gels were ran to analyze the elution. Fractions of interested were pooled and concentrated using a 30 kD MWCO centrifugal concentrator to a nominal volume. The concentrated Protein A pool was injected onto an appropriately sized Phamicia Sephacryl 200 column to remove aggregates and to buffer exchange the protein into PBS pH 7.3.Brilliant Blue (Sigma) stained NuPAGE gels were again used to analyze the elution. Fractions were pooled. Western and Brilliant Blue (Sigma) stained NuPAGE gels were ran to confirm purity and content. For further analysis, the protein was submitted for AAA, and N-terminal sequencing. AAA analysis and N-terminal sequencing verified the zcytor19-Fc polypeptide; the N-terminal amino acid sequence was as expected SRPRL APPQX VTLLS QNFSV (SEQ ID NO:34).

Example 12

Human Zcytor19 Expression Based on RT-PCR Analysis of Multiple Tissue and Blood Fraction First-Strand cDNA Panels Gene expression of zcytor19 was examined using commercially available normalized multiple tissue first-strand cDNA panels (OriGene Technologies, Inc. Rockville, Md.; BD Biosciences Clontech, Palo Alto, Calif.). These included OriGene's Human Tissue Rapid-Scan™ Panel (containing 24 different tissues) and the following BD Biosciences Clontech Multiple Tissue cDNA (MTC™) Panels: Human MTC Panel I (containing 8 different adult tissues), Human MTC Panel II (containing 8 different adult tissues), Human Fetal MTC Panel (containing 8 different fetal tissues), Human Tumor MTC Panel (containing carcinomas from 7 different organs), Human Blood Fractions MTC Panel (containing 9 different blood fractions), and Human Immune System MTC Panel (containing 6 different organs and peripheral blood leukocyte).

PCR reactions were set up using zcytor19 specific oligo primers ZC40285 (SEQ ID NO:35) and ZC40286 (SEQ ID NO:36) which yield a 426 bp product, Qiagen HotStarTaq DNA Polymerase (Qiagen, Inc., Valencia, Calif.) and Redi-Load™ dye (Research Genetics, Inc., Huntville, Ala.). The PCR cycler conditions were as follows: an initial 1 cycle 15 minute denaturation at 95° C., 35 cycles of a 45 second denaturation at 95° C., 1 minute annealing at 63° C. and 1 minute and 15 seconds extension at 72° C., followed by a final 1 cycle extension of 7 minutes at 72° C. The reactions were separated by electrophoresis on a 2% agarose gel (EM Science, Gibbstown, N.J.) and visualized by staining with ethidium bromide.

A DNA fragment of the correct size was observed in the following human adult tissues: adrenal gland, bone marrow, colon, heart, liver, lung, lymph node, muscle, ovary, pancreas, placenta, prostate, salivary gland, small intestine, spleen, stomach, testis, thyroid, and tonsil. A DNA fragment of the correct size was observed in the following human fetal tissues: heart, liver, lung, kidney, skeletal muscle, spleen, and thymus. A DNA fragment of the correct size was observed in the following human blood fractions: peripheral blood leukocyte, mononuclear cells (B-cells, T-cells, and monocytes), resting CD8+ cells (T-suppressor/cytotoxic), resting CD19+ cells (B-cells), activated CD19+cells, activated mononuclear cells, and activated CD4+ cells. A DNA fragment of the correct size was observed in the following tumor tissues: breast carcinoma, colon adenocarcinoma, lung carcinoma, ovarian carcinoma, pancreatic adenocarcinoma, and prostatic adenocarcinoma.

Because zcytor19 is expressed in these specific tumor tissues, zcytor19 polynucleotides, polypeptides and antibodies can be used as a tumor marker as disclosed herein. Moreover, an antibody to zcytor19 could have anti-tumor activity, as well as toxin-conjugates, cytokine conjugates or other conjugates of an antibody, or the zcytor19 receptor ligand itself. The antagonist of zcytor19 ligand, such as anti-zcytor19 antibodies or soluble receptors can also act as anti-tumor reagents.

Example 13

Generation and Analysis of zcytor19 KO Mice

A. Identification of BAC Clones Positive for Mouse zcytor19 Gene

One BAC clone positive for mouse zcytor19 gene was identified using Incyte Genomic's (St. Louis, Mo.) Easy-to-Screen DNA Pools, BAC Mouse ES (Release I) following Manufacturer's instructions. Oligonucleotides were designed to generate a PCR fragment containing partial exon 6, complete intron 6 and partial exon 7 sequences.

PCR reactions were carried out in 25 μl using 1.75 units of Advantage 2 polymerase (Clontech). Either 2 μl or 10 μl of BAC library DNA was used as template in buffer containing 67 mM Tris pH 8.8, 16.6 mM $(NH_4)_2SO_4$, 6.7 mM $MgCl_2$ 5 mM 2-Mercaptoethanol, 100 μg/ml gelatin, 10% Dimethyl Sulfoxide, 1 mM deoxynucleotides, 140 nM forward primer ZC39128 (SEQ ID NO:37) and 140 nM reverse primer ZC39129 (SEQ ID NO:38). PCR conditions were as follows 95° C. for 1 min,; 30 cycles of 95° C. for 15 seconds, 55° C. for 30 seconds, and 68° C. for 30 seconds; and 68° C. for 2 minutes; followed by a 4° C. hold. PCR products were analyzed by agarose gel electrophoresis. Positive PCR products were found to be 1,149 bp.

Four additional BAC clones positive for mouse zcytor19 gene were identified using Incyte's BAC Mouse Filter Set (Release II) following Manufacturer's instructions. Oligonucleotides were designed to generate a PCR fragment containing partial exon 6, and partial exon 7 sequences from mouse cDNA template.

PCR reactions were carried out in 25 μl using 1.75 units of Advantage 2 polymerase (Clontech). 2 μl of Neonatal Mouse skin cDNA library (JAK 062700B) was used as template in buffer containing 67 mM Tris pH 8.8, 16.6 mM $(NH_4)_2SO_4$, 6.7 mM $MgCl_2$ 5 mM 2-Mercaptoethanol, 100 μg/ml gelatin, 10% Dimethyl Sulfoxide, 1 mM deoxynucleotides, 140 nM forward primer ZC39128 (SEQ ID NO:37) and 140 nM reverse primer ZC39129 (SEQ ID NO:38). PCR conditions were as described above. PCR products were separated by agarose gel electrophoresis and purified using Qiaquick (Qiagen) gel extraction kit. The isolated, approximately 400 bp, DNA fragment was labeled using Prime-It II (Stratagene) Random Primer labeling kit and purified using MicroSpin S-200HR columns (AmershamPharmacia).

The labeled probe was used to screen Incyte's 7 filter BAC library set. Hybridizations were carried out at 55° C. overnight using ExpressHyb (Clontech). Filters were then washed 3 times for 30 minutes at 50° C. with 0.1×SSC, 01% SDS, autoradiographed overnight and compared to manufacturer's grid patterns to identify positive clones.

B. Characterization of zcytor19 Mouse Positive BACs.

Five zcytor19 mouse positive BAC clones from 129/SvJ Embryonic Stem Cell libraries (Release I and II) were obtained from Incyte Genomics. BAC clones were grown within *Escherichia coli* host strain DH10B in liquid media and extracted using BAC large plasmid purification kit MKB-500 (Incyte Genomics) according to manufacturer's instructions. 4 of 5 BACs were found to contain at least 2,000 bp of 5' untranslated region, exon1, and exon 5 as determined by PCR. 100 ng of each BAC DNA was used as template using the following conditions: PCR reactions were carried out in 25 μl using 1.75 units of Advantage 2 polymerase (Clontech) in buffer containing 67 mM Tris pH 8.8, 16.6 mM $(H_4)_2SO_4$, 6.7 mM $MgCl_2$, 5 mM 2-Mercaptoethanol, 100 μg/ml gelatin, 10% Dimethyl Sulfoxide, 1 mM deoxynucleotides, 140 nM forward and 140 nM reverse primer. PCR conditions were as follows 95° C. for 1 min,; 30 cycles of 95° C. for 15 seconds, 55° C. for 30 seconds, and 68° C. for 30 seconds; and 68° C. for 2 minutes; followed by a 4° C. hold. PCR products were analyzed by agarose gel electrophoresis. Using forward primer ZC40784 (SEQ ID NO:39) and reverse primer ZC40785 (SEQ ID NO:40) partial 5' UTR was amplified and found to be 957 bp. Using forward primer ZC40786 (SEQ ID NO:41) and reverse primer ZC40787 (SEQ ID NO:42) partial 5' UTR, complete exon 1 and partial intron 1 was amplified and found to be approximately 950 bp. Using forward primer ZC39128 (SEQ ID NO:37) and forward primer ZC39129 (SEQ ID NO:38) containing partial exon 6, complete intron 6 and partial exon 7 sequence was amplified and found to be 1,149 bp.

Four of the 5 BAC clones were found to contain at least 3,796 bp of 5' UTR and at 6,922 bp of 3' UTR by Southern Blot analysis. Oligonucleotides ZC40784 (SEQ ID NO:39) and ZC39129 (SEQ ID NO:38) were end labeled using T4 polynucleotide kinase (Roche) and used to probe Southern Blots containing 5 BAC candidates digested with restriction endonucleases EcoRI (Life Technologies) and XbaI (New England Biolabs). Results indicated 4 of 5 BACs contained at least 3,796 bp of 5' UTR and 5 of 5 BACs contained at least 6,922 bp of 3' UTR.

C. Determination of zcytor19 Mouse Intron 6 Sequence.

Oligonucleotides were designed to generate a PCR fragment containing partial exon 6, complete intron 6 and partial exon 7 sequences.

PCR reactions were carried out in 25 μl using 1.75 units of Advantage 2 polymerase (Clontech). 100 ng of 129/Sv mouse genomic DNA was used as template in buffer containing 67 mM Tris pH 8.8, 16.6 mM $(NH_4)_2SO_4$, 6.7 mM $MgCl_2$, 5 mM 2-Mercaptoethanol, 100 μg/ml gelatin, 10% Dimethyl Sulfoxide, 1 mM deoxynucleotides, 140 nM forward primer ZC39128 (SEQ ID NO:37) and 140 nM reverse primer ZC39129 (SEQ ID NO:38). PCR conditions were as described above. PCR products were analyzed by agarose gel electrophoresis and found to be 1,149 bp. PCR products were then purified using Qiaquick (Qiagen) PCR purification kit. Determination of intron 6 sequence was made by sequence analysis using oligos ZC39128 (SEQ ID NO:37) and ZC 39129 (SEQ ID NO:38).

D. Determination of zcytor19 Mouse Intron 5 Sequence

Oligonucleotides were designed to generate a PCR fragment containing partial exon5, complete intron5 and partial exon6. PCR reactions were carried out in 25 μl using 1.75 units of Advantage 2 polymerase (Clontech). 100 ng of 129/Sv mouse genomic DNA was used as template in buffer containing 67 mM Tris pH 8.8, 16.6 mM $(NH_4)_2SO_4$, 6.7 mM $MgCl_2$, 5 mM 2-Mercaptoethanol, 100 μg/ml gelatin, 10% Dimethyl Sulfoxide, 1 mM deoxynucleotides, 140 nM forward primer ZC39408 (SEQ ID NO:43) and 140 nM reverse primer ZC39409 (SEQ ID NO:44). PCR conditions were as follows 95° C. for 1 min,; 30 cycles of 95° C. for 15 seconds, 55° C. for 30 seconds, and 68° C. for 30 seconds; and 68° C. for 2 minutes; followed by a 4° C. hold. PCR products were analyzed by agarose gel electrophoresis and found to be 356 bp. PCR products were then purified using Qiaquick (Qiagen) PCR purification kit. Determination of intron 6 sequence was made by sequence analysis using oligos ZC39408 (SEQ ID NO:43) and ZC 39409 (SEQ ID NO:44).

E. Design of Oligonucleotides for Generating of KO Constructs of the Mouse zcytor19 Gene To investigate biological function of zcytor19 gene, a knockout mouse model is being generated by homologous recombination technology in embryonic stem (ES) cells. In this model, the coding exon 1, 2 and 3 are deleted to create a null mutation of the zcytor19 gene. This deletion removes the translation initiation codon, the signal domain and part of the extracellular domain of the zcytor19 protein, thus inactivating the zcytor19 gene.

ET cloning technique will be used to generate the KO vector (Stewart et al, *Nucl. Acids Res.* 27:6, 1999) First, Kanomycin resistance cassette is used to replace introns1, 2 and 3 of zcytor19 mouse gene. A forward knockout oligonucleotide (SEQ ID NO:45) was designed to be 121 nucleotides in length, having 52 bp of homology to the 5'UTR of zcytor19m a 42 bp linker having SfiI, FseI, BamHI and HindIII restriction sites and 27 bp of homology to the 5' end of the Kanomycin resistance cassette. A reverse knockout oligonucleotide (SEQ ID NO:46) was designed to be 125 nucleotides in length, having 50 bp of homology to intron 3 of zcytor19 mouse, a 48 bp linker having SfiI, AscI, BamHI and HindIII restriction sites and 27 bp of homology to the 3' end of the Kanomycin resistance cassette. The above oligonucleotides can be used to synthesize a PCR fragment 1073 bp in length containing the entire Kanomycin resistance cassette with the first 52 bp having homology to the 5' UTR of zcytor19 mouse and the last 50 bp having homology to intron 3.

The fragment will then be used to construct a Knockout vector through ET Cloning, in which cytor19 mouse positive BAC cell hosts are made competent through treatment with glycerol then transfected with the plasmid pBADalpha/beta/gamma(Amp). Resistance to chloramphenical and ampicillin selects for transformed cell. Cells are then re-transformed with the Kanomycin PCR fragment containing homology arms. The Beta and gamma recombination proteins of pBAD-alpha/beta/gamma(Amp) are induced by the addition of arabinose to the growth media through the activation of the Red alpha gene. Recombinant BACs are selected for by resistance to kanomycin and ampicillin then screened by PCR. Once a recombinant BAC is identified a fragment is subcloned containing at least 1,800 bp of sequence upstream of kanomycin resistance cassette insertion and at least 6,000 bp of sequence downstream into a pGEM7 derived vector. The Kanomycin resistance cassette is then replaced by standard ligation cloning with a IRES/LacZ/Neo-MC1 cassette. The IRES is an internal ribosome entry sequence derived from encephalomyocarditis virus. It is fused in-frame to the reporter lacZ gene, linked to a polyA signal. Downstream of the IRES/LacZ reporter gene, MC1 promoter drives the expression of a G418 resistance selectable marker Neo gene. The selectable maker cassette contains termination codons in all three reading frames. Thus, the drug resistance gene Neo is used for selection of homologous recombination events in embryonic stem (ES) cells. IRES/LacZ reporter gene will be used to monitor the expression of the replaced gene after homologous recombination Homologous recombination of the knockout vector and the target locus in ES cells leads to the replacement of a total 17,980 bp, including complete exons 1, 2 and 3, of the wild type locus with the IRES/LacZ/Neo-MC1 cassette, which is about 5,200 bp in length.

F. Generation of zCytor19 KO Mice

The KO vector, described above, is linearized by PmeI digestion, and electroporated into ES cells. Homologous recombination events are identified by PCR screening strategy, and confirmed by Southern Blot Analysis, using a standard KO protocol. See, A. L. Joyner, *Gene Targeting. A Practical Approach*, IRL Press 1993.

Once homologous recombination events are identified, ES cells will be expanded, and injected into blastocysts to generate chimeras. Chimeric males will be used to breed to C57black females to achieve germ line transmission of the null mutation, according to standard procedures. See Hogan, B. et al., *Manipulating the Mouse Embryo. A Laboratory Manual*, Cold Spring Harbor Laboratory Press, 1994.

Heterozygous KO animals will be bred to test biological functions of the zcytor19 gene. Of offspring produced, ¼ should be wild type, ½ should be heterozygous, and ¼ should be homozygous. Homozygous will be analyzed in details as described below.

G. Microscopic Evaluation of Tissues from zcytor19 Homozygous Animals.

Since zcytor19 is expressed in following tissues, we will examine these tissues carefully: colon, ovary placenta, pituitary, lymph node, small intestine, salivary gland, rectum, prostate, testis, brain, lung, kidney, thyroid, spinal cord, bone marrow, and cervix.

Spleen, thymus, and mesenteric lymph nodes are collected and prepared for histologic examination from transgenic animals expressing zcytor19. Other tissues which are routinely harvested included the following: Liver, heart, lung, spleen, thymus, mesenteric lymph nodes, kidney, skin, mammary gland, pancreas, stomach, small and large intestine, brain, salivary gland, trachea, esophagus, adrenal, pituitary, reproductive tract, accessory male sex glands, skeletal muscle including peripheral nerve, and femur with bone marrow. The tissues are harvested from homozygous animals as well as wild type controls. Samples are fixed in 10% buffered formalin, routinely processed, embedded in paraffin, sectioned at 5 microns, and stained with hematoxylin and eosin. The slides are examined for histological, and pathological changes, such as inflammatory reactions, and hypo-proliferation of certain cell types.

H. Flow Cytometric Analysis of Tissues from Homozygous Mouse Mutants Missing zcytor19.

Homozygous animals missing zcytor19 gene are to be sacrificed for flow cytometric analysis of peripheral blood, thymus, lymph node, bone marrow, and spleen.

Cell suspensions are made from spleen, thymus and lymph nodes by teasing the organ apart with forceps in ice cold culture media (500 ml RPMI 1640 Medium (JRH Biosciences. Lenexa, Kans.); 5 ml 100× L-glutamine (Gibco BRL. Grand Island, N.Y.); 5 ml 100× Na Pyruvate (Gibco BRL); 5 ml 100× Penicillin, Streptomycin, Neomycin (PSN) (Gibco BRL) and then gently pressing the cells through a cell strainer (Falcon, VWR Seattle, Wash.). Peripheral blood (200 ml) is collected in heparinized tubes and diluted to 10 mls with HBSS containing 10 U Heparin/ml. Erythrocytes are removed from spleen and peripheral blood preparations by hypotonic lysis. Bone marrow cell suspensions are made by flushing marrow from femurs with ice-cold culture media. Cells are counted and tested for viability using Trypan Blue (GIBCO BRL, Gaithersburg, Md.). Cells are resuspended in ice cold staining media (HBSS, 1% fetal bovine serum, 0.1% sodium azide) at a concentration of ten million per milliliter. Blocking of Fc receptor and non-specific binding of antibodies to the cells was achieved by adding 10% normal goat sera and Fc Block (PharMingen, La Jolla, Calif.) to the cell suspension.

Cell suspensions are mixed with equal volumes of fluorochrome labeled monoclonal antibodies (PharMingen), incubated on ice for 60 minutes and then washed twice with ice cold wash buffer (PBS, 1% fetal bovine serum, 0.1% sodium azide) prior to resuspending in 400 ml wash buffer containing 1 mg/ml 7-AAD (Molecular Probes, Eugene, Oreg.) as a viability marker in some samples. Flow data was acquired on a FACSCalibur flow cytometer (BD Immunocytometry Systems, San Jose, Calif.). Both acquisition and analysis were performed using CellQuest software (BD Immunocytometry Systems).

The cell populations in all lymphoid organs will be analyzed to detect abnormalities in specific lineages of T cell, B cell, or other lymphocytes, and cellularity in these organs.

Example 14

Identification of Cells Expressing zcytor19 Using In Situ Hybridization

Human tissues from cervical carcinoma, normal and carcinoma colon, duodenum, endometrial carcinoma, normal and carcinoma ovary, uterus, heart, liver, lung, muscle sarcoma, and normal and carcinoma skin were screened for zcytor 19 expression by in situ hybridization. The tissues were fixed in 10% buffered formalin and blocked in paraffin using standard techniques. Tissues were sectioned at 5 microns. Tissues were prepared using a standard protocol. Briefly, tissue sections were deparaffinized with HistoClear (National Diagnostics, Atlanta, Ga.) and then dehydrated with ethanol. Next they were digested with Proteinase K (50 μ/ml) (Boehringer Diagnostics, Indianapolis, Ind.) at 23° C. for 4-15 minutes. This step was followed by acetylation and re-hydration of the tissues.

One in situ probe was designed against the human zcytor19 sequence. Plasmid DNA 100933 was digested with restriction enzyme HindIII, which covers 0.7 kb from the end of 3'UTR. The T-7 RNA polymerase was used to generate an antisense probe. The probe was labeled with digoxigenin (Boehringer) using an In Vitro transcription System (Promega, Madison, Wis.) as per manufacturer's instruction.

In situ hybridization was performed with a digoxigenin- or biotin-labeled zcytor19 probe (above). The probe was added to the slides at a concentration of 1 to 5 pmol/ml for 12 to 16 hours at 60° C. Slides were subsequently washed in 2×SSC and 01×SSC at 55° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

Positive signal were observed in most of carcinoma samples. In cervical carcinoma, carcinoma epithelial cells were positive. There were also some signals in a subset of lymphocytes in the lymphoid follicles. Similarly, both carcinoma and some immune cells were positive in the colon carcinoma samples, while normal colon samples were negative. Weak staining was also in the endometrial carcinoma and ovarian carcinoma, while normal ovary and uterus were negative. There was weak staining in the cancer area of the muscle sarcoma sample. Keratinocytes were positive in the skin carcinoma and Kaposi's sarcoma samples, while no staining was observed in the normal skin. In heart and liver, a subset of cells possibly circulating WBC, were positive for zcytor19. It appears endothelial cells in some vessels may also be positive. In lung, type II pneumocytes and macrophage-like cells were positive. Bronchial epithelium and endothelium were also positive in some lung specimens. In summary, zcytor19 appears to be up-regulated in carcinoma cells. There is low level of zcytor19 mRNA in a subset of lymphocytes and endothelial cells.

Because zcytor19 is expressed in these specific tumor tissues, zcytor19 polynucleotides, polypeptides and antibodies can be used as a tumor marker as disclosed herein. Moreover, an antibody to zcytor19 could have anti-tumor activity, as well as toxin-conjugates, cytokine conjugates or other conjugates of an antibody, or the zcytor19 receptor ligand itself. The antagonist of zcytor19 ligand, such as anti-zcytor19 antibodies or soluble receptors can also act as anti-tumor reagents.

Example 15

Construction of BaF3 Cells Expressing the zcytor19 Receptor (BaF3 Zcytor19 cells) with Puromycin Resistant and Zeomycin Resistant Vectors Two types of BaF3 cells expressing the full-length zcytor19 receptor were constructed using 30 μg of zcytor19 expression vectors, one resistant to puromycin, one resistant to zeomycin described below. The BaF3 cells expressing the zcytor19 receptor mRNA with puromycin resistance were designated as BaF3/zcytor19-p. The BaF3 cells expressing the zcytor19 receptor mRNA with zeomycin resistance were designated as BaF3/zcytor19-z.

A. Construction of BaF3 Cells Expressing the zcytor19 Receptor

BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL). Prior to electroporation, pZP-5N/CRF2-4 was prepared and purified using a Qiagen Maxi Prep kit (Qiagen) as per manufacturer's instructions. BaF3 cells for electroporation were washed twice in PBS (Gibco BRL) and then resuspended in RPMI media at a cell density of $10^7$ cells/ml. One ml of resuspended BaF3 cells was mixed with 30 μg of the pZP-7p/zcytor19 plasmid DNA, or 30 □g of the pZP-7z/ zcytor19 plasmid DNA, and transferred to separate disposable electroporation chambers (GIBCO BRL). The cells were given two serial shocks (800 1Fad/300 V.; 1180 1Fad/300 V.) delivered by an electroporation apparatus (CELL-PORATOR™; GIBCO BRL), with a 1 minute rest between the shocks. After a 5 minute recovery time, the electroporated cells were transferred to 50 ml of complete media and placed in an incubator for 15-24 hours (37° C., 5% $CO_2$). The cells were then spun down and resuspended in 50 ml of complete media containing Puromycin (Clonetech) selection (2 □g/ml) for the cells transfected with pZP-7p/zcytor19, or Zeocin selection (1:150-1:333) for the cells transfected with pZP-7z/zcytor19, and placed in a T-162 flask to isolate the antibiotic-resistant pools. Pools of the transfected BaF3 cells, hereinafter called BaF3/zcytor19-puro and BaF3/zcytor19-zeo cells, were assayed for expression of zcytor19 by RT-PCR.

B. Confirmation of zcytor19 Expression by RT-PCR.

The BaF3/zcytor19-puro and BaF3/zcytor19-zeo cells were harvested for RNA, which was then put into a reverse transcriptase reaction, and subsequently tested by PCR for the presence of zcytor19.

Flasks of cells were grown to confluence, then 10 ml were removed and spun down to obtain a cell pellet. RNA was purified from the pellet using the RNeasy Total RNA Purification kit, with the additional RNase-free DNase set (Qiagen), following the manufacturer's protocol. Reverse transcription was then done on the samples using the StrataScript RT-PCR kit (Stratagene), following the manufacturer's protocol through the completion of the RT reaction. PCR was then done by mixing 0.2 pmol each of primers ZC40279 and ZC37863, 0.2 mM of dNTP mix (Roche) containing equal amounts of each nucleotide, 5 μl of 10× cDNA PCR Reaction Buffer (Clonetech), 3 μl DNA from the RT reaction, 0.5 μl Advantage2 Polymerase (Clonetech), made to a final volume of 50 μl with water. The reaction ran for 95° C., 5 min, then 30 cycles of 95° C. 30 sec, 60° C. 30 sec, 72° C. 1 min, then 72° C. 7 min and a 4° C. soak, on a Perkin Elmer GeneAmp PCR System 2400. The samples were mixed with 3 ml loading dye, and 25 ml was run on a 1% OmniPur Agarose (Merck) gel. Zcytor19 bands were detected on the gel for both BaF3/zcytor19-puro and BaF3/zcytor19-zeo, indicating that those cells are expressing the gene.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide comprising the nucleotide sequence as shown in SEQ ID NO:18 from nucleotide 61 to nucleotide 1560 or the RNA equivalent thereof.

2. The isolated polynucleotide according to claim 1, wherein the polynucleotide comprises a stop codon at the carboxyl terminus.

3. The isolated polynucleotide according to claim 1, wherein the polynucleotide comprises the nucleotide sequence as shown in SEQ ID NO: 18 from nucleotide 1 to nucleotide 1560.

4. The isolated polynucleotide according to claim 1, wherein the polynucleotide comprises the nucleotide sequence as shown in SEQ ID NO: 18 from nucleotide 1 to nucleotide 1563.

5. The isolated polynucleotide according to claim 1, wherein the polynucleotide consists of the nucleotide sequence.

6. A vector comprising the nucleotide sequence as shown in SEQ ID NO: 18 from nucleotide 61 to nucleotide 1560.

7. The vector according to claim 6, wherein the nucleotide sequence comprises a stop codon at the carboxyl terminus.

8. An isolated host cell comprising a vector, wherein the vector comprises the nucleotide sequence as shown in SEQ ID NO: 18 from nucleotide 61 to nucleotide 1560.

* * * * *